(12) United States Patent
Wall et al.

(10) Patent No.: US 11,176,444 B2
(45) Date of Patent: Nov. 16, 2021

(54) MODEL OPTIMIZATION AND DATA ANALYSIS USING MACHINE LEARNING TECHNIQUES

(71) Applicant: Cognoa, Inc., Palo Alto, CA (US)

(72) Inventors: Dennis Wall, Palo Alto, CA (US); Sharief Khalil Taraman, Palo Alto, CA (US); Brent Vaughan, Palo Alto, CA (US); Abdelhalim Abbas, San Jose, CA (US)

(73) Assignee: COGNOA, INC., Palo Alto, CA (US)

( * ) Notice: Subject to any disclaimer, the term of this patent is extended or adjusted under 35 U.S.C. 154(b) by 0 days.

(21) Appl. No.: 17/088,428

(22) Filed: Nov. 3, 2020

(65) Prior Publication Data

US 2021/0133509 A1 May 6, 2021

Related U.S. Application Data

(63) Continuation of application No. PCT/US2020/024029, filed on Mar. 20, 2020.
(Continued)

(51) Int. Cl.
*G06N 20/00* (2019.01)
*G06N 3/04* (2006.01)
*G06K 9/62* (2006.01)
*G06N 3/02* (2006.01)
*G06N 3/08* (2006.01)

(52) U.S. Cl.
CPC ........ *G06N 3/0454* (2013.01); *G06K 9/6227* (2013.01); *G06K 9/6228* (2013.01); *G06N 3/02* (2013.01); *G06N 3/08* (2013.01); *G06N 20/00* (2019.01); *G06K 9/6262* (2013.01)

(58) Field of Classification Search
CPC ........ G06N 3/0454; G06N 20/00; G06N 3/02; G06N 3/08; G06K 9/6227; G06K 9/6228; G06K 9/6262; G16H 10/20; G16H 50/70; G16H 50/20; G16H 20/70; G09B 19/00
See application file for complete search history.

(56) References Cited

U.S. PATENT DOCUMENTS 4,860,214 A   8/1989   Matsuda et al.
5,722,418 A   3/1998   Bro
(Continued)

FOREIGN PATENT DOCUMENTS

CN   1918575 A   2/2007
CN   101499078 A   8/2009
(Continued)

OTHER PUBLICATIONS

European Application No. 18750938.5 Search Report dated Oct. 16, 2020.
(Continued)

*Primary Examiner* — Aaron W Carter
(74) *Attorney, Agent, or Firm* — Wilson Sonsini Goodrich & Rosati

(57) ABSTRACT

Disclosed herein are platforms, systems, devices, methods and media for model optimization and data analysis using machine learning. Input data can be processed and analyzed to identify relevant discriminating features, which can be modeled using a plurality of machine learning models. A computing device can be configured with one or more optimized models for categorizing input data.

16 Claims, 44 Drawing Sheets

Related U.S. Application Data

(60) Provisional application No. 62/822,186, filed on Mar. 22, 2019.

(56) References Cited

U.S. PATENT DOCUMENTS

| | | |
|---|---|---|
| 6,186,145 B1 * | 2/2001 | Brown ............... A63F 13/005 128/897 |
| 6,425,764 B1 | 7/2002 | Lamson |
| 6,569,093 B2 | 5/2003 | Iliff |
| 6,957,202 B2 | 10/2005 | Skaanning et al. |
| 7,043,439 B2 | 5/2006 | Jost et al. |
| 7,155,421 B1 | 12/2006 | Haldar |
| 7,311,666 B2 | 12/2007 | Stupp et al. |
| 7,958,066 B2 | 6/2011 | Pinckney et al. |
| 7,974,872 B2 | 7/2011 | Katayama et al. |
| 8,024,332 B2 | 9/2011 | Cao et al. |
| 8,655,817 B2 | 2/2014 | De et al. |
| 8,834,174 B2 | 9/2014 | Malik |
| 9,305,059 B1 | 4/2016 | Glickman et al. |
| 9,443,199 B2 | 9/2016 | Pinckney et al. |
| 9,443,205 B2 | 9/2016 | Wall |
| 10,311,645 B1 | 6/2019 | Ravindran et al. |
| 10,478,112 B2 | 11/2019 | Wall |
| 10,984,899 B2 | 4/2021 | Vaughan |
| 2001/0034615 A1 | 10/2001 | Wilkinson et al. |
| 2001/0036444 A1 | 11/2001 | Placke et al. |
| 2002/0002325 A1 | 1/2002 | Iliff |
| 2002/0019747 A1 | 2/2002 | Ware et al. |
| 2002/0035486 A1 | 3/2002 | Huyn et al. |
| 2002/0042786 A1 | 4/2002 | Scarborough et al. |
| 2003/0032069 A1 | 2/2003 | Muraca |
| 2003/0191680 A1 | 10/2003 | Dewar |
| 2004/0015337 A1 | 1/2004 | Thomas et al. |
| 2004/0103001 A1 | 5/2004 | Mazar et al. |
| 2004/0147840 A1 | 7/2004 | Duggirala et al. |
| 2004/0197750 A1 * | 10/2004 | Donaher ............... G09B 21/00 434/236 |
| 2004/0265784 A1 | 12/2004 | Stout |
| 2005/0075887 A1 | 4/2005 | Bernard et al. |
| 2005/0142524 A1 | 6/2005 | Simon et al. |
| 2005/0176057 A1 | 8/2005 | Bremer et al. |
| 2005/0187802 A1 | 8/2005 | Koeppel |
| 2005/0197988 A1 | 9/2005 | Bublitz |
| 2005/0209785 A1 | 9/2005 | Wells et al. |
| 2005/0216243 A1 | 9/2005 | Graham et al. |
| 2005/0260549 A1 | 11/2005 | Feierstein et al. |
| 2006/0009683 A1 | 1/2006 | Sakai et al. |
| 2006/0059145 A1 | 3/2006 | Henschke et al. |
| 2006/0078856 A1 | 4/2006 | Kellman |
| 2006/0282306 A1 | 12/2006 | Thissen-Roe |
| 2007/0118399 A1 | 5/2007 | Avinash et al. |
| 2007/0207449 A1 | 9/2007 | Feierstein |
| 2008/0014566 A1 * | 1/2008 | Chapman ............... G06F 19/00 434/262 |
| 2008/0016024 A1 | 1/2008 | Andoh et al. |
| 2009/0007924 A1 | 1/2009 | Iliff |
| 2009/0016559 A1 | 1/2009 | Cleary |
| 2009/0083075 A1 | 3/2009 | Henschke et al. |
| 2009/0137923 A1 | 5/2009 | Suffin et al. |
| 2009/0182578 A1 | 7/2009 | Ozersky |
| 2009/0259494 A1 | 10/2009 | Feder et al. |
| 2010/0023346 A1 | 1/2010 | Paty et al. |
| 2010/0068687 A1 | 3/2010 | Bertelsen |
| 2010/0177950 A1 | 7/2010 | Donovan et al. |
| 2010/0179928 A1 | 7/2010 | Hodgin |
| 2010/0184093 A1 | 7/2010 | Donovan et al. |
| 2010/0189818 A1 | 7/2010 | Tsai |
| 2010/0280760 A1 | 11/2010 | Pi et al. |
| 2011/0082712 A1 | 4/2011 | Eberhardt, III |
| 2011/0119212 A1 | 5/2011 | Bruin et al. |
| 2011/0145161 A1 | 6/2011 | Scarborough et al. |
| 2011/0184379 A1 | 7/2011 | Van Antwerp et al. |
| 2012/0004925 A1 | 1/2012 | Braverman et al. |
| 2012/0059282 A1 | 3/2012 | Agichtein et al. |
| 2012/0101852 A1 | 4/2012 | Albert |
| 2012/0102405 A1 | 4/2012 | Zuckerman et al. |
| 2012/0108909 A1 * | 5/2012 | Slobounov ............ G16H 50/30 600/300 |
| 2012/0270199 A1 | 10/2012 | Malik |
| 2013/0159010 A1 | 6/2013 | Paty et al. |
| 2013/0178731 A1 | 7/2013 | Bosl |
| 2013/0184603 A1 | 7/2013 | Rothman |
| 2013/0184792 A1 | 7/2013 | Simon et al. |
| 2013/0262357 A1 | 10/2013 | Amarasingham et al. |
| 2013/0267441 A1 | 10/2013 | Momeni et al. |
| 2014/0006319 A1 | 1/2014 | Anand et al. |
| 2014/0052474 A1 | 2/2014 | Madan et al. |
| 2014/0063236 A1 | 3/2014 | Shreve |
| 2014/0074848 A1 | 3/2014 | Kettunen et al. |
| 2014/0122109 A1 | 5/2014 | Ghanbari et al. |
| 2014/0141983 A1 | 5/2014 | Singh et al. |
| 2014/0219986 A1 | 8/2014 | Greene et al. |
| 2014/0279746 A1 | 9/2014 | De et al. |
| 2014/0304200 A1 | 10/2014 | Wall |
| 2014/0336539 A1 | 11/2014 | Torres et al. |
| 2015/0004588 A1 | 1/2015 | Vats et al. |
| 2015/0006192 A1 | 1/2015 | Sudharsan et al. |
| 2015/0080671 A1 | 3/2015 | Christensen et al. |
| 2015/0099946 A1 | 4/2015 | Sahin |
| 2015/0119437 A1 | 4/2015 | Clark et al. |
| 2015/0154372 A1 | 6/2015 | Soenksen et al. |
| 2015/0197543 A1 | 7/2015 | Glass et al. |
| 2015/0315182 A1 | 11/2015 | Lee et al. |
| 2016/0046990 A1 | 2/2016 | Hensel |
| 2016/0135706 A1 | 5/2016 | Sullivan et al. |
| 2016/0140859 A1 | 5/2016 | Jiao et al. |
| 2016/0180248 A1 | 6/2016 | Regan |
| 2016/0203280 A1 | 7/2016 | Neville |
| 2016/0209428 A1 | 7/2016 | Naviaux et al. |
| 2016/0342756 A1 | 11/2016 | Wall |
| 2016/0357924 A1 | 12/2016 | Jenkins |
| 2017/0035792 A1 | 2/2017 | Montagnier et al. |
| 2017/0069216 A1 | 3/2017 | Vaughan et al. |
| 2017/0091423 A1 | 3/2017 | Kumar et al. |
| 2017/0160878 A1 | 6/2017 | Endo et al. |
| 2017/0262609 A1 | 9/2017 | Perlroth et al. |
| 2018/0098724 A1 | 4/2018 | Lu et al. |
| 2018/0184964 A1 | 7/2018 | Simon et al. |
| 2018/0366144 A1 | 12/2018 | Ashoori et al. |
| 2019/0019581 A1 | 1/2019 | Vaughan et al. |
| 2019/0038202 A1 | 2/2019 | Wall |
| 2019/0043610 A1 | 2/2019 | Vaughan |
| 2019/0043618 A1 | 2/2019 | Vaughan et al. |
| 2019/0043619 A1 | 2/2019 | Vaughan et al. |
| 2019/0088366 A1 | 3/2019 | Vaughan et al. |
| 2019/0244127 A1 * | 8/2019 | Amado ............... G09B 7/02 |
| 2021/0133509 A1 * | 5/2021 | Wall ............... G06N 20/00 |

FOREIGN PATENT DOCUMENTS

| | | |
|---|---|---|
| CN | 101821741 A | 9/2010 |
| CN | 102971755 A | 3/2013 |
| CN | 103473631 A | 12/2013 |
| CN | 104254863 A | 12/2014 |
| CN | 104427932 A | 3/2015 |
| CN | 104956391 A | 9/2015 |
| EP | 0424869 | 2/1991 |
| JP | 2001034688 A | 2/2001 |
| JP | 2007249878 A | 9/2007 |
| JP | 2015228202 A | 12/2015 |
| WO | WO-9521419 A1 | 8/1995 |
| WO | WO-9705553 A1 | 2/1997 |
| WO | WO-2013062937 A2 | 5/2013 |
| WO | WO-2017106770 A1 | 6/2017 |
| WO | WO-2018090009 A1 | 5/2018 |
| WO | WO-2018148365 A1 | 8/2018 |

OTHER PUBLICATIONS

Hamidpour, et al., Antipurinergic therapy with Suramin as a treatment for autism spectrum disorder, Journal of Biomedical sciences, Mar. 29, 2016; 5:p. 17; abstract, p. 1, p. 2, p. 4, p. 5.

(56) References Cited

OTHER PUBLICATIONS

Mayes et al., Autism and ADHD: Overlapping and discriminating symptoms. Research in Autism Spectrum Disorders 6(1) :277-285 (2012).
Ogden, et al., Suramin as a chemosensitizer: Oral pharmacokinetics in rats, Pharmaceutical research, Nov. 2004;21:2058-2063; p. 2058.
PCT/US2020/049492 International Search Report and Written Opinion dated Dec. 10, 2020.
PCT/US2020/053611 International Search Report and Written Opinion dated Dec. 21, 2020.
U.S. Appl. No. 16/010,284 Non-Final Office Action dated Feb. 4, 2021.
U.S. Appl. No. 16/155,758 Final Office Action dated Jan. 12, 2021.
U.S. Appl. No. 16/155,798 Non-Final Office Action dated Apr. 9, 2020.
European Patent Application No. 1781068003 Extended European Search Report dated Dec. 11, 2019.
U.S. Appl. No. 15/589,877 Final Office Action dated Jan. 17, 2020.
U.S. Appl. No. 16/155,794 Non-Final Office Action dated Apr. 1, 2021.
U.S. Appl. No. 17/180,473 Non-Final Office Action dated Apr. 19, 2021.
Bailey, et al. Autism as a strongly genetic disorder: evidence from a British twin study. Psychol Med. Jan. 1995;25(1):63-77.
Bernier, et al. Psychopathology, families, and culture: autism. Child Adolesc Psychiatr Clin N Am. Oct. 2010;19(4):855-67.
Berument, et al. Autism screening questionnaire: diagnostic validity. Br J Psychiatry. Nov. 1999; 175:444-51.
Breiman et al.: Chapter 6 Medical diagnosis and prognosis. Classification and regression trees. Chappman & Hall/CRC (1984) (pp. 174-346).
Breiman. Random Forests. Machine Learning 45:5-32 (2001).
Brewer et al., Pinteresce: Exploring Reminiscence as an Incentive to Digital Reciprocity for Older Adults. CSCW'15 Companion (2015).
Cicchetti, et al. Reliability of the ADI-R: multiple examiners evaluate a single case. J Autism Dev Disord. Apr. 2008;38(4):764-70. Epub Dec. 5, 2007.
Cohen. Fast effective rule induction. Proceedings of the Twelfth International Conference on Machine Learning, (pp. 115-123) (1995).
Duda, et al. Clinical Evaluation of a Novel and Mobile Autism Risk Assessment. J Autism Dev Disord. Jun. 2016;46(6):1953-61.
Duda, et al. Testing the accuracy of an observation-based classifier for rapid detection of autism risk Transl Psychiatry. Aug. 12, 2014;4:e424.
Duda, et al. Testing the accuracy of an observation-based classifier for rapid detection of autism risk. Transl Psychiatry. Apr. 28, 2015;5:e556.
Duda et al., Use of Machine Learning for Behavioral Distinction of Autism and ADHD. Transl Psychiatry 6(2):e732 (2016).
Elder et al., Clinical impact of early diagnosis of autism on the prognosis and parent-child relationships. Psychology Research and Behavior Management 10: 283-292 (2017).
EP12844474.2. Search Report and Search Opinion dated Jun. 26, 2015.
European Patent Application No. 16876856.2 Examination Search Report dated Jul. 15, 2019.
European Patent Application No. 17869145.7 Supplementary Search Report dated May 4, 2020.
Fischbach, et al. The Simons Simplex Collection: a resource for identification of autism genetic risk factors. Neuron. Oct. 21, 2010;68(2): 192-5.
Fisher et al., DISC Interviewer Manual. Section 2 Computerized Versions of the DISC (2006).
Frank, et al. A simple approach to ordinal prediction. European conference on Maching Learning; Freiburg, Germany, Springer-Verlag 2001:145-156.
Frank, et al. Data mining in bioinformatics using Weka. Bioinformatics. Oct. 12, 2004;20(15):2479-81. Epub Apr. 8, 2004.
Frank et al. Generating accurate rule sets without global optimization. In: Machine Learning: Proceedings of the Fifteenth International Conference: 1998; San Francisco, CA, Morgan Kaufmann Publishers (8 pgs).
Freund, et al. A decision-theoretic generalization of on-line learning and an application to boosting. Journal of computer and system sciences 55.1 (1997): 119-139.
Freund, et al. Experiments with a new boosting algorithm. In: Proceedings of the International Conference on Machine Learning: 1996, San Francisco, Morgan Kautinann: pp. 148-156.
Freund, et al. The alternating decision tree learning algorithm. In: Machine Learning: Proceedings of the Sixteenth International Conference. 1999, pp. 124-133.
Fusaro, et al. The potential of accelerating early detection of autism through content analysis of YouTube videos. PLoS One. Apr. 16, 2014;9(4):e93533.
Gaines, et al. Induction of ripple-down rules applied to modeling large databases. Journal of Intelligent Information Systems 5.3 (1995): 211-228.
GAMA. Functional trees. Machine Learning 55:219-250 (2004).
Geschwind et al. The autism genetic resource exchange: a resource for the study of autism and related neuropsychiatric conditions. The American Journal of Human Genetics 69:463-466 (2001).
Gillberg et al. Early detection of autism. Diagnostic instruments for clinicians. European Child & Adolescent Psychiatry 5.2:67-74. (1996).
Golarai, G et al. Autism and the development of face processing. Clinical Neuroscience Research 6:145-160 (2006).
Gotham, et al. The Autism Diagnostic Observation Schedule: revised algorithms for improved diagnostic validity. J Autism Dev Disord. Apr. 2007;37(4):613-27. Epub Dec. 16, 2006.
Gura, et al. Autism spectrum disorder screening in primary care. J Dev Behav Pediatr. Jan. 2011;32(1):48-51.
Hall et al. The WEKA data mining software: an update. SIGKDD Explorations Newsletter 11:10-18(2009).
Hirsch, S et al. Development of a questionnaire weighted scoring system to target diagnostic examinations for asthma in adults: a modelling study. BMC Fam. Pract. 5:30 pp. 1-13 (2004) [E-pub Dec. 17, 2004].
Holmes et al. Multiclass alternating decision trees. Machine learning: ECML 2002. Springer Berlin Heidelberg, (pp. 161-172) (2002).
Holte. Very simple classification rules perform well on most commonly used datasets. Machine learning 11:63-91 (1993).
Howlin. Chapter 3—Identifying and assessing children with autism or asperger syndrome. Children with Autism and Asperger's Syndrome: A Guide for Practitioners and Carers. UK: John Wiley and Sons (1998) (pp. 52-75, 294-321).
Kobak et al. Web-based training in early autism screening: results from a pilot study. Telemed J E Health. Oct. 2011;17(8):640-4.
Kohavi. A study of cross-validation and bootstrap for accuracy estimation and model selection. In: Proceedings IJCAI-95: 1995: Montreal, Morgan Kaufmann, Los Altos, CA: 1137-1143.
Kosmicki, et al. Searching for a minimal set of behaviors for autism detection through feature selection-based machine learning. Transl Psychiatry. Feb. 24, 2015;5:e514.
Landwehr et al. Logistic model trees. Machine Learning 59:161-205 (2005).
Lee et al., How to Create Suitable Augmented Reality Application to Teach Social Skills for Children with ASD. IntechOpen 76476: 119-138 (2018).
Lord et al. Autism Diagnostic Interview-Revised: A revised version of a diagnostic interview for caregivers of individuals with possible pervasive developmental disorders. J Autism Dev Discord 24(5):659-685 (1994).
Lord, et al. Autism diagnostic observation schedule: a standardized observation of communicative and social behavior. J Autism Dev Disord. Jun. 1989;19(2):185-212.
Lord et al. The Autism Diagnostic Observation Schedule—Generic: A Standard Measure of Social and Communication Deficits Associated with the Spectrum of Autism. J Autism Dev Discord 30(3):205-223 (2000).

(56) References Cited

OTHER PUBLICATIONS

Martin. Instance-Based learning: Nearest neighbor with generalization. Hamilton, New Zealand, University of Waikato (83 pgs) (1995).

Moore et al. Cached Sufficient Statistics for Efficient Machine Learning with Large Datasets. JAIR 8:67-91 (1998).

Muangnak et al. Classification students with learning disabilities using naive bayes classifier and decision tree. The 6th International Conference on Networked Computing and Advanced Information Management. IEEE, 2010.

Ordonez, C et al. Machine learning techniques applied to the determination of osteoporosis incidence in post-menopausal women. Mathematical and Computer Modelling, 50:673-679 (2009).

PCT/US2012/061422 International Search Report and Written Opinion dated May 24, 2013.

PCT/US2016/046557 International Search Report and Written Opinion dated Nov. 3, 2016.

PCT/US2016/067358 International Preliminary Report on Patentability dated Jun. 28, 2018.

PCT/US2016/067358 International Search Report and Written Opinion dated Apr. 13, 2017.

PCT/US2017/061552 International Search Report and Written Opinion dated Mar. 26, 2018.

PCT/US2018/017354 International Preliminary Reporton Patentability dated Aug. 13, 2019.

PCT/US2018/017354 International Search Report and Written Opinion dated Apr. 26, 2018.

PCT/US2020/024029 International Search Report and Written Opinion dated Jul. 30, 2020.

Pinto-Martin, et al. Screening strategies for autism spectrum disorders in pediatric primary care. J Dev Behav Pediatr. Oct. 2008;29(5):345-50.

Pisula, E. Parents of children with autism: review of current research. Arch Psychiatry Psychother, 2003, 5: 51-63.

Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, The Netherlands, Jul. 16, 2015; http://ceur-ws.org/Vol-1565/(Year: 2015).

Planjner, Slide presentation on Bayesian Network Models for Adaptive Testing: Proceeding of the Twelfth Bayesian Modeling Applications Workshop (2015).

Quinlan. C4. 5: Programming for machine learning. Morgan Kaufmann (6 pgs) (1993).

Risi, et al. Combining information from multiple sources in the diagnosis of autism spectrum disorders. Journal of the American Academy of Child & Adolescent Psychiatry, 2006, 45(9): 1094-1103.

Robins, et al. The Modified Checklist for Autism in Toddlers: an initial study investigating the early detection of autism and pervasive developmental disorders. J Autism Dev Disord. Apr. 2001;31(2):131-44.

Rutter et al. Autism diagnostic interview—revised. Los Angeles, CA: Western Psychological Services 29:30 (2003).

Santosh et al. The construction and validation of a short form of the developmental, diagnostic and dimensional interview. Eur Child Adolesc Psychiatry. Aug. 2009;18(8):521-4.

Shattuck, et al. Timing of identification among children with an autism spectrum disorder: findings from a population-based surveillance study. J Am Acad Child Adolesc Psychiatry. May 2009;48(5):474-83.

Shi. Best-first decision tree learning. Master Thesis, The University of Waikato (120 pgs) (2007).

Skuse et al. The developmental, dimensional and diagnostic interview (3di): a novel computerized assessment for autism spectrum disorders. Journal of the American Academy of Child & Adolescent Psychiatry 43.5:548-558 (2004).

Tadevosyan-Leyfer, et al. A principal components analysis of the Autism Diagnostic Interview-Revised. J Am Acad Child Adolesc Psychiatry. Jul. 2003;42(7):864-72.

U.S. Appl. No. 16/155,794 Office Action dated Aug. 15, 2019.
U.S. Appl. No. 16/155,798 Office Action dated Jul. 29, 2019.
U.S. Appl. No. 15/234,814 Non-Final Office Action dated Mar. 24, 2020.
U.S. Appl. No. 15/234,814 Office Action dated Oct. 3, 2019.
U.S. Appl. No. 16/155,758 Non-Final Office Action dated Jul. 7, 2020.
U.S. Appl. No. 16/155,761 Non-Final Office Action dated Apr. 2, 2020.
U.S. Appl. No. 16/155,761 Office Action dated Oct. 7, 2019.
U.S. Appl. No. 16/155,794 Non-Final Office Action dated Apr. 16, 2020.
U.S. Appl. No. 14/354,032 Notice of Allowance dated Apr. 13, 2016.
U.S. Appl. No. 14/354,032 Notice of Allowance dated Jun. 14, 2016.
U.S. Appl. No. 14/354,032 Office Action dated Jul. 28, 2015.
U.S. Appl. No. 15/234,814 Non-Final Office Action dated Jun. 7, 2018.
U.S. Appl. No. 15/234,814 Office Action dated Jan. 18, 2019.
U.S. Appl. No. 16/155,758 Preinterview First Office Action dated Feb. 8, 2019.
U.S. Appl. No. 16/155,761 Preinterview First Office Action dated Jan. 9, 2019.
U.S. Appl. No. 16/155,794 Office Action dated Jan. 14, 2019.
U.S. Appl. No. 16/157,787 Office Action dated Mar. 27, 2019.

Van Stralen et al. Diagnostic methods I: sensitivity, specificity, and other measures of accuracy. Kidney Int. 75(12):1257-1263 (2009).

Wall et al. Use of artificial intelligence to shorten the behavioral diagnosis of autism. PLoS One. 2012;7(8):e43855.

Wall, et al. Use of machine learning to shorten observation-based screening and diagnosis of autism. Transl Psychiatry. Apr. 10, 2012;2:e100.

Wenner, M. Gut Bacteria May Playa Role in Autism. Scientific American, pp. 1-4, Sep. 1, 2014.

Wiggins, et al. Examination of the time between first evaluation and first autism spectrum diagnosis in a population-based sample. J Dev Behav Pediatr. Apr. 2006;27(2 Suppl):S79-87.

Witten et al. Data Mining: Practical Machine Learning Tools and Techniques with Java Implementations. Morgan Kaufmann, Amsterdam, Second Edition (558 pgs) (Oct. 2005).

\* cited by examiner

MODEL OPTIMIZATION AND DATA ANALYSIS USING MACHINE LEARNING TECHNIQUES

CROSS REFERENCE TO RELATED APPLICATIONS

This application is a continuation of International Application No. PCT/US2020/024029, filed Mar. 20, 2020, which claims the benefit of U.S. Provisional Application Ser. No. 62/822,186, filed Mar. 22, 2019, the contents of which are incorporated by reference herein in its entirety.

BACKGROUND

Many people suffer from cognitive disorders, developmental delays, and neurologic impairments. Using traditional diagnostic and treatment methods, these conditions are difficult to diagnose and treat.

SUMMARY OF THE INVENTION

Described herein are platforms, systems, devices, methods and media for diagnosing and treating individuals having one or more diagnoses from the related groups of conditions comprising cognitive disorders, developmental delays, and neurologic impairments.

Non-limiting examples of cognitive disorders and developmental delays include autism, autistic spectrum, attention deficit disorder, attention deficit hyperactive disorder and speech and learning disability. Non-limiting examples of neurologic impairments include cerebral palsy and neurodegenerative disease. These groups of related conditions comprising cognitive disorders, developmental delays, and neurologic impairments are related in the sense that individuals may demonstrate symptoms or behaviors that would be classified under more than one of these groups of conditions and often individuals have multiple of these conditions. As such, it is difficult to accurately distinguish between a diagnoses that have multiple states along a spectrum of disease (e.g. autism spectrum disorder). As such, it is difficult to distinguish between diagnoses that have overlapping symptoms (e.g. autism and ADHD).

Current methods for diagnosing and treating cognitive disorders, developmental delays, and neurologic impairments experience a bottleneck in terms of the information that is utilized during the diagnostic process and what is made available for determining the therapy. For example, an individual may be given a categorical diagnosis as having autism spectrum disorder and then provided with a general purpose treatment regimen based on the diagnosis. Information that may be relevant to specific impairments such as, for example, degree of ability to recognize emotional cues based on facial expression, may be absent during when determining the appropriate therapy.

Accordingly, disclosed herein are platforms, systems, devices, methods, and media that provide a technical solution to this long-standing problem by incorporating diagnostic data into the therapeutic design. Instead of providing a general diagnosis that places a patient in one of a few categorical buckets followed by a general treatment, often by a different healthcare provider, the diagnostic or evaluation process can be combined with a therapeutic process that incorporates the multi-dimensional space from the evaluation or diagnosis for purposes of customizing the therapeutic on a case by case basis.

In some instances, a single user account is provided that contains both diagnostic and therapeutic information, thus linking user information to both processes. This combined approach helps ensure that no potentially relevant information is left out when making the diagnosis or determining the appropriate therapeutic regimen. By bridging the diagnostic and therapeutic onto the same platform or process, a network and/or synergistic effect can be achieved. For example, the therapy can be customized to account for specific dimensions relating to emotion recognition that is used to determine that the subject would benefit from emotion recognition detection therapy using an augmented reality tool, or even specific activities with the tool that are predicted to work better than other similar activities.

The internal diagnostic dimensions that are computed based on input data during the diagnostic process can be preserved and then transferred into the therapeutic process for use in identifying the optimal treatment. Thus, the patient's position within the multi-dimensional space (a dimension being a nonlinear combination of input features) generated by the diagnostic process can be analyzed by a therapeutic model to determine or identify one or more specific therapies predicted to offer (improved) therapeutic efficacy.

Accordingly, the digital therapeutic can be customized on a case by case basis based on the multi-dimensional feature set that is computed during the application of the digital diagnostic or evaluation of the same subject. This approach provides a unique ability to apply precision digital therapeutics that are more efficient and more effective compared to the conventional approach in the therapy plan is based on a categorical diagnosis rather than a fine-granular understanding of the particular presentation of the condition in particular cases.

The methods and devices disclosed herein are configured to determine a cognitive function attribute such as, for example, the developmental progress of a subject in a clinical or nonclinical environment. For example, the described methods and devices can identify a subject as developmentally advanced in one or more areas of development, or identify a subject as developmentally delayed or at risk of having one or more developmental disorders.

The methods and devices disclosed can determine the subject's developmental progress by evaluating a plurality of characteristics or features of the subject based on an assessment model, wherein the assessment model can be generated from large datasets of relevant subject populations using machine-learning approaches. The methods and devices disclosed herein comprise improved logical structures and processes to diagnose a subject with a disorder among a plurality of disorders using one or more machine learning models.

The identification and treatment of cognitive function attributes, including for example, developmental disorders in subjects can present a daunting technical problem in terms of both accuracy and efficiency. Many known methods for identifying such attributes or disorders are often time-consuming and resource-intensive, requiring a subject to answer a large number of questions or undergo extensive observation under the administration of qualified clinicians, who may be limited in number and availability depending on the subject's geographical location.

In addition, many known methods for identifying and treating related behavioral, neurological, or mental health conditions or disorders have less than ideal accuracy and consistency because of the interrelatedness of the plurality of diseases within the related categories of behavioral disorders, developmental delays, and neurologic impairments. Further, many subjects may have two or more related disorders or conditions. If each test is designed to diagnose or identify only a single disorder or condition, a subject presenting with multiple disorders may be required to take multiple tests. The evaluation of a subject using multiple diagnostic tests may be lengthy, expensive, inconvenient, and logistically challenging to arrange. It would be desirable to provide a way to test a subject using a single diagnostic test that is capable of identifying or diagnosing multiple related disorders or conditions with sufficient sensitivity and specificity.

Described herein is a technical solution to such a technical problem, wherein the technical solution improves both the accuracy and efficiency of existing methods. Such a technical solution reduces the required time and resources for administering a method for identifying and treating attributes of cognitive function, such as behavioral, neurological or mental health conditions or disorders, and improves the accuracy and consistency of the identification outcomes across subjects.

Additionally, disclosed herein are methods and treatments that can be applied to subjects to advance cognitive function for subjects with advanced, normal and decreased cognitive function. In light of the above, improved methods and systems of diagnosing and identifying subjects at risk for a particular cognitive function attribute such as a developmental disorder and for providing improved digital therapeutics are needed. Ideally such methods and devices would require fewer questions, decreased amounts of time, determine a plurality of cognitive function attributes, such as behavioral, neurological or mental health conditions or disorders, and provide clinically acceptable sensitivity and specificity in a clinical or nonclinical environment, which can be used to monitor and adapt treatment efficacy. Moreover, improved digital therapeutics can provide a customized treatment plan for a patient, receive updated diagnostic data in response to the customized treatment plan to determine progress, and update the treatment plan accordingly. Such methods and devices can also be used to determine the developmental progress of a subject, and offer treatment to advance developmental progress.

The methods and devices disclosed herein can diagnose or identify a subject at risk of having one or more cognitive function attributes such as for example, a subject at risk of having one or more developmental disorders among a plurality of related developmental disorders in a clinical or nonclinical setting, with fewer questions, in a decreased amounts of time, and with clinically acceptable sensitivity and specificity in a clinical environment. A processor can be configured with instructions to identify a most predictive next question, such that a person can be diagnosed or identified as at risk with fewer questions. Identifying the most predictive next question in response to a plurality of answers has the advantage of increasing the sensitivity and the specificity with fewer questions. The methods and devices disclosed herein can be configured to evaluate a subject for a plurality of related developmental disorders using a single test, and diagnose or determine the subject as at risk of one or more of the plurality of developmental disorders using the single test. Decreasing the number of questions presented can be particularly helpful where a subject presents with a plurality of possible developmental disorders. Evaluating the subject for the plurality of possible disorders using just a single test can greatly reduce the length and cost of the evaluation procedure. The methods and devices disclosed herein can diagnose or identify the subject as at risk for having a single developmental disorder among a plurality of possible developmental disorders that may have overlapping symptoms.

While the most predictive next question can be determined in many ways, in many instances the most predictive next question is determined in response to a plurality of answers to preceding questions that may comprise prior most predictive next questions. The most predictive next question can be determined statistically, and a set of possible most predictive next questions evaluated to determine the most predictive next question. In many instances, answers to each of the possible most predictive next questions are related to the relevance of the question, and the relevance of the question can be determined in response to the combined feature importance of each possible answer to a question.

The methods and devices disclosed herein can categorize a subject into one of three categories: having one or more developmental conditions, being developmentally normal or typical, or inconclusive (i.e. requiring additional evaluation to determine whether the subject has any developmental conditions). A developmental condition can be a developmental disorder or a developmental advancement. Note that the methods and devices disclosed herein are not limited to developmental conditions, and may be applied to other cognitive function attributes, such as behavioral, neurological or mental health conditions. The methods and devices may initially categorize a subject into one of the three categories, and subsequently continue with the evaluation of a subject initially categorized as "inconclusive" by collecting additional information from the subject. Such continued evaluation of a subject initially categorized as "inconclusive" may be performed continuously with a single screening procedure (e.g., containing various assessment modules). Alternatively or additionally, a subject identified as belonging to the inconclusive group may be evaluated using separate, additional screening procedures and/or referred to a clinician for further evaluation.

The methods and devices disclosed herein can evaluate a subject using a combination of questionnaires and video inputs, wherein the two inputs may be integrated mathematically to optimize the sensitivity and/or specificity of classification or diagnosis of the subject. Optionally, the methods and devices can be optimized for different settings (e.g., primary vs secondary care) to account for differences in expected prevalence rates depending on the application setting.

The methods and devices disclosed herein can account for different subject-specific dimensions such as, for example, a subject's age, a geographic location associated with a subject, a subject's gender or any other subject-specific or demographic data associated with a subject. In particular, the methods and devices disclosed herein can take different subject-specific dimensions into account in identifying the subject as at risk of having one or more cognitive function attributes such as developmental conditions, in order to increase the sensitivity and specificity of evaluation, diagnosis, or classification of the subject. For example, subjects belonging to different age groups may be evaluated using different machine learning assessment models, each of which can be specifically tuned to identify the one or more developmental conditions in subjects of a particular age group. Each age group-specific assessment model may contain a unique group of assessment items (e.g., questions, video observations), wherein some of the assessment items may overlap with those of other age groups' specific assessment models.

In addition, the digital personalized medicine systems and methods described herein can provide digital diagnostics and digital therapeutics to patients. The digital personalized medicine system can use digital data to assess or diagnose symptoms of a patient in ways that inform personalized or more appropriate therapeutic interventions and improved diagnoses.

In one aspect, the digital personalized medicine system can comprise digital devices with processors and associated software that can be configured to: use data to assess and diagnose a patient; capture interaction and feedback data that identify relative levels of efficacy, compliance and response resulting from the therapeutic interventions; and perform data analysis. Such data analysis can include artificial intelligence, including for example machine learning, and/or statistical models to assess user data and user profiles to further personalize, improve or assess efficacy of the therapeutic interventions.

In some instances, the system can be configured to use digital diagnostics and digital therapeutics. Digital diagnostics and digital therapeutics, in some embodiments, together comprise a device or methods for digitally collecting information and processing and evaluating the provided data to improve the medical, psychological, or physiological state of an individual. A digital therapeutic system can apply software based learning to evaluate user data, monitor and improve the diagnoses and provide therapeutic interventions. In some embodiments, a digital therapy is configured to improve social reciprocity in individuals with autism or autism spectrum disorder by helping them identify expressions of emotion in real time while they interact with a person or a virtual image that expresses the emotion.

Digital diagnostics data in the system can comprise data and meta-data collected from the patient, or a caregiver, or a party that is independent of the assessed individual. In some instances, the collected data can comprise monitoring behaviors, observations, judgments, or assessments made by a party other than the individual. In further instances, the assessment can comprise an adult performing an assessment or provide data for an assessment of a child or juvenile. The data and meta-data can be either actively or passively collected in digital format via one or more digital devices such as mobile phones, video capture, audio capture, activity monitors, or wearable digital monitors.

The digital diagnostic uses the data collected by the system about the patient, which can include complimentary diagnostic data captured outside the digital diagnostic, with analysis from tools such as machine learning, artificial intelligence, and statistical modeling to assess or diagnose the patient's condition. The digital diagnostic can also provide an assessment of a patient's change in state or performance, directly or indirectly via data and meta-data that can be analyzed and evaluated by tools such as machine learning, artificial intelligence, and statistical modeling to provide feedback into the system to improve or refine the diagnoses and potential therapeutic interventions.

Data assessment and machine learning from the digital diagnostic and corresponding responses, or lack thereof, from the therapeutic interventions can lead to the identification of novel diagnoses for patients and novel therapeutic regimens for both patents and caregivers.

Types of data collected and utilized by the system can include patient and caregiver video, audio, responses to questions or activities, and active or passive data streams from user interaction with activities, games or software features of the system, for example. Such data can also include meta-data from patient or caregiver interaction with the system, for example, when performing recommended activities. Specific meta-data examples include data from a user's interaction with the system's device or mobile app that captures aspects of the user's behaviors, profile, activities, interactions with the software system, interactions with games, frequency of use, session time, options or features selected, and content and activity preferences. Data can also include data and meta-data from various third party devices such as activity monitors, games or interactive content.

In some embodiments, disclosed herein is a personalized treatment regimen comprising digital therapeutics, non-digital therapeutics, pharmaceuticals, or any combination thereof. Digital therapeutics can comprise instructions, feedback, activities or interactions provided to the patient or caregiver by the system. Examples include suggested behaviors, activities, games or interactive sessions with system software and/or third party devices. The digital therapeutics can be implemented using various methods, including augmented reality, real-time cognitive assistance, virtual reality, or other behavioral therapies augmented using technology. In some instances, the digital therapeutics are implemented using artificial intelligence. For example, an artificial intelligence-driven wearable device can be used to provide behavioral intervention to improve social outcomes for children with behavioral, neurological or mental health conditions or disorders. In some embodiments, the personalized treatment regimen is adaptive, for example, dynamically updating or reconfiguring its therapies based on captured feedback from the subject during ongoing therapy and/or additional relevant information (e.g., results from an autism evaluation).

In further aspects, the digital therapeutics methods and systems disclosed herein can diagnose and treat a subject at risk of having one or more behavioral, neurological or mental health conditions or disorders among a plurality of behavioral, neurological or mental health conditions or disorders in a clinical or nonclinical setting. This diagnosis and treatment can be accomplished using the methods and systems disclosed herein with fewer questions, in a decreased amount of time, and with clinically acceptable sensitivity and specificity in a clinical environment, and can provide treatment recommendations. This can be helpful when a subject initiates treatment based on an incorrect diagnosis, for example. A processor can be configured with instructions to identify a most predictive next question or most instructive next symptom or observation such that a person can be diagnosed or identified as at risk reliably using only the optimal number of questions or observations. Identifying the most predictive next question or most instructive next symptom or observation in response to a plurality of answers has the advantage of providing treatment with fewer questions without degrading the sensitivity or specificity of the diagnostic process. In some instances, an additional processor can be provided to predict or collect information on the next more relevant symptom. The methods and devices disclosed herein can be configured to evaluate and treat a subject for a plurality of related disorders using a single adaptive test, and diagnose or determine the subject as at risk of one or more of the plurality of disorders using the single test. Decreasing the number of questions presented or symptoms or measurements used can be particularly helpful where a subject presents with a plurality of possible disorders that can be treated. Evaluating the subject for the plurality of possible disorders using just a single adaptive test can greatly reduce the length and cost of the evaluation procedure and improve treatment. The methods and devices disclosed herein can diagnose and treat subject at risk for having a single disorder among a plurality of possible disorders that may have overlapping symptoms.

The most predictive next question, most instructive next symptom or observation used for the digital therapeutic treatment can be determined in many ways. In many instances, the most predictive next question, symptom, or observation can be determined in response to a plurality of answers to preceding questions or observation that may comprise prior most predictive next question, symptom, or observation to evaluate the treatment and provide a closed-loop assessment of the subject. The most predictive next question, symptom, or observation can be determined statistically, and a set of candidates can be evaluated to determine the most predictive next question, symptom, or observation. In many instances, observations or answers to each of the candidates are related to the relevance of the question or observation, and the relevance of the question or observation can be determined in response to the combined feature importance of each possible answer to a question or observation. Once a treatment has been initiated, the questions, symptoms, or observations can be repeated or different questions, symptoms, or observations can be used to more accurately monitor progress and suggest changes to the digital treatment. The relevance of a next question, symptom or observation can also depend on the variance of the ultimate assessment among different answer choices of the question or potential options for an observation. For example, a question for which the answer choices might have a significant impact on the ultimate assessment down the line can be deemed more relevant than a question for which the answer choices might only help to discern differences in severity for one particular condition, or are otherwise less consequential.

An Exemplary Device

Described herein is a platform for assessing and providing treatment to an individual with respect to a behavioral disorder, a developmental delay, or a neurologic impairment, said platform comprising a computing device comprising: a processor; a non-transitory computer-readable medium that stores a computer program configured to cause said processor to: (a) receive an input for said individual related to said behavioral disorder said developmental delay, or said neurologic impairment; (b) determine that said individual has an indication of a presence of said behavioral disorder, said developmental delay, or said neurologic impairment using a trained classifier module of said computer program that is trained using data from a plurality of individuals having said behavioral disorder, said developmental delay, or said neurologic impairment; (c) determine using a machine learning model, that is generated by said computer program, that said behavioral disorder, said developmental delay, or said neurologic impairment that said individual has said indication of said presence will be improved by a digital therapy that promotes social reciprocity; and (d) provide a digital therapy that promotes social reciprocity.

In some embodiments, said machine learning model determines a degree improvement that will be achieved by said digital therapy.

In some embodiments, said behavioral disorder, said developmental delay, or said neurologic impairment is autism or autism spectrum disorder.

In some embodiments, said processor is configured with further instructions to provide said digital therapy to said individual when it is determined that said autism or said autism spectrum disorder will be improved by said digital therapy.

In some embodiments, said digital therapy comprises an augmented reality experience In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, said processor is configured with further instructions to obtain a video or an image of a person interacted with by said individual in said augmented reality experience with a camera of said mobile computing device.

In some embodiments, said processor is configured with further instructions to determine an emotion associated with said person using an image analysis module to analyze said video or said image.

In some embodiments, said virtual reality experience comprises a displayed virtual person or character and said device further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output of said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, said processor is configured with further instructions to categorize a sound from said microphone as associated with an emotion.

In some embodiments, said processor is configured with further instructions to provide instructions with said digital therapy for said individual to engage in an activity mode.

In some embodiments, said activity mode comprises an emotion elicitation activity, an emotion recognition activity, or unstructured play.

In some embodiments, a therapeutic agent is provided to said individual together with said digital therapy.

In some embodiments, said therapeutic agent improves a cognition of said individual while said individual receives said digital therapy.

In some embodiments, said device is a wearable device.

In some embodiments, said platform comprises a video analyst portal allowing a video analyst to review one or more videos captured and uploaded using the computing device and upload a portion of said input.

In some embodiments, said platform comprises a healthcare provider portal allowing a healthcare provider to upload a portion of said input.

Another Exemplary Device

In some aspects, disclosed herein is a device for assessing and providing treatment to an individual with respect to a behavioral disorder, a developmental delay, or a neurologic impairment, said device comprising: a processor; a non-transitory computer-readable medium that stores a computer program configured to cause said processor to: (a) receive an input for said individual related to said behavioral disorder said developmental delay, or said neurologic impairment; (b) determine that said individual has an indication of a presence of said behavioral disorder, said developmental delay, or said neurologic impairment using a trained classifier module of said computer program that is trained using data from a plurality of individuals having said behavioral disorder, said developmental delay, or said neurologic impairment; (c) determine using a machine learning model, that is generated by said computer program, that said behavioral disorder, said developmental delay, or said neurologic impairment that said individual has said indication of said presence will be improved by a digital therapy that promotes social reciprocity; and (d) provide a digital therapy that promotes social reciprocity.

In some embodiments, said machine learning model determines a degree improvement that will be achieved by said digital therapy.

In some embodiments, said behavioral disorder, said developmental delay, or said neurologic impairment is autism or autism spectrum disorder.

In some embodiments, said processor is configured with further instructions to provide said digital therapy to said individual when it is determined that said autism or said autism spectrum disorder will be improved by said digital therapy.

In some embodiments, said digital therapy comprises an augmented reality experience In some embodiments, said digital therapy comprises a virtual reality experience.

In some embodiments, said digital therapy is provided by a mobile computing device. In some embodiments, said mobile computing device comprises a smartphone, tablet computer, laptop, smartwatch or other wearable computing device.

In some embodiments, said processor is configured with further instructions to obtain a video or an image of a person interacted with by said individual in said augmented reality experience with a camera of said mobile computing device.

In some embodiments, said processor is configured with further instructions to determine an emotion associated with said person using an image analysis module to analyze said video or said image.

In some embodiments, said virtual reality experience comprises a displayed virtual person or character and said device further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, said processor is configured with further instructions to categorize a sound from said microphone as associated with an emotion.

In some embodiments, said processor is configured with further instructions to provide instructions with said digital therapy for said individual to engage in an activity mode.

In some embodiments, said activity mode comprises an emotion elicitation activity, an emotion recognition activity, or unstructured play.

In some embodiments, a therapeutic agent is provided to said individual together with said digital therapy.

In some embodiments, said therapeutic agent improves a cognition of said individual while said individual receives said digital therapy.

In some embodiments, said device is a wearable device.

An Exemplary Method

In some aspects, disclosed herein is a computer-implemented method for treating an individual with respect to a behavioral disorder, a developmental delay, or a neurologic impairment using a digital therapy, said method comprising: (a) receiving an input for said individual related to said behavioral disorder, said developmental delay, or said neurologic impairment; (b) determining, using a trained classifier, that said individual has an indication of having said behavioral disorder, said developmental delay, or said neurologic impairment; (c) determining, using a machine learning model, that said behavioral disorder, said developmental delay, or said neurologic impairment that said individual has an indication of having will be improved by a digital therapy that is configured to promote social reciprocity.

In some embodiments, said machine learning model determines a degree of improvement that will be achieved by said digital therapy.

In some embodiments, the method comprises providing said digital therapy to said individual when it is determined that said developmental disorder is autism or autism spectrum disorder.

In some embodiments, said digital therapy comprises an augmented reality experience In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, the method comprises obtaining a video or an image of a person interacted with by said individual in said augmented reality experience with a camera of said mobile computing device.

In some embodiments, the method comprises determining an emotion associated with said person using an image analysis module to analyze said video or said image.

In some embodiments, said virtual reality experience comprises a displayed virtual person or character and said method further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, the method comprises categorizing a sound from said microphone as associated with an emotion.

In some embodiments, the method further comprises providing instructions with said digital therapy for said individual to engage in an activity mode.

In some embodiments, said activity mode comprise an emotion elicitation activity, an emotion recognition activity, or unstructured play.

In some embodiments, the method comprises providing a therapeutic agent together with said digital therapy.

In some embodiments, said therapeutic agent improves a cognition of said individual while said individual receives said digital therapy.

In some embodiments, said digital therapy is configured to promote social reciprocity in said individual.

An Exemplary Medium

In some aspects, disclosed herein is a non-transitory computer-readable medium that stores a computer program configured to cause a processor to: (a) receive an input for said individual related to said behavioral disorder said developmental delay, or said neurologic impairment; (b) determine that said individual has an indication of a presence of said behavioral disorder, said developmental delay, or said neurologic impairment using a trained classifier module of said computer program that is trained using data from a plurality of individuals having said behavioral disorder, said developmental delay, or said neurologic impairment; (c) determine using a machine learning model, that is generated by said computer program, that said behavioral disorder, said developmental delay, or said neurologic impairment that said individual has said indication of said presence will be improved by a digital therapy that promotes social reciprocity; and (d) provide a digital therapy that promotes social reciprocity.

In some embodiments, said machine learning model determines a degree improvement that will be achieved by said digital therapy.

In some embodiments, said behavioral disorder, said developmental delay, or said neurologic impairment is autism or autism spectrum disorder.

In some embodiments, said processor is configured with further instructions to provide said digital therapy to said individual when it is determined that said autism or said autism spectrum disorder will be improved by said digital therapy.

In some embodiments, said digital therapy comprises an augmented reality experience In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, said computer-readable medium is configured with further instructions to cause said processor to obtain a video or an image of a person interacted with by said individual in said augmented reality experience with a camera of said mobile computing device.

In some embodiments, said computer-readable medium is configured with further instructions to cause said processor to determine an emotion associated with said person using an image analysis module to analyze said video or said image.

In some embodiments, said virtual reality experience comprises a displayed virtual person or character and said device further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, said computer-readable medium is configured with further instructions to cause said processor to categorize a sound from said microphone as associated with an emotion.

In some embodiments, said computer-readable medium is configured with further instructions to cause said processor to provide instructions with said digital therapy for said individual to engage in an activity mode.

In some embodiments, said activity mode comprises an emotion elicitation activity, an emotion recognition activity, or unstructured play.

In some embodiments, a therapeutic agent is provided to said individual together with said digital therapy.

In some embodiments, said therapeutic agent improves a cognition of said individual while said individual receives said digital therapy.

In some embodiments, said device is a wearable device.

Another Exemplary Method

In some aspects, disclosed herein is a computer-implemented method for treating an individual with respect to a behavioral disorder, a developmental delay, or a neurologic impairment using a digital therapy, said method comprising: (a) receiving an input for said individual related to said behavioral disorder, said developmental delay, or said neurologic impairment; (b) determining, using a trained classifier, that said individual has an indication of having said behavioral disorder, said developmental delay, or said neurologic impairment; (c) determining, using a machine learning model, that said behavioral disorder, said developmental delay, or said neurologic impairment that said individual has an indication of having will be improved by a digital therapy that is configured to promote social reciprocity.

In some embodiments, said machine learning model determines a degree of improvement that will be achieved by said digital therapy.

In some embodiments, said method comprises providing said digital therapy to said individual when it is determined that said developmental disorder is autism or autism spectrum disorder.

In some embodiments, said digital therapy comprises an augmented reality experience In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, the method comprises obtaining a video or an image of a person interacted with by said individual in said augmented reality experience with a camera of said mobile computing device.

In some embodiments, the method comprises determining an emotion associated with said person using an image analysis module to analyze said video or said image.

In some embodiments, said virtual reality experience comprises a displayed virtual person or character and said method further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, the method comprises categorizing a sound from said microphone as associated with an emotion.

In some embodiments, the method further comprises providing instructions with said digital therapy for said individual to engage in an activity mode.

In some embodiments, said activity mode comprise an emotion elicitation activity, an emotion recognition activity, or unstructured play.

In some embodiments, the method comprises providing a therapeutic agent together with said digital therapy.

In some embodiments, said therapeutic agent improves a cognition of said individual while said individual receives said digital therapy.

In some embodiments, said digital therapy is configured to promote social reciprocity in said individual.

Another Exemplary Device

In some aspects disclosed herein is a device for providing digital therapy to an individual with respect to a behavior disorder, developmental delay, or neurologic impairment, said device comprising: (a) a display; and (b) a processor configured with instructions to: (i) receive an input for said individual related to said plurality of related behavioral disorders, developmental delays, and neurologic impairments; (ii) determine, using an assessment classifier, that said individual has a diagnosis of autism or autism spectrum disorder based on said input; and (iii) determine, using a machine learning model, that said autism or said autism spectrum disorder of said individual will be improved by said digital therapy.

In some embodiments, said machine learning model determines a degree improvement that will be achieved by said digital therapy.

In some embodiments, said behavioral disorder, said developmental delay, or said neurologic impairment is autism or autism spectrum disorder.

In some embodiments, said processor is configured with further instructions to provide said digital therapy to said individual when it is determined that said autism or said autism spectrum disorder will be improved by said digital therapy.

In some embodiments, said digital therapy comprises an augmented reality experience In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, said processor is configured with further instructions to obtain a video or an image of a person interacted with by said individual in said augmented reality experience with a camera of said mobile computing device.

In some embodiments, said processor is configured with further instructions to determine an emotion associated with said person using an image analysis module to analyze said video or said image.

In some embodiments, said virtual reality experience comprises a displayed virtual person or character and said device further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, said processor is configured with further instructions to categorize a sound from said microphone as associated with an emotion.

In some embodiments, said processor is configured with further instructions to provide instructions with said digital therapy for said individual to engage in an activity mode.

In some embodiments, said activity mode comprises an emotion elicitation activity, an emotion recognition activity, or unstructured play.

In some embodiments, a therapeutic agent is provided to said individual together with said digital therapy.

In some embodiments, said therapeutic agent improves a cognition of said individual while said individual receives said digital therapy.

In some embodiments, said digital therapy is configured to promote social reciprocity in said individual.

Another Exemplary Method

In one aspect, a method of providing an evaluation of at least one cognitive function attribute of a subject may comprise: on a computer system having a processor and a memory storing a computer program for execution by the processor, the computer program comprising instructions for: receiving data of the subject related to the cognitive function attribute; evaluating the data of the subject using a machine learning model; and providing an evaluation for the subject, the evaluation selected from the group consisting of an inconclusive determination and a categorical determination in response to the data. The machine learning model may comprise a selected subset of a plurality of machine learning assessment models.

The categorical determination may comprise a presence of the cognitive function attribute and an absence of the cognitive function attribute. Receiving data from the subject may comprise receiving an initial set of data. Evaluating the data from the subject may comprise evaluating the initial set of data using a preliminary subset of tunable machine learning assessment models selected from the plurality of tunable machine learning assessment models to output a numerical score for each of the preliminary subset of tunable machine learning assessment models.

The method may further comprise providing a categorical determination or an inconclusive determination as to the presence or absence of the cognitive function attribute in the subject based on the analysis of the initial set of data, wherein the ratio of inconclusive to categorical determinations can be adjusted. The method may further comprise: determining whether to apply additional assessment models selected from the plurality of tunable machine learning assessment models if the analysis of the initial set of data yields an inconclusive determination; receiving an additional set of data from the subject based on an outcome of the decision; evaluating the additional set of data from the subject using the additional assessment models to output a numerical score for each of the additional assessment models based on the outcome of the decision; and providing a categorical determination or an inconclusive determination as to the presence or absence of the cognitive function attribute in the subject based on the analysis of the additional set of data from the subject using the additional assessment models, wherein the ratio of inconclusive to categorical determinations can be adjusted.

The method may further comprise: combining the numerical scores for each of the preliminary subset of assessment models to generate a combined preliminary output score; and mapping the combined preliminary output score to a categorical determination or to an inconclusive determination as to the presence or absence of the cognitive function attribute in the subject, wherein the ratio of inconclusive to categorical determinations can be adjusted.

The method may further comprise employing rule-based logic or combinatorial techniques for combining the numerical scores for each of the preliminary subset of assessment models and for combining the numerical scores for each of the additional assessment models. The ratio of inconclusive to categorical determinations may be adjusted by specifying an inclusion rate. The categorical determination as to the presence or absence of the developmental condition in the subject may be assessed by providing a sensitivity and specificity metric. The inclusion rate may be no less than 70% and the categorical determination may result in a sensitivity of at least 70 with a corresponding specificity of at least 70. The inclusion rate may be no less than 70% and the categorical determination may result in a sensitivity of at least 80 with a corresponding specificity of at least 80. The inclusion rate may be no less than 70% and the categorical determination may result in a sensitivity of at least 90 with a corresponding specificity of at least 90.

Data from the subject may comprise at least one of a sample of a diagnostic instrument, wherein the diagnostic instrument comprises a set of diagnostic questions and corresponding selectable answers, and demographic data.

The method may further comprise: training a plurality of tunable machine learning assessment models using data from a plurality of subjects previously evaluated for the developmental condition, wherein training comprises: pre-processing the data from the plurality of subjects using machine learning techniques; extracting and encoding machine learning features from the pre-processed data; processing the data from the plurality of subjects to mirror an expected prevalence of a cognitive function attribute among subjects in an intended application setting; selecting a subset of the processed machine learning features; evaluating each model in the plurality of tunable machine learning assessment models for performance, wherein each model is evaluated for sensitivity and specificity for a pre-determined inclusion rate; and determining an optimal set of parameters for each model based on determining the benefit of using all models in a selected subset of the plurality of tunable machine learning assessment models. Determining an optimal set of parameters for each model may comprise tuning the parameters of each model under different tuning parameter settings.

Processing the encoded machine learning features may comprise: computing and assigning sample weights to every sample of data, wherein each sample of data corresponds to a subject in the plurality of subjects, wherein samples are grouped according to subject-specific dimensions, and wherein the sample weights are computed and assigned to balance one group of samples against every other group of samples to mirror the expected distribution of each dimension among subjects in an intended setting. The subject-specific dimensions may comprise a subject's gender, the geographic region where a subject resides, and a subject's age. Extracting and encoding machine learning features from the pre-processed data may comprise using feature encoding techniques such as but not limited to one-hot encoding, severity encoding, and presence-of-behavior encoding. Selecting a subset of the processed machine learning features may comprise using bootstrapping techniques to identify a subset of discriminating features from the processed machine learning features.

The cognitive function attribute may comprise a behavioral disorder and a developmental advancement. The categorical determination provided for the subject may be selected from the group consisting of an inconclusive determination, a presence of multiple cognitive function attributes, and an absence of multiple cognitive function attributes in response to the data.

In another aspect, an apparatus to evaluate a cognitive function attribute of a subject may comprise processor configured with instructions that, when executed, cause the processor to perform the method described above.

Another Exemplary Device

In another aspect, a mobile device for providing an evaluation of at least one cognitive function attribute of a subject may comprise: a display; and a processor configured with instructions to: receive and display data of the subject related to the cognitive function attribute; and receive and display an evaluation for the subject, the evaluation selected from the group consisting of an inconclusive determination and a categorical determination; wherein the evaluation for the subject has been determined in response to the data of the subject.

The categorical determination may be selected from the group consisting of a presence of the cognitive function attribute, and an absence of the cognitive function attribute.

The cognitive function attribute may be determined with a sensitivity of at least 80% and a specificity of at least 80%, respectively, for the presence or the absence of the cognitive function attribute. The cognitive function attribute may be determined with a sensitivity of at least 90% and a specificity of at least 90%, respectively, for the presence or the absence of the cognitive function attribute. The cognitive function attribute may comprise a behavioral disorder, a developmental delay, or a neurologic impairment.

Another Exemplary Device

In another aspect, a digital therapy delivery device may include: one or more processors comprising software instructions; a diagnostic module to receive data from the subject and output diagnostic data for the subject, the diagnostic module comprising one or more classifiers built using machine learning or statistical modeling based on a subject population to determine the diagnostic data for the subject.

In some embodiments, diagnostic software employs a Triton model, wherein the diagnostic data comprises an evaluation for the subject, the evaluation selected from the group consisting of an inconclusive determination and a categorical determination in response to data received from the subject; and a therapeutic module to receive the diagnostic data and output the personal therapeutic treatment plan for the subject, the therapeutic module comprising one or more models built using machine learning or statistical modeling based on at least a portion the subject population to determine and output the personal therapeutic treatment plan of the subject, wherein the diagnostic module is configured to receive updated subject data from the subject in response to therapy of the subject and generate updated diagnostic data from the subject and wherein the therapeutic module is configured to receive the updated diagnostic data and output an updated personal treatment plan for the subject in response to the diagnostic data and the updated diagnostic data.

The diagnostic module may comprise a diagnostic machine learning classifier trained on the subject population and the therapeutic module may comprise a therapeutic machine learning classifier trained on the at least the portion of the subject population and the diagnostic module and the therapeutic module may be arranged for the diagnostic module to provide feedback to the therapeutic module based on performance of the treatment plan. The therapeutic classifier may comprise instructions trained on a data set comprising a population of which the subject is not a member and the subject may comprise a person who is not a member of the population. The diagnostic module may comprise a diagnostic classifier trained on plurality of profiles of a subject population of at least 10,000 people and therapeutic profile trained on the plurality of profiles of the subject population.

Another Exemplary System

In another aspect, a system to evaluate of at least one cognitive function attribute of a subject may comprise: a processor configured with instructions that when executed cause the processor to: present a plurality of questions from a plurality of chains of classifiers, the plurality of chains of classifiers comprising a first chain comprising a social/behavioral delay classifier and a second chain comprising a speech & language delay classifier. The social/behavioral delay classifier may be operatively coupled to an autism & attention deficit hyperactivity disorder (ADHD) classifier. The social/behavioral delay classifier may be configured to output a positive result if the subject has a social/behavioral delay and a negative result if the subject does not have the social/behavioral delay. The social/behavioral delay classifier may be configured to output an inconclusive result if it cannot be determined with a specified sensitivity and specificity whether or not the subject has the social/behavioral delay. The social/behavioral delay classifier output may be coupled to an input of an Autism and ADHD classifier and the Autism and ADHD classifier may be configured to output a positive result if the subject has Autism or ADHD. The output of the Autism and ADHD classifier may be coupled to an input of an Autism v. ADHD classifier, and the Autism v. ADHD classifier may be configured to generate a first output if the subject has autism and a second output if the subject has ADHD. The Autism v. ADHD classifier may be configured to provide an inconclusive output if it cannot be determined with specified sensitivity and specificity whether or not the subject has autism or ADHD. The speech & language delay classifier may be operatively coupled to an intellectual disability classifier. The speech & language delay classifier may be configured to output a positive result if the subject has a speech and language delay and a negative output if the subject does not have the speech and language delay. The speech & language delay classifier may be configured to output an inconclusive result if it cannot be determined with a specified sensitivity and specificity whether or not the subject has the speech and language delay. The speech & language delay classifier output may be coupled to an input of an intellectual disability classifier and the intellectual disability classifier may be configured to generate a first output if the subject has intellectual disability and a second output if the subject has the speech and language delay but no intellectual disability. The intellectual disability classifier may be configured to provide an inconclusive output if it cannot be determined with a specified sensitivity and specificity whether or not the subject has the intellectual disability.

The processor may be configured with instructions to present questions for each chain in sequence and skip overlapping questions. The first chain may comprise the social/behavioral delay classifier coupled to an autism & ADHD classifier. The second chain may comprise the speech & language delay classifier coupled to an intellectual disability classifier. A user may go through the first chain and the second chain in sequence.

Another Exemplary Method

In another aspect, a method for administering a drug to a subject may comprise: detecting a neurological disorder of the subject with a machine learning classifier; and administering the drug to the subject in response to the detected neurological disorder.

Amphetamine may be administered with a dosage of 5 mg to 50 mg. Dextroamphetamine may be administered with a dosage that is in a range of 5 mg to 60 mg. Methylphenidate may be administered with a dosage that is in a range of 5 mg to 60 mg. Methamphetamine may be administered with a dosage that is in a range of 5 mg to 25 mg. Dexmethylphenidate may be administered with a dosage that is in a range of 2.5 mg to 40 mg. Guanfacine may be administered with a dosage that is in a range of 1 mg to 10 mg. Atomoxetine may be administered with a dosage that is in a range of 10 mg to 100 mg. Lisdexamfetamine may be administered with a dosage that is in a range of 30 mg to 70 mg. Clonidine may be administered with a dosage that is in a range of 0.1 mg to 0.5 mg. Modafinil may be administered with a dosage that is in a range of 100 mg to 500 mg. Risperidone may be administered with a dosage that is in a range of 0.5 mg to 20 mg. Quetiapine may be administered with a dosage that is in a range of 25 mg to 1000 mg. Buspirone may be administered with a dosage that is in a range of 5 mg to 60 mg. Sertraline may be administered with a dosage of up to 200 mg. Escitalopram may be administered with a dosage of up to 40 mg. Citalopram may be administered with a dosage of up to 40 mg. Fluoxetine may be administered with a dosage that is in a range of 40 mg to 80 mg. Paroxetine may be administered with a dosage that is in a range of 40 mg to 60 mg. Venlafaxine may be administered with a dosage of up to 375 mg. Clomipramine may be administered with a dosage of up to 250 mg. Fluvoxamine may be administered with a dosage of up to 300 mg.

The machine learning classifier may have an inclusion rate of no less than 70%. The machine learning classifier may be capable of outputting an inconclusive result.

Another Exemplary Method

Described herein is a computer-implemented method for evaluating an individual with respect to a plurality of related behavioral disorders, developmental delays, and neurologic impairments, said method comprising: receiving an input for said individual related to said plurality of related behavioral disorders, developmental delays, and neurologic impairments; determining, using an assessment classifier, that said individual has a diagnosis of autism or autism spectrum disorder based on said input; and determining, using a machine learning model, that said autism or said autism spectrum disorder of said individual will be improved by said digital therapy.

In some embodiments, said machine learning model determines a degree improvement that will be achieved by said digital therapy.

In some embodiments, the method comprises providing said digital therapy to said individual when it is determined that said autism or said autism spectrum disorder will be improved by said digital therapy.

In some embodiments, said digital therapy comprises an augmented reality experience.

In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, the method comprises obtaining a video or an image of a person interacted with by said individual in said augmented reality experience with a camera of said mobile computing device.

In some embodiments, the method comprises determining an emotion associated with said person using an image analysis module to analyze said video or said image.

In some embodiments, said virtual reality experience comprises a displayed virtual person or character and said method further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, the method comprises categorizing a sound from said microphone as associated with an emotion.

In some embodiments, the method comprises providing instructions with said digital therapy for said individual to engage in an activity mode.

In some embodiments, said activity mode comprise an emotion elicitation activity, an emotion recognition activity, or unstructured play.

In some embodiments, the method comprises providing a therapeutic agent together with said digital therapy.

In some embodiments, said therapeutic agent improves a cognition of said individual while said individual receives said digital therapy.

In some embodiments, said digital therapy is configured to promote social reciprocity in said individual.

Another Exemplary Device

Described herein is a device for providing digital therapy to an individual with respect to a behavior disorder, developmental delay, or neurologic impairment, said device comprising: a display; and a processor configured with instructions to: receive an input for said individual related to said plurality of related behavioral disorders, developmental delays, and neurologic impairments; determine, using an assessment classifier, that said individual has a diagnosis of autism or autism spectrum disorder based on said input; and determine, using a machine learning model, that said autism or said autism spectrum disorder of said individual will be improved by said digital therapy.

In some embodiments, said machine learning model determines a degree improvement that will be achieved by said digital therapy.

In some embodiments, said processor is configured with further instructions to provide said digital therapy to said individual when it is determined that said autism or said autism spectrum disorder will be improved by said digital therapy.

In some embodiments, said digital therapy comprises an augmented reality experience.

In some embodiments, said digital therapy comprises a virtual reality experience.

In some embodiments, said digital therapy is provided by a mobile computing device.

In some embodiments, said mobile computing device comprises a smartphone, tablet computer, laptop, smartwatch or other wearable computing device.

In some embodiments, said processor is configured with further instructions to obtain a video or an image of a person interacted with by said individual in said augmented reality experience with a camera of said mobile computing device.

In some embodiments, said processor is configured with further instructions to determine an emotion associated with said person using an image analysis module to analyze said video or said image.

In some embodiments, said virtual reality experience comprises a displayed virtual person or character and said device further comprises determining an emotion expressed by said virtual person or character within said virtual reality experience.

In some embodiments, a description of said emotion is displayed to said individual in real time within said augmented reality or virtual reality experience by either printing said description on a screen of said mobile computing device or by sounding said description through an audio output coupled with said mobile computing device.

In some embodiments, said analysis module comprises a facial recognition module for detecting the face of said person within said video or image.

In some embodiments, said image analysis module comprises a classifier trained using machine learning to categorize said face as exhibiting said emotion.

In some embodiments, said computing device comprises a microphone configured to capture audio from said augmented reality experience.

In some embodiments, said processor is configured with further instructions to categorize a sound from said microphone as associated with an emotion.

In some embodiments, said processor is configured with further instructions to provide instructions with said digital therapy for said individual to engage in an activity mode.

In some embodiments, said activity mode comprises an emotion elicitation activity, an emotion recognition activity, or unstructured play.

In some embodiments, a therapeutic agent is provided to said individual together with said digital therapy.

In some embodiments, said therapeutic agent improves a cognition of said individual while said individual receives said digital therapy.

In some embodiments, said digital therapy is configured to promote social reciprocity in said individual.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth non-limiting illustrative embodiments, in which the principles of the invention are utilized, and the accompanying drawings of which:

DETAILED DESCRIPTION OF THE INVENTION

Figure 1A:
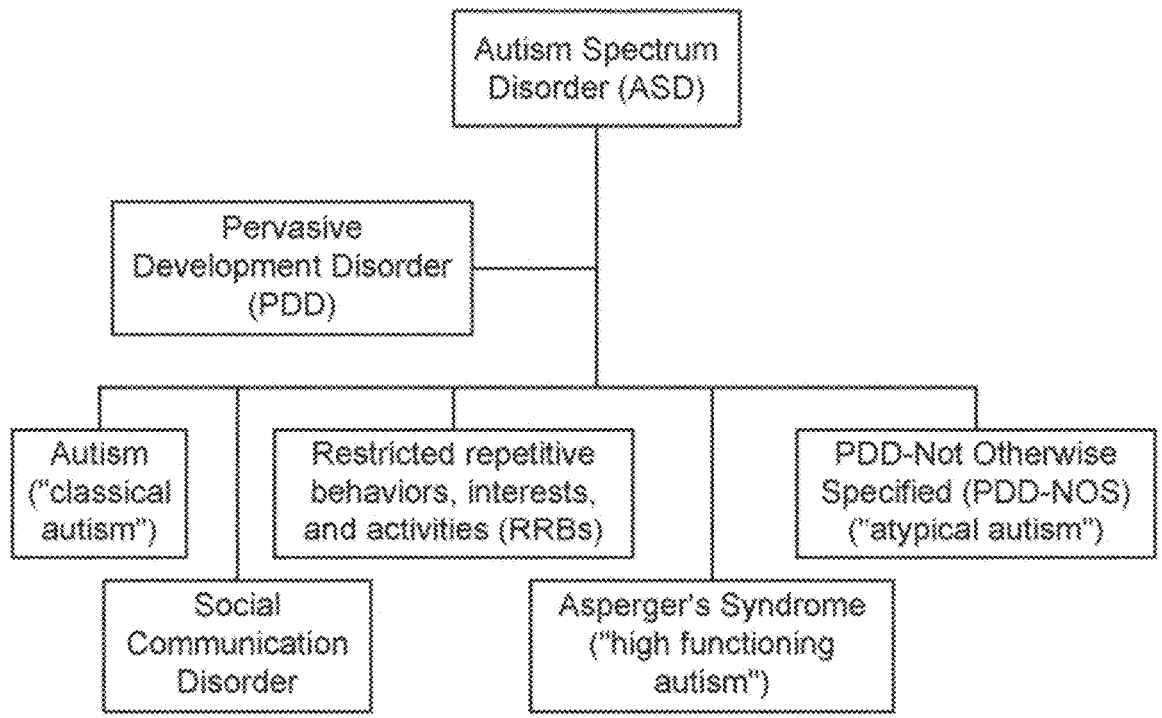
FIGS. 1A and 1B show some developmental disorders that may be evaluated using the assessment procedure as described herein.

The terms "based on" and "in response to" are used interchangeably with the present disclosure.

The term "processor" encompasses one or more of a local processor, a remote processor, or a processor system, and combinations thereof.

The term "feature" is used herein to describe a characteristic or attribute that is relevant to determining the developmental progress of a subject. For example, a "feature" may refer to a clinical characteristic that is relevant to clinical evaluation or diagnosis of a subject for one or more developmental disorders (e.g., age, ability of subject to engage in pretend play, etc.). The term "feature value" is herein used to describe a particular subject's value for the corresponding feature. For example, a "feature value" may refer to a clinical characteristic of a subject that is related to one or more developmental disorders (e.g., if feature is "age", feature value could be 3; if feature is "ability of subject to engage in pretend play", feature value could be "variety of pretend play" or "no pretend play").

As used herein, the phrases "autism" and "autism spectrum disorder" may be used interchangeably.

As used herein, the phrases "attention deficit disorder (ADD)" and "attention deficit/hyperactivity disorder (ADHD)" may be used interchangeably.

As used herein, the term "facial recognition expression activity" refers to the therapeutic activity (e.g., in a digital therapy application or device) wherein children are prompted to find people in their environment displaying a particular emotion and receive real-time emotion confirmation. Facial recognition expression activity can also be described as unstructured play. This activity provides reinforcement that faces have variation in emotion and training on how to differentiate between emotions.

As used herein, the phrase "social reciprocity" refers to the back and forth reciprocal social interactions and/or communications between individuals. Social reciprocity can include verbal and non-verbal social interactions such as, for example, a conversation or an exchange of facial expressions and/or body language. One or more elements or indicators of social reciprocity may be measured according to the platforms, systems, devices, methods, and media disclosed herein. For example, social reciprocity can be measured using eye contact or gaze fixation, verbal responsiveness to a social or emotional cue (e.g., saying "hi" in response to a greeting by a parent), non-verbal responsiveness to a social or emotional cue (e.g., smiling in response to a smile from a parent).

Described herein are methods and devices for determining the developmental progress of a subject. For example, the described methods and devices can identify a subject as developmentally advanced in one or more areas of development or cognitively declining in one or more cognitive functions, or identify a subject as developmentally delayed or at risk of having one or more developmental disorders. The methods and devices disclosed can determine the subject's developmental progress by evaluating a plurality of characteristics or features of the subject based on an assessment model, wherein the assessment model can be generated from large datasets of relevant subject populations using machine-learning approaches.

While methods and devices are herein described in the context of identifying one or more developmental disorders of a subject, the methods and devices are well-suited for use in determining any developmental progress of a subject. For example, the methods and devices can be used to identify a subject as developmentally advanced, by identifying one or more areas of development in which the subject is advanced. To identify one or more areas of advanced development, the methods and devices may be configured to assess one or more features or characteristics of the subject that are related to advanced or gifted behaviors, for example. The methods and devices as described can also be used to identify a subject as cognitively declining in one or more cognitive functions, by evaluating the one or more cognitive functions of the subject.

Described herein are methods and devices for diagnosing or assessing risk for one or more developmental disorders in a subject. The method may comprise providing a data processing module, which can be utilized to construct and administer an assessment procedure for screening a subject for one or more of a plurality of developmental disorders or conditions. The assessment procedure can evaluate a plurality of features or characteristics of the subject, wherein each feature can be related to the likelihood of the subject having at least one of the plurality of developmental disorders screenable by the procedure. Each feature may be related to the likelihood of the subject having two or more related developmental disorders, wherein the two or more related disorders may have one or more related symptoms. The features can be assessed in many ways. For example, the features may be assessed via a subject's answers to questions, observations of a subject, or results of a structured interaction with a subject, as described in further detail herein.

To distinguish among a plurality of developmental disorders of the subject within a single screening procedure, the procedure can dynamically select the features to be evaluated in the subject during administration of the procedure, based on the subject's values for previously presented features (e.g., answers to previous questions). The assessment procedure can be administered to a subject or a caretaker of the subject with a user interface provided by a computing device. The computing device comprises a processor having instructions stored thereon to allow the user to interact with the data processing module through a user interface. The assessment procedure may take less than 10 minutes to administer to the subject, for example 5 minutes or less. Thus, apparatus and methods described herein can provide a prediction of a subject's risk of having one or more of a plurality of developmental disorders using a single, relatively short screening procedure.

The methods and devices disclosed herein can be used to determine a most relevant next question related to a feature of a subject, based on previously identified features of the subject. For example, the methods and devices can be configured to determine a most relevant next question in response to previously answered questions related to the subject. A most predictive next question can be identified after each prior question is answered, and a sequence of most predictive next questions and a corresponding sequence of answers generated. The sequence of answers may comprise an answer profile of the subject, and the most predictive next question can be generated in response to the answer profile of the subject.

The methods and devices disclosed herein are well suited for combinations with prior questions that can be used to diagnose or identify the subject as at risk in response to fewer questions by identifying the most predictive next question in response to the previous answers, for example.

In one aspect, a method of providing an evaluation of at least one cognitive function attribute of a subject comprises the operations of: on a computer system having a processor and a memory storing a computer program for execution by the processor. The computer program may comprise instructions for: 1) receiving data of the subject related to the cognitive function attribute; 2) evaluating the data of the subject using a machine learning model; and 3) providing an evaluation for the subject. The evaluation may be selected from the group consisting of an inconclusive determination and a categorical determination in response to the data. The machine learning model may comprise a selected subset of a plurality of machine learning assessment models. The categorical determination may comprise a presence of the cognitive function attribute and an absence of the cognitive function attribute.

Receiving data from the subject may comprise receiving an initial set of data. Evaluating the data from the subject may comprise evaluating the initial set of data using a preliminary subset of tunable machine learning assessment models selected from the plurality of tunable machine learning assessment models to output a numerical score for each of the preliminary subset of tunable machine learning assessment models. The method may further comprise providing a categorical determination or an inconclusive determination as to the presence or absence of the cognitive function attribute in the subject based on the analysis of the initial set of data, wherein the ratio of inconclusive to categorical determinations can be adjusted.

The method may further comprise the operations of: 1) determining whether to apply additional assessment models selected from the plurality of tunable machine learning assessment models if the analysis of the initial set of data yields an inconclusive determination; 2) receiving an additional set of data from the subject based on an outcome of the decision; 3) evaluating the additional set of data from the subject using the additional assessment models to output a numerical score for each of the additional assessment models based on the outcome of the decision; and 4) providing a categorical determination or an inconclusive determination as to the presence or absence of the cognitive function attribute in the subject based on the analysis of the additional set of data from the subject using the additional assessment models. The ratio of inconclusive to categorical determinations may be adjusted.

The method may further comprise the operations: 1) combining the numerical scores for each of the preliminary subset of assessment models to generate a combined preliminary output score; and 2) mapping the combined preliminary output score to a categorical determination or to an inconclusive determination as to the presence or absence of the cognitive function attribute in the subject. The ratio of inconclusive to categorical determinations may be adjusted. The method may further comprise the operations of: 1) combining the numerical scores for each of the additional assessment models to generate a combined additional output score; and 2) mapping the combined additional output score to a categorical determination or to an inconclusive determination as to the presence or absence of the cognitive function attribute in the subject. The ratio of inconclusive to categorical determinations may be adjusted. The method may further comprise employing rule-based logic or combinatorial techniques for combining the numerical scores for each of the preliminary subset of assessment models and for combining the numerical scores for each of the additional assessment models.

The ratio of inconclusive to categorical determinations may be adjusted by specifying an inclusion rate and wherein the categorical determination as to the presence or absence of the developmental condition in the subject is assessed by providing a sensitivity and specificity metric. The inclusion rate may be no less than 70% with the categorical determination resulting in a sensitivity of at least 70% with a corresponding specificity in of at least 70%. The inclusion rate may be no less than 70% with the categorical determination resulting in a sensitivity of at least 80 with a corresponding specificity in of at least 80%. The inclusion rate may be no less than 70% with the categorical determination resulting in a sensitivity of at least 90% with a corresponding specificity in of at least 90%. The data from the subject may comprise at least one of a sample of a diagnostic instrument, wherein the diagnostic instrument comprises a set of diagnostic questions and corresponding selectable answers, and demographic data.

The method may further comprise training a plurality of tunable machine learning assessment models using data from a plurality of subjects previously evaluated for the developmental condition. The training may comprise the operations of 1) pre-processing the data from the plurality of subjects using machine learning techniques; 2) extracting and encoding machine learning features from the pre-processed data; 3) processing the data from the plurality of subjects to mirror an expected prevalence of a cognitive function attribute among subjects in an intended application setting; 4) selecting a subset of the processed machine learning features; 5) evaluating each model in the plurality of tunable machine learning assessment models for performance; and 6) determining an optimal set of parameters for each model based on determining the benefit of using all models in a selected subset of the plurality of tunable machine learning assessment models. Each model may be evaluated for sensitivity and specificity for a pre-determined inclusion rate. Determining an optimal set of parameters for each model may comprise tuning the parameters of each model under different tuning parameter settings. Processing the encoded machine learning features may comprise computing and assigning sample weights to every sample of data. Each sample of data may correspond to a subject in the plurality of subjects. Samples may be grouped according to subject-specific dimensions. Sample weights may be computed and assigned to balance one group of samples against every other group of samples to mirror the expected distribution of each dimension among subjects in an intended setting. The subject-specific dimensions may comprise a subject's gender, the geographic region where a subject resides, and a subject's age. Extracting and encoding machine learning features from the pre-processed data may comprise using feature encoding techniques such as but not limited to one-hot encoding, severity encoding, and presence-of-behavior encoding. Selecting a subset of the processed machine learning features may comprise using bootstrapping techniques to identify a subset of discriminating features from the processed machine learning features.

The cognitive function attribute may comprise a behavioral disorder and a developmental advancement. The categorical determination provided for the subject may be selected from the group consisting of an inconclusive determination, a presence of multiple cognitive function attributes and an absence of multiple cognitive function attributes in response to the data.

In another aspect, an apparatus to evaluate a cognitive function attribute of a subject may comprise a processor. The processor may be configured with instructions that, when executed, cause the processor to receive data of the subject related to the cognitive function attribute and applies rules to generate a categorical determination for the subject. The categorical determination may be selected from a group consisting of an inconclusive determination, a presence of the cognitive function attribute, and an absence of the cognitive function attribute in response to the data. The cognitive function attribute may be determined with a sensitivity of at least 70% and a specificity of at least 70%, respectively, for the presence or the absence of the cognitive function attribute. The cognitive function attribute may be selected from a group consisting of autism, autistic spectrum, attention deficit disorder, attention deficit hyperactive disorder and speech and learning disability. The cognitive function attribute may be determined with a sensitivity of at least 80% and a specificity of at least 80%, respectively, for the presence or the absence of the cognitive function attribute. The cognitive function attribute may be determined with a sensitivity of at least 90% and a specificity of at least 90%, respectively, for the presence or the absence of the cognitive function attribute. The cognitive function attribute may comprise a behavioral disorder and a developmental advancement.

In another aspect, a non-transitory computer-readable storage media encoded with a computer program including instructions executable by a processor to evaluate a cognitive function attribute of a subject comprises a database, recorded on the media. The database may comprise data of a plurality of subjects related to at least one cognitive function attribute and a plurality of tunable machine learning assessment models; an evaluation software module; and a model tuning software module. The evaluation software module may comprise instructions for: 1) receiving data of the subject related to the cognitive function attribute; 2) evaluating the data of the subject using a selected subset of a plurality of machine learning assessment models; and 3) providing a categorical determination for the subject, the categorical determination selected from the group consisting of an inconclusive determination, a presence of the cognitive function attribute and an absence of the cognitive function attribute in response to the data. The model tuning software module may comprise instructions for: 1) pre-processing the data from the plurality of subjects using machine learning techniques; 2) extracting and encoding machine learning features from the pre-processed data; 3) processing the encoded machine learning features to mirror an expected distribution of subjects in an intended application setting; 4) selecting a subset of the processed machine learning features; 5) evaluating each model in the plurality of tunable machine learning assessment models for performance; 6) tuning the parameters of each model under different tuning parameter settings; and 7) determining an optimal set of parameters for each model based on determining the benefit of using all models in a selected subset of the plurality of tunable machine learning assessment models. Each model may be evaluated for sensitivity and specificity for a predetermined inclusion rate. The cognitive function attribute may comprise a behavioral disorder and a developmental advancement.

In another aspect, a computer-implemented system may comprise a digital processing device. The digital processing may comprise at least one processor, an operating system configured to perform executable instructions, a memory, and a computer program. The memory may comprise storage for housing data of a plurality of subjects related to at least one cognitive function attribute and storage for housing a plurality of machine learning assessment models. The computer program may include instructions executable by the digital processing device for: 1) receiving data of the subject related to the cognitive function attribute; 2) evaluating the data of the subject using a selected subset of a plurality of machine learning assessment models; and 3) providing a categorical determination for the subject, the categorical determination selected from the group consisting of an inconclusive determination, a presence of the cognitive function attribute and an absence of the cognitive function attribute in response to the data. The cognitive function attribute may comprise a behavioral disorder and a developmental advancement.

In another aspect, a mobile device for providing an evaluation of at least one cognitive function attribute of a subject may comprise a display and a processor. The processor may be configured with instructions to receive and display data of the subject related to the cognitive function attribute and receive and display an evaluation for the subject. The evaluation may be selected from the group consisting of an inconclusive determination and a categorical determination. The evaluation for the subject may be determined in response to the data of the subject. The categorical determination may be selected from the group consisting of a presence of the cognitive function attribute and an absence of the cognitive function attribute. The cognitive function attribute may be determined with a sensitivity of at least 80 and a specificity of at least 80, respectively, for the presence or the absence of the cognitive function attribute. The cognitive function attribute may be determined with a sensitivity of at least 90 and a specificity of at least 90, respectively, for the presence or the absence of the cognitive function attribute. The cognitive function attribute may comprise a behavioral disorder and a developmental advancement.

In another aspect, a digital therapeutic system to treat a subject with a personal therapeutic treatment plan may comprise one or more processors, a diagnostic module to receive data from the subject and output diagnostic data for the subject, and a therapeutic module to receive the diagnostic data and output the personal therapeutic treatment plan for the subject. The diagnostic module may comprise one or more classifiers built using machine learning or statistical modeling based on a subject population to determine the diagnostic data for the subject. The diagnostic data may comprise an evaluation for the subject, the evaluation selected from the group consisting of an inconclusive determination and a categorical determination in response to data received from the subject. The therapeutic module may comprise one or more models built using machine learning or statistical modeling based on at least a portion the subject population to determine and output the personal therapeutic treatment plan of the subject. The diagnostic module may be configured to receive updated subject data from the subject in response to therapy of the subject and generate updated diagnostic data from the subject. The therapeutic module may be configured to receive the updated diagnostic data and output an updated personal treatment plan for the subject in response to the diagnostic data and the updated diagnostic data. The diagnostic module may comprise a diagnostic machine learning classifier trained on the subject population. The therapeutic module may comprise a therapeutic machine learning classifier trained on the at least the portion of the subject population. The diagnostic module and the therapeutic module may be arranged for the diagnostic module to provide feedback to the therapeutic module based on performance of the treatment plan. The therapeutic classifier may comprise instructions trained on a data set comprising a population of which the subject is not a member. The subject may comprise a person who is not a member of the population. The diagnostic module may comprise a diagnostic classifier trained on plurality of profiles of a subject population of at least 10,000 people and therapeutic profile trained on the plurality of profiles of the subject population.

In another aspect, a digital therapeutic system to treat a subject with a personal therapeutic treatment plan may comprise a processor, a diagnostic module to receive data from the subject and output diagnostic data for the subject, and a therapeutic module to receive the diagnostic data and output the personal therapeutic treatment plan for the subject. The diagnostic data may comprise an evaluation for the subject, the evaluation selected from the group consisting of an inconclusive determination and a categorical determination in response to data received from the subject. The personal therapeutic treatment plan may comprise digital therapeutics. The digital therapeutics may comprise instructions, feedback, activities or interactions provided to the subject or caregiver. The digital therapeutics may be provided with a mobile device. The diagnostics data and the personal therapeutic treatment plan may be provided to a third-party system. The third-party system may comprise a computer system of a health care professional or a therapeutic delivery system. The diagnostic module may be configured to receive updated subject data from the subject in response to a feedback data of the subject and generate updated diagnostic data. The therapeutic module may be configured to receive the updated diagnostic data and output an updated personal treatment plan for the subject in response to the diagnostic data and the updated diagnostic data. The updated subject data may be received in response to a feedback data that identifies relative levels of efficacy, compliance and response resulting from the personal therapeutic treatment plan. The diagnostic module may use machine learning or statistical modeling based on a subject population to determine the diagnostic data. The therapeutic module may be based on at least a portion the subject population to determine the personal therapeutic treatment plan of the subject. The diagnostic module may comprise a diagnostic machine learning classifier trained on a subject population. The therapeutic module may comprise a therapeutic machine learning classifier trained on at least a portion of the subject population. The diagnostic module may be configured to provide feedback to the therapeutic module based on performance of the personal therapeutic treatment plan. The data from the subject may comprise at least one of the subject and caregiver video, audio, responses to questions or activities, and active or passive data streams from user interaction with activities, games or software features of the system. The subject may have a risk selected from the group consisting of a behavioral disorder, neurological disorder and mental health disorder. The behavioral, neurological or mental health disorder may be selected from the group consisting of autism, autistic spectrum, attention deficit disorder, depression, obsessive compulsive disorder, schizophrenia, Alzheimer's disease, dementia, attention deficit hyperactive disorder and speech and learning disability. The diagnostic module may be configured for an adult to perform an assessment or provide data for an assessment of a child or juvenile. The diagnostic module may be configured for a caregiver or family member to perform an assessment or provide data for an assessment of the subject.

In another aspect, a non-transitory computer-readable storage media may be encoded with a program. The computer program may include executable instructions for: 1) receiving input data from the subject and outputting diagnostic data for the subject; 2) receiving the diagnostic data and outputting a personal therapeutic treatment plan for the subject; and 3) evaluating the diagnostic data based on at least a portion the subject population to determine and output the personal therapeutic treatment plan of the subject. The diagnostic data may comprise an evaluation for the subject, the evaluation selected from the group consisting of an inconclusive determination and a categorical determination in response to input data received from the subject. Updated subject input data may be received from the subject in response to therapy of the subject and updated diagnostic data may be generated from the subject. Updated diagnostic data may be received and an updated personal treatment plan may be outputted for the subject in response to the diagnostic data and the updated diagnostic data.

In another aspect, a non-transitory computer-readable storage media may be encoded with a computer program. The computer program may include executable instructions for receiving input data from a subject and outputting diagnostic data for the subject and receiving the diagnostic data and outputting a personal therapeutic treatment plan for the subject. The diagnostic data may comprise an evaluation for the subject, the evaluation selected from the group consisting of an inconclusive determination and a categorical determination in response to data received from the subject. The personal therapeutic treatment plan may comprise digital therapeutics.

In another aspect, a method of treating a subject with a personal therapeutic treatment plan may comprise a diagnostic process of receiving data from the subject and outputting diagnostic data for the subject wherein the diagnostic data comprises an evaluation for the subject and a therapeutic process of receiving the diagnostic data and outputting the personal therapeutic treatment plan for the subject. The evaluation may be selected from the group consisting of an inconclusive determination and a categorical determination in response to data received from the subject. The diagnostic process may comprise receiving updated subject data from the subject in response to a therapy of the subject and generating an updated diagnostic data from the subject. The therapeutic process may comprise receiving the updated diagnostic data and outputting an updated personal treatment plan for the subject in response to the diagnostic data and the updated diagnostic data. The updated subject data may be received in response to a feedback data that identifies relative levels of efficacy, compliance and response resulting from the personal therapeutic treatment plan. The personal therapeutic treatment plan may comprise digital therapeutics. The digital therapeutics may comprise instructions, feedback, activities or interactions provided to the subject or caregiver. The digital therapeutics may be provided with a mobile device. The method may further comprise providing the diagnostics data and the personal therapeutic treatment plan to a third-party system. The third-party system may comprise a computer system of a health care professional or a therapeutic delivery system. The diagnostic process may be performed by a process selected from the group consisting of machine learning, a classifier, artificial intelligence, or statistical modeling based on a subject population to determine the diagnostic data. The therapeutic process may be performed by a process selected from the group consisting of machine learning, a classifier, artificial intelligence, or statistical modeling based on at least a portion the subject population to determine the personal therapeutic treatment plan of the subject. The diagnostic process may be performed by a diagnostic machine learning classifier trained on a subject population. The therapeutic process may be performed by a therapeutic machine learning classifier trained on at least a portion of the subject population. The diagnostic process may comprise providing feedback to the therapeutic module based on performance of the personal therapeutic treatment plan. The data from the subject may comprise at least one of the subject and caregiver video, audio, responses to questions or activities, and active or passive data streams from user interaction with activities, games or software features. The diagnostic process may be performed by an adult to perform an assessment or provide data for an assessment of a child or juvenile. The diagnostic process may enable a caregiver or family member to perform an assessment or provide data for an assessment of the subject. The subject may have a risk selected from the group consisting of a behavioral disorder, neurological disorder, and mental health disorder. The risk may be selected from the group consisting of autism, autistic spectrum, attention deficit disorder, depression, obsessive compulsive disorder, schizophrenia, Alzheimer's disease, dementia, attention deficit hyperactive disorder, and speech and learning disability.

Disclosed herein are systems and methods that provide diagnosis together with digital therapy using readily available computing devices (e.g. smartphones) and utilize machine learning.

Described herein are methods and devices for evaluating and treating an individual having one or more diagnoses from the related categories of behavioral disorders, developmental delays, and neurologic impairments. In some embodiments, an evaluation comprises an identification or confirmation of a diagnosis of an individual wherein the diagnosis falls within one or more of the related categories of diagnoses comprising: behavioral disorders, developmental delays, and neurologic impairments. In some embodiments, an evaluation as carried out by a method or device described herein comprises an assessment of whether an individual will respond to a treatment. In some embodiments, an evaluation as carried out by a method or device described herein comprises an assessment of the degree to which an individual will respond to a particular treatment. For example, in some embodiments, an individual is assessed, using the methods or devices described herein, as being highly responsive to a digital therapy. In some embodiments, a digital therapy is administered when it is determined that an individual will be highly responsive to the digital therapy.

Also described herein are personalized treatment regimen comprising digital therapeutics, non-digital therapeutics, pharmaceuticals, or any combination thereof. In some embodiments, a therapeutic agent is administered together with the digital therapy. In some embodiments, a therapeutic agent administered together with a digital therapy is configured to improve the performance of the digital therapy for the individual receiving the digital therapy. In some embodiments, a therapeutic agent administered with a digital therapy improves the cognition of the individual receiving the digital therapy. In some embodiments, the therapeutic agent relaxes the individual receiving the digital therapy. In some embodiments, the therapeutic agent improves the level of concentration or focus of the individual receiving the digital therapy.

Digital therapeutics can comprise instructions, feedback, activities or interactions provided to an individual or caregiver by a method or device described herein. Digital therapeutics in some embodiments are configured to suggest behaviors, activities, games or interactive sessions with system software and/or third party devices.

The digital therapeutics utilized by the methods and devices described herein can be implemented using various digital applications, including augmented reality, virtual reality, real-time cognitive assistance, or other behavioral therapies augmented using technology. Digital therapeutics can be implemented using any device configured to produce a virtual or augmented reality environment. Such devices can be configured to include one or more sensor inputs such as video and/or audio captured using a camera and/or microphone. Non-limiting examples of devices suitable for providing digital therapy as described herein include wearable devices, smartphones, tablet computing devices, laptops, projectors and any other device suitable for producing virtual or augmented reality experiences.

The systems and methods described herein can provide social learning tools or aids for users through technological augmentation experiences (e.g., augmented reality and/or virtual reality). In some embodiments, a digital therapy is configured to promote or improve social reciprocity in an individual. In some embodiments, a digital therapy is configured to promote or improve social reciprocity in an individual having autism or autism spectrum disorder.

In some embodiments of the methods and devices described herein, a method or device for delivering a virtual or augmented reality based digital therapy receives inputs and in some of these embodiments an input affects how a virtual or augmented reality is presented to an individual receiving therapy. In some embodiments, an input is received from a camera and/or microphone of a computing device used to deliver the digital therapy. In some instances, an inputs is received from a sensor such as, for example, a motion sensor or a vital sign sensor. In some embodiments, inputs in the form of videos, images, and/or sounds are captured and analyzed using algorithm(s) such as artificial intelligence or machine learning models to provide feedback and/or behavioral modification to the subject through the virtual or augmented reality experience that is provided.

In some embodiments, an input to a method or device comprises an evaluation of a facial expression or other social cue of one or more other individuals that a digital therapy recipient interacts with either in a virtual reality or an augmented reality interaction.

In a non-limiting example of an augmented reality digital therapy experience, an individual may react with a real person, and in this example, a video, image, and/or sound recording of the person is taken by the computing device that is delivering the digital therapy. Then, the video, image, and/or sound recording is analyzed using analysis classifier that determines an emotion associated with a facial expression (or other social cue) of the person interacted with by the individual in the augmented reality environment. An analysis of the facial expression (or other social cue) may comprise an assessment of an emotion or a mood associated with the facial expression and/or other social cue. The result of the analysis is then provided to the individual receiving the digital therapy. In some embodiments, the result of the analysis is displayed within the augmented reality environment. In some embodiments, the result of the analysis is displayed on a screen of a computing device. In some embodiments, the result of the analysis is provided via an audible sound or message.

In a non-limiting example of an virtual reality digital therapy experience, an individual receiving the digital therapy may interact with an image or representation of a real person or an image or representation of a virtual object or character such as a cartoon character or other artistic rendering of an interactive object. In this example, the software determines an emotion that is conveyed by the virtual person, character, or object within the virtual reality environment. The result of the analysis is then provided to the individual receiving the digital therapy. In some embodiments, the result of the analysis is displayed within the augmented reality environment. In some embodiments, the result of the analysis is displayed on a screen of a computing device. In some embodiments, the result of the analysis is provided via an audible sound or message.

As a further illustrative example, a smiling individual that is interacted with by a digital therapy recipient is evaluated as being happy. In this example, the input comprises the evaluation of the facial expression or other social cue and it is displayed to or otherwise made available to the recipient of digital therapy to help with learning to recognize these facial expressions or social cues. That is, in this example, the emotion that the individual is evaluated as expressing (in this example happiness) is displayed or otherwise made available to the digital therapy recipient, by, for example, displaying the word "happy" on a screen of a mobile computing during or around the time that the individual is smiling in the virtual or augmented reality experience. Examples of emotions that can be detected and/or used in various games or activities as described herein include happy, sad, angry, surprise, frustrated, afraid/scared, calm, disgusted, and contempt.

In certain instances, the device uses audio or visual signals to communicate to the subject the emotion or social cue detected for the other individual captured as input(s). Visual signals can be displayed as words, designs or pictures, emoticons, colors, or other visual cues that correspond to detected emotions or social cues. Audio signals can be communicated as audio words, sounds such as tones or beats, music, or other audio cues that correspond to detected emotions or social cues. In some cases, a combination of visual and audio signals are utilized. These cues can be customized or selected from an array of cues to provide a personalized set of audio/visual signals. Signals can also be switched on or off as part of this customized experience.

In certain instances, the digital therapy experience comprises an activity mode. The activity mode can include an emotion elicitation activity, an emotion recognition activity, or unstructured play. The unstructured play can be an unscripted, free roaming, or otherwise unstructured mode in which a user is free to engage in one or more digital therapy activities. An example of an unstructured mode is a game or activity in which the user is free to collect one or more images or representations of real persons or images or representations of virtual objects or characters such as a cartoon character or other artistic rendering of an interactive object. This unstructured mode can be characterized as having a "sandbox" style of play that places few limitations on user decisions or gameplay in contrast to a progression style that forces a user into a series of tasks. The user can collect such images using the camera of a device such as a smartphone (e.g., taking pictures of other individuals such as a family member or caretaker). Alternatively or in combination, the user can collect images or representations digitally such as via browsing a library or database. As an illustrative example, the user wanders around his house and takes photographs of his parents using a smartphone camera. In addition, the user collects selfies posted by a family member on social media by selecting and/or downloading the photographs onto the smartphone. In some cases, the device displays the live image or a captured or downloaded image along with the identified or classified emotion for the person in the image. This allows the user to engage in unstructured learning while encountering real world examples of emotions being expressed by various other individuals.

An emotion recognition activity can be configured to test and/or train a user to recognize emotions or emotional cues through a structured learning experience. For example, an emotion recognition activity can be used to help a user engage in reinforcement learning by providing images the user has already previously been exposed to (e.g., photographs of a caretaker the user captured during unstructured play). Reinforcement learning allows a user to reinforce their recognition of emotions that have already been shown to them previously. The reinforcement learning can include one or more interactive activities or games. One example is a game in which the user is presented with multiple images corresponding to different emotions (e.g., smartphone screen shows an image of a person smiling and another image of a person frowning) and a prompt to identify an image corresponding to a particular emotion (e.g., screen shows or microphone outputs a question or command for user to identify the correct image). The user can respond by selecting one of the multiple images on the screen or providing an audio response (e.g., stating "left/middle/right image" or "answer A/B/C"). Another example is a game in which the user is presented with a single image corresponding to an emotion and asked to identify the emotion. In some cases, the user is given a choice of multiple emotions. Alternatively, the user must provide a response without being given a selection of choices (e.g., a typed or audio short answer instead of a multiple choice selection). In some cases, a selection of choices is provided. The selection of choices can be visual or non-visual (e.g., an audio selection not shown on the graphic user interface). As an illustrative example, the user is shown an image of a caregiver smiling and prompted by the following audio question "Is this person happy or sad?". Alternatively, the question is shown on the screen. The user can then provide an audio answer or type out an answer. Another example is a game in which a user is presented with multiple images and multiple emotions and can match the images to the corresponding emotions.

In certain instances, the photographed and/or downloaded images are tagged, sorted, and/or filtered for use in one or more activities or games as part of the digital therapy experience. For example, since reinforcement learning can entail the user being queried regarding images that the user has already exposed to, the library of available images may be filtered to remove images that do not satisfy one or more of the following rules: (1) at least one face is successfully detected; (2) at least one emotion is successfully detected; (3) the image has been presented or shown to the user previously. In some cases, the images are further filtered depending the specific activity. For example, a user may be assigned an emotion recognition reinforcement learning activity specifically directed to recognizing anger due to poor performance in previous activities; therefore, the images used for this reinforcement learning activity may also be filtered to include at least one image where anger or an emotional cue corresponding to anger is detected.

In certain instances, the photographed and/or downloaded images are imported into a library of collected images that is accessible by the digital therapeutic software. Alternatively or in combination, the images can be tagged such that they are recognized by the digital therapeutic software as images collected for the purpose of the interactive digital therapy experience. Tagging can be automatic when the user takes photographs within the context of the interactive digital therapy experience. As an illustrative example, a user opens up a digital therapy application on the smartphone and selects the unscripted or free roaming mode. The smartphone then presents a photography interface on its touchscreen along with written and/or audio instructions for taking photographs of other person's faces. Any photographs the user captures using the device camera is then automatically tagged and/or added to the library or database. Alternatively, the user browsing social media outside of the digital therapy application selects a posted image and selects an option to download, import, or tag the image for access by the digital therapy application.

In certain instances, images are tagged to identify relevant information. This information can include the identity of a person in the image (e.g., name, title, relationship to the user) and/or the facial expression or emotion expressed by the person in the image. Facial recognition and emotion classification as described herein can be used to evaluate an image to generate or determine one or more tags for the image. As an illustrative example, a user takes a photograph of his caretaker, the photograph is screened for facial recognition, followed by emotion classification based on the recognized face. The classified emotion is "HAPPY", which results in the image being tagged with the identified emotion. In some cases, the tagging is performed by another user, for example, a parent or caregiver. As an illustrative example, the parent logs into the digital therapeutic application and accesses the library or database of images collected by the user. The parent sorts for untagged images and then selects the appropriate tags for the emotions expressed by the person within the images.

As an illustrative example, a computing device comprising a camera and microphone tracks faces and classifies the emotions of the digital therapy recipient's social partners using an outward-facing camera and microphone, and provides two forms of cues to the digital therapy recipient in real time. The device also has an inward-facing digital display having a peripheral monitor and a speaker. An expression of an individual interacted with by the digital therapy recipient is assessed using a machine learning classifier and when a face is classified as expressing an emotion, the emotion is an input to the device and is displayed or otherwise presented to the recipient of the digital therapy.

In some cases, the device also comprises an inward-facing camera (e.g., a "selfie" camera) and tracks and classifies the emotions of the digital therapy recipient. The tracking and classification of the emotions of the social partner and the emotions of the digital therapy recipient can be performed in real time simultaneously or in close temporal proximity (e.g., within 1, 2, 3, 4, or 5 seconds of each other, or some other appropriate time frame). Alternatively, images may be captured of the social partner and/or digital therapy recipient and then evaluated to track and classify their respective emotions at a later time (i.e., not in real time). This allows the social interaction between the patient and the target individual to be captured, for example, as the combined facial expression and/or emotion of both persons. In some cases, the detected expressions and/or emotions of the parties to a social interaction are time-stamped or otherwise ordered so as to determine a sequence of expressions, emotions, or other interactions that make up one or more social interactions. These social interactions can be evaluated for the patient's ability to engage in social reciprocity.

As an illustrative example, the patient points the phone at his parent who smiles at him. The display screen of the phone displays an emoticon of a smiley face in real time to help the patient recognize the emotion corresponding to his parent's facial expression. In addition, the display screen optionally provides instructions for the patient to respond to the parent. The patient does not smile back at his parent, and the inward facing camera captures this response in one or more images or video. The images and/or videos and a timeline or time-stamped sequence of social interactions are then saved on the device (and optionally uploaded or saved on a remote network or cloud). In this case, the parent's smile is labeled as a "smile", and the patient's lack of response is labeled as "non-responsive" or "no smile". Thus, this particular social interaction is determined to be a failure to engage in smile-reciprocity. The social interaction can also be further segmented based on whether the target individual (parent) and the patient expressed a "genuine" smile as opposed to a "polite smile". For example, the algorithms and classifiers described herein for detecting a "smile" or "emotion" can be trained to distinguish between genuine and polite smiles, which can be differentiated based on visual cues corresponding to the engagement of eye muscles in genuine smiles and the lack of eye muscle engagement in police smiles. This differentiation in types or subtypes of emotions or facial expressions can be based on training the algorithms or classifiers on the appropriate data set of labeled images, for example, images labeled with "polite" vs "genuine" smiles.

In some aspects, the platforms, systems, devices, methods, and media disclosed herein comprise a software application configured to enable management and/or monitoring of the digital therapeutics. The software application can be a mobile application, a web application, or other computer application. In some cases, the application provides a control center that allows the subject or a caregiver of the subject to manage the device. The device can enable a user to review, upload, or delete captured data such as videos, audios, photos, or detected or classified emotional cues. A user can also use the device to enter or configure settings such as, for example, data capture settings (e.g., what kind of data is captured, how long it is stored, etc.). In some cases, the application obtains images (e.g., stills from captured video), executes an emotional cue classifier, and/or saves video and usage data.

Sometimes, the platforms, systems, devices, methods, and media disclosed herein provide digital therapeutics having an interactive feature. The interactive feature in an embodiment is configured so that the digital therapy recipient guesses an emotion of another person based on a facial expression or social cues for all persons interacting with the individual. In some instances, the platforms, systems, devices, methods, and media disclosed herein provide a user with the option to delete captured data such as videos or audios. This option preserves the privacy of the family by enabling them to delete the data. Metrics on the captured data can be obtained or calculated such as usage, age of video, whether the video was saved or deleted, usage during the intervention period, and other relevant parameters.

In some cases, the device operates at a frame rate of ~15-20 FPS, which enables facial expressions recognition within 100 ms. The device can operate at a frame rate of 10 FPS to 100 FPS. The device can operate at a frame rate of 10 FPS to 15 FPS, 10 FPS to 20 FPS, 10 FPS to 25 FPS, 10 FPS to 30 FPS, 10 FPS to 35 FPS, 10 FPS to 40 FPS, 10 FPS to 45 FPS, 10 FPS to 50 FPS, 10 FPS to 60 FPS, 10 FPS to 80 FPS, 10 FPS to 100 FPS, 15 FPS to 20 FPS, 15 FPS to 25 FPS, 15 FPS to 30 FPS, 15 FPS to 35 FPS, 15 FPS to 40 FPS, 15 FPS to 45 FPS, 15 FPS to 50 FPS, 15 FPS to 60 FPS, 15 FPS to 80 FPS, 15 FPS to 100 FPS, 20 FPS to 25 FPS, 20 FPS to 30 FPS, 20 FPS to 35 FPS, 20 FPS to 40 FPS, 20 FPS to 45 FPS, 20 FPS to 50 FPS, 20 FPS to 60 FPS, 20 FPS to 80 FPS, 20 FPS to 100 FPS, 25 FPS to 30 FPS, 25 FPS to 35 FPS, 25 FPS to 40 FPS, 25 FPS to 45 FPS, 25 FPS to 50 FPS, 25 FPS to 60 FPS, 25 FPS to 80 FPS, 25 FPS to 100 FPS, 30 FPS to 35 FPS, 30 FPS to 40 FPS, 30 FPS to 45 FPS, 30 FPS to 50 FPS, 30 FPS to 60 FPS, 30 FPS to 80 FPS, 30 FPS to 100 FPS, 35 FPS to 40 FPS, 35 FPS to 45 FPS, 35 FPS to 50 FPS, 35 FPS to 60 FPS, 35 FPS to 80 FPS, 35 FPS to 100 FPS, 40 FPS to 45 FPS, 40 FPS to 50 FPS, 40 FPS to 60 FPS, 40 FPS to 80 FPS, 40 FPS to 100 FPS, 45 FPS to 50 FPS, 45 FPS to 60 FPS, 45 FPS to 80 FPS, 45 FPS to 100 FPS, 50 FPS to 60 FPS, 50 FPS to 80 FPS, 50 FPS to 100 FPS, 60 FPS to 80 FPS, 60 FPS to 100 FPS, or 80 FPS to 100 FPS. The device can operate at a frame rate of 10 FPS, 15 FPS, 20 FPS, 25 FPS, 30 FPS, 35 FPS, 40 FPS, 45 FPS, 50 FPS, 60 FPS, 80 FPS, or 100 FPS. The device can operate at a frame rate of at least 10 FPS, 15 FPS, 20 FPS, 25 FPS, 30 FPS, 35 FPS, 40 FPS, 45 FPS, 50 FPS, 60 FPS, or 80 FPS. The device can operate at a frame rate of at most 15 FPS, 20 FPS, 25 FPS, 30 FPS, 35 FPS, 40 FPS, 45 FPS, 50 FPS, 60 FPS, 80 FPS, or 100 FPS.

In some cases, the device can detect facial expressions or motions within 10 ms to 200 ms. The device can detect facial expressions or motions within 10 ms to 20 ms, 10 ms to 30 ms, 10 ms to 40 ms, 10 ms to 50 ms, 10 ms to 60 ms, 10 ms to 70 ms, 10 ms to 80 ms, 10 ms to 90 ms, 10 ms to 100 ms, 10 ms to 150 ms, 10 ms to 200 ms, 20 ms to 30 ms, 20 ms to 40 ms, 20 ms to 50 ms, 20 ms to 60 ms, 20 ms to 70 ms, 20 ms to 80 ms, 20 ms to 90 ms, 20 ms to 100 ms, 20 ms to 150 ms, 20 ms to 200 ms, 30 ms to 40 ms, 30 ms to 50 ms, 30 ms to 60 ms, 30 ms to 70 ms, 30 ms to 80 ms, 30 ms to 90 ms, 30 ms to 100 ms, 30 ms to 150 ms, 30 ms to 200 ms, 40 ms to 50 ms, 40 ms to 60 ms, 40 ms to 70 ms, 40 ms to 80 ms, 40 ms to 90 ms, 40 ms to 100 ms, 40 ms to 150 ms, 40 ms to 200 ms, 50 ms to 60 ms, 50 ms to 70 ms, 50 ms to 80 ms, 50 ms to 90 ms, 50 ms to 100 ms, 50 ms to 150 ms, 50 ms to 200 ms, 60 ms to 70 ms, 60 ms to 80 ms, 60 ms to 90 ms, 60 ms to 100 ms, 60 ms to 150 ms, 60 ms to 200 ms, 70 ms to 80 ms, 70 ms to 90 ms, 70 ms to 100 ms, 70 ms to 150 ms, 70 ms to 200 ms, 80 ms to 90 ms, 80 ms to 100 ms, 80 ms to 150 ms, 80 ms to 200 ms, 90 ms to 100 ms, 90 ms to 150 ms, 90 ms to 200 ms, 100 ms to 150 ms, 100 ms to 200 ms, or 150 ms to 200 ms. The device can detect facial expressions or motions within 10 ms, 20 ms, 30 ms, 40 ms, 50 ms, 60 ms, 70 ms, 80 ms, 90 ms, 100 ms, 150 ms, or 200 ms. The device can detect facial expressions or motions within at least 10 ms, 20 ms, 30 ms, 40 ms, 50 ms, 60 ms, 70 ms, 80 ms, 90 ms, 100 ms, or 150 ms. The device can detect facial expressions or motions within at most 20 ms, 30 ms, 40 ms, 50 ms, 60 ms, 70 ms, 80 ms, 90 ms, 100 ms, 150 ms, or 200 ms.

Disclosed herein are platforms, systems, devices, methods, and media that provide a machine learning framework for detecting emotional or social cues. Input data can include image and/or video data and optionally additional sensor data (e.g., accelerometer data, audio data, etc.). The input data is provided into an emotion detection system that detects or identifies emotional or social cues, which can be output to the user such as in real-time via a user interface on a computing device.

The emotion detection system includes artificial intelligence or machine learning model(s) trained to identify the emotional or social cues. In some instances, the system provides pre-processing of the data, a machine learning model or classifier, and optionally additional steps for processing or formatting the output. The output may be evaluated against one or more thresholds to place the input as falling within one or more of multiple social or emotional cue categories.

In some embodiments, the machine learning model is implemented as a regression model (e.g., providing a continuous output that may correlate with a degree of a social cue such as degree of anger). Alternatively, the model is implemented as a classification model (e.g., a categorical output indicating a smile or a frown is detected). In some instances, both types of models are implemented depending on the types of cues being detected.

In some instances, the emotion detection system comprises one or more modules for performing specific tasks necessary for the overall process to function. The emotion detection system can include a facial recognition module for detecting and tracking the faces of persons that are present in one or more images or video data and an expression or emotion detection module that evaluates the detected faces to identify the presence of one or more emotional or social cues. Additional modules may be present such as an audio module for processing any audio input (e.g., spoken words or verbal commands of the user), or other modules corresponding to additional sensor inputs. Various combinations of these modules are contemplated depending on the specific implementation of the emotion detection system.

Figure 38:
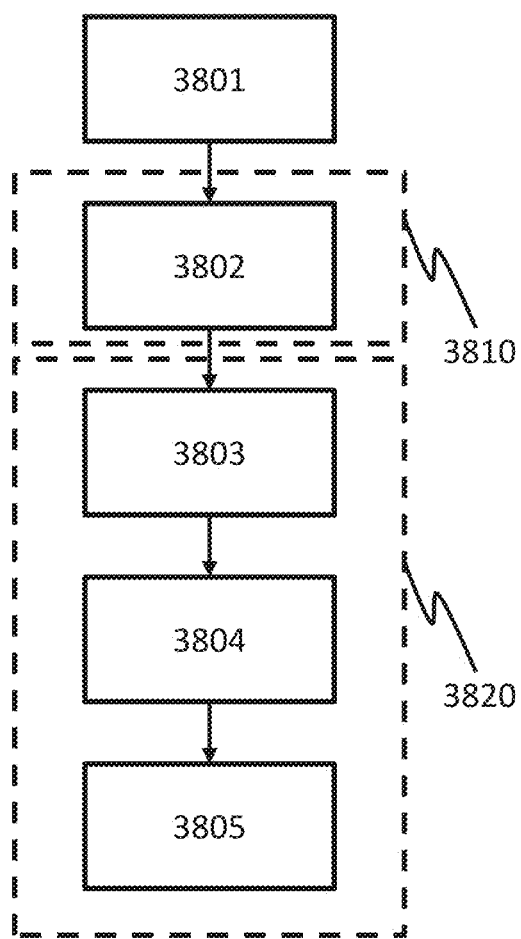
FIG. 38 shows a diagram of a facial recognition module and emotion detection module performing image or video analysis to detect emotional or social cues.

The facial recognition module 3810 and emotion detection module 3820 can together perform a series of steps such as illustrated in the non-limiting diagram shown in FIG. 38. First, the input data comprising image and/or video 3801 is provided. Facial detection is performed on the input data (e.g., for each image or frame of a video feed) 3802. This may include fiducial point face tracking or other processes useful for providing accurate face detection. The face may be normalized and/or registered against a standard size and/or position or angle. Other image processing techniques that may be applied include normalization of lighting. Next, a histogram of gradients feature extraction is generated for a region of interest on the face 3803. The facial expression is then classified to detect a social or emotional cue (e.g., smile, frown, anger, etc.) 3804. The classification may be carried out using a logistic regression machine learning model, which is trained on a training data set of labeled images. Finally, the output of the machine learning model can be filtered 3805, for example, using a filtering algorithm such as a moving average or a low-pass time-domain filter. This can help provide real-time social or emotional cue detection that remains steady over time by avoiding too many cues being detected from the image or video data. Various methods for providing real-time emotional or social cue detection can be employed. Examples include neutral subtraction for facial expression recognition that estimates the neutral face features in real-time and subtracts from extracted features, and classifying multiple images such as in a video feed and then averaging or smoothing them over time to mitigate noise. Various machine learning models can be used, for example, feed-forward convolutional neural networks used in conjunction with recurrent neural networks. This framework for social or emotional cue detection can be implemented on both input from an outward facing camera (e.g., target individual) and from an inward facing camera (e.g., the user). In addition, other input data sources such as sensor data can be incorporated into the analytical framework to improve emotion and social cue detection.

In some embodiments, the various modules of the emotion detection system is implemented using a multi-dimensional machine learning system. For example, a convolutional neural network can generate output directly based on input data such as pixel image data and optionally additional forms of input data. Various known approaches can perform object recognition, segmentation, and localization tasks without registration or image preprocessing. In addition, transfer learning can be used to improve emotion and social cue detection when a small amount of labeled data is available by generating a pre-trained neural network on publicly available image databases that is then fine-tuned using the small data set. then be applied to the domain of affective computing with a small amount of data.

In some embodiments, the emotion recognition system is configured to customize the social or emotional cue detection based on specific target individuals to improve emotion detection. For example, the system may label images identified as belonging to the same individual, which are used to provide a target-specific data set to help calibrate the machine learning model. The labels may be supplied by the user or a parent or caregiver, for example, a parent who is reviewing the images captured by the patient in order to apply the correct label or correct mistakes in the label. Accordingly, the machine learning model such as a convolutional neural network may be tweaked to adjust the weights between layers in order to improve accuracy for that particular individual. Thus, the accuracy can increase over time as more data is collected.

The digital therapeutics can comprise a social learning aid for a subject to increase cognitive performance such as, for example, facial engagement and/or recognition or providing feedback during social interactions. In some cases, the platforms, systems, devices, methods, and media disclosed herein provide an assessment tool comprising a survey or questionnaire to be completed by the subject or the subject's caretaker. The survey can include at least 5, 10, 15, 20, 25, 30, 35, 40, 45, 50, 55, 60, 65, 70, 80, 90, or 100 or more items and/or no more than 5, 10, 15, 20, 25, 30, 35, 40, 45, 50, 55, 60, 65, 70, 80, 90, or 100 or more items. These items can be categorized across a plurality of domains. In some cases, the items are categorized across two, three, four, or five social domains. The inputs or responses to these items can correspond to features utilized in the machine learning algorithms described herein such as trained evaluation or diagnostic models or classifiers. In some cases, the inputs or responses comprise a number or score. The score can be generated by summing up the items for each of the items. A score below a threshold can be interpreted as indicating or suggesting a disorder, delay, or impairment such as, for example, autism spectrum disorder.

In some cases, the platforms, systems, devices, methods, and media disclosed herein provide an assessment tool that measures various domains such as, for example, communication, daily living, socialization, motor functioning, and adaptive behavior skills. The assessment tool can be used to monitor the subject. For example, a higher score can indicate greater adaptive functioning.

In some embodiments, a method or device as described herein includes an evaluation aspect and a digital therapy aspect, wherein the evaluation together with the digital therapy together improve a social reciprocity of an individual receiving digital therapy. More specifically, in some embodiments, an evaluation on an individual using machine learning modeling selects for individuals who: (1) are in need of social reciprocity improvement and (2) will improve their social reciprocity considerably with the use of digital therapy. It is important to note that while certain individuals are capable of a therapeutic interaction with a digital therapy, certain individuals are not capable of benefiting from digital therapy due to, for example, cognitive deficits that prevent them from fully interacting with digital therapy to a therapeutic degree. Embodiments of the methods and devices described herein select for individuals who will benefit from digital therapy to a higher degree so that a digital therapy is only provided to these individuals, whereas individuals determined to not benefit from digital therapy are provided other treatment modalities. In some embodiments, an individual receiving a digital therapy is provided with a therapeutic agent or additional therapy that enhances his digital therapy experience by, for example, improving the cognition and/or attention of the individual during the digital therapy session.

The digital therapeutics can include social interaction sessions during which the subject engages in social interaction with the assistance of the social learning aid. In some instances, the personal treatment plan comprises one or more social interaction sessions. The social interaction sessions can be scheduled such as, for example, at least one, two, three, four, five, six, seven sessions per week. The digital therapeutics implemented as part of the personal treatment plan can be programmed to last at least one, two, three, four, five, six, seven, eight, nine, or ten or more weeks.

In some instances, the digital therapeutics are implemented using artificial intelligence. For example, an artificial intelligence-driven computing device such as a wearable device can be used to provide behavioral intervention to improve social outcomes for children with behavioral, neurological or mental health conditions or disorders. In some embodiments, the personalized treatment regimen is adaptive, for example, dynamically updating or reconfiguring its therapies based on captured feedback from the subject during ongoing therapy and/or additional relevant information (e.g., results from an autism evaluation).

Figure 1B:
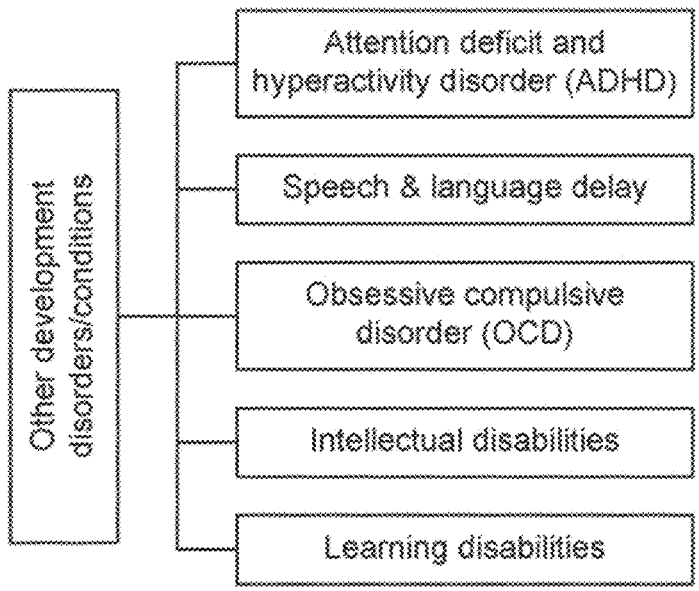

FIGS. 1A and 1B show some developmental disorders that may be evaluated using the assessment procedure as described herein. The assessment procedure can be configured to evaluate a subject's risk for having one or more developmental disorders, such as two or more related developmental disorders. The developmental disorders may have at least some overlap in symptoms or features of the subject. Such developmental disorders may include pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit and hyperactivity disorder (ADHD), speech and language delay, obsessive compulsive disorder (OCD), intellectual disability, learning disability, or any other relevant development disorder, such as disorders defined in any edition of the Diagnostic and Statistical Manual of Mental Disorders (DSM). The assessment procedure may be configured to determine the risk of the subject for having each of a plurality of disorders. The assessment procedure may be configured to determine the subject as at greater risk of a first disorder or a second disorder of the plurality of disorders. The assessment procedure may be configured to determine the subject as at risk of a first disorder and a second disorder with comorbidity. The assessment procedure may be configured to predict a subject to have normal development, or have low risk of having any of the disorders the procedure is configured to screen for. The assessment procedure may further be configured to have high sensitivity and specificity to distinguish among different severity ratings for a disorder; for example, the procedure may be configured to predict a subject's risk for having level 1 ASD, level 2 ASD, or level 3 ASD as defined in the fifth edition of the DSM (DSM-V).

Many developmental disorders may have similar or overlapping symptoms, thus complicating the assessment of a subject's developmental disorder. The assessment procedure described herein can be configured to evaluate a plurality of features of the subject that may be relevant to one or more developmental disorders. The procedure can comprise an assessment model that has been trained using a large set of clinically validated data to learn the statistical relationship between a feature of a subject and clinical diagnosis of one or more developmental disorders. Thus, as a subject participates in the assessment procedure, the subject's feature value for each evaluated feature (e.g., subject's answer to a question) can be queried against the assessment model to identify the statistical correlation, if any, of the subject's feature value to one or more screened developmental disorders. Based on the feature values provided by the subject, and the relationship between those values and the predicted risk for one or more developmental disorders as determined by the assessment model, the assessment procedure can dynamically adjust the selection of next features to be evaluated in the subject. The selection of the next feature to be evaluated may comprise an identification of the next most predictive feature, based on the determination of the subject as at risk for a particular disorder of the plurality of disorders being screened. For example, if after the subject has answered the first five questions of the assessment procedure, the assessment model predicts a low risk of autism and a relatively higher risk of ADHD in the subject, the assessment procedure may select features with higher relevance to ADHD to be evaluated next in the subject (e.g., questions whose answers are highly correlated with a clinical diagnosis of ADHD may be presented next to the subject). Thus, the assessment procedure described herein can be dynamically tailored to a particular subject's risk profile, and enable the evaluation of the subject's disorder with a high level of granularity.

Figure 2:
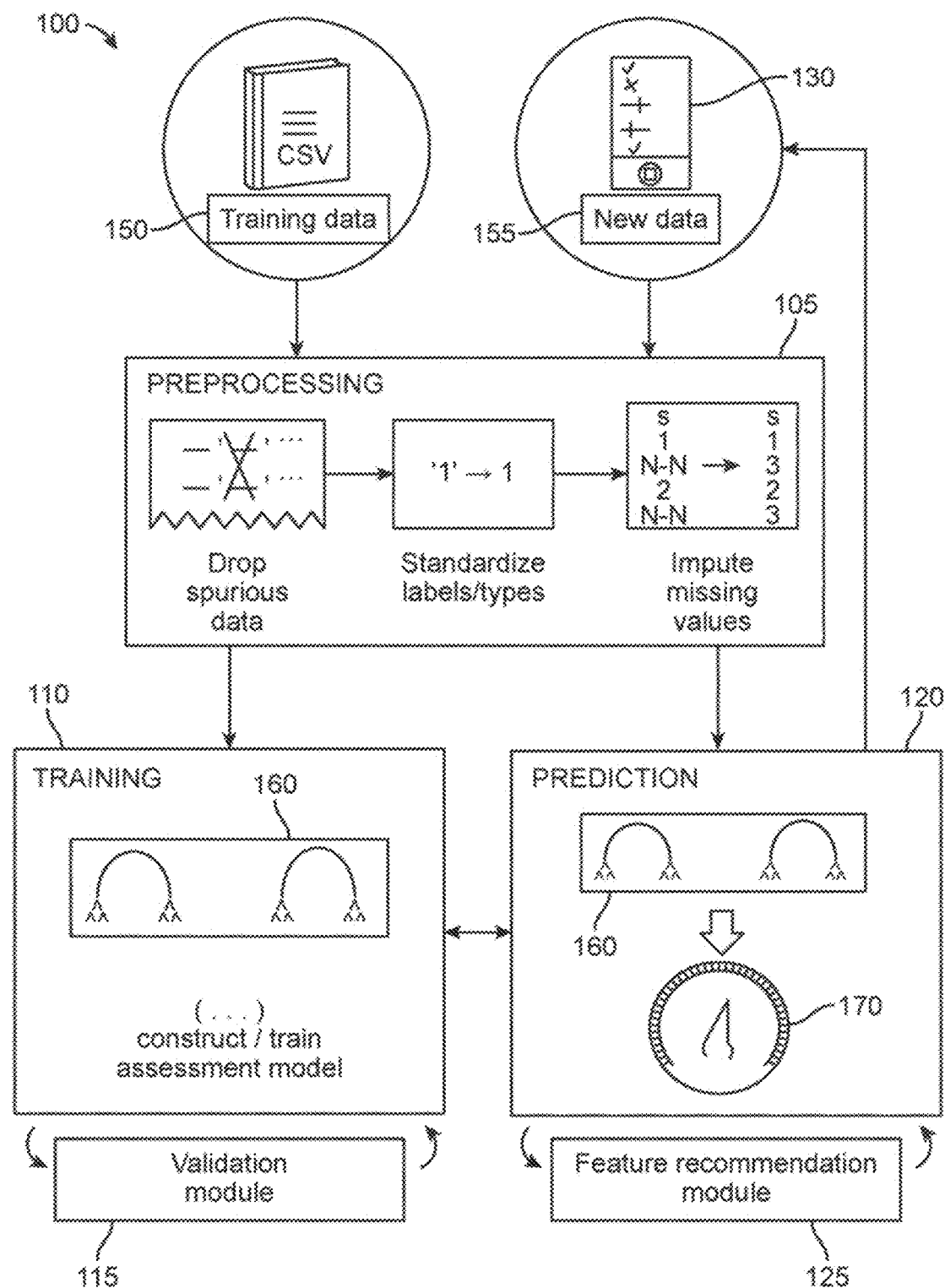
FIG. 2 is a schematic diagram of a data processing module for providing the assessment procedure as described herein.

FIG. 2 is a schematic diagram of a data processing module 100 for providing the assessment procedure as described herein. The data processing module 100 generally comprises a preprocessing module 105, a training module 110, and a prediction module 120. The data processing module can extract training data 150 from a database, or intake new data 155 with a user interface 130. The preprocessing module can apply one or more transformations to standardize the training data or new data for the training module or the prediction module. The preprocessed training data can be passed to the training module, which can construct an assessment model 160 based on the training data. The training module may further comprise a validation module 115, configured to validate the trained assessment model using any appropriate validation algorithm (e.g., Stratified K-fold cross-validation). The preprocessed new data can be passed on to the prediction module, which may output a prediction 170 of the subject's developmental disorder by fitting the new data to the assessment model constructed in the training module. The prediction module may further comprise a feature recommendation module 125, configured to select or recommend the next feature to be evaluated in the subject, based on previously provided feature values for the subject.

The training data 150, used by the training module to construct the assessment model, can comprise a plurality of datasets from a plurality of subjects, each subject's dataset comprising an array of features and corresponding feature values, and a classification of the subject's developmental disorder or condition. As described herein, the features may be evaluated in the subject via one or more of questions asked to the subject, observations of the subject, or structured interactions with the subject. Feature values may comprise one or more of answers to the questions, observations of the subject such as characterizations based on video images, or responses of the subject to a structured interaction, for example. Each feature may be relevant to the identification of one or more developmental disorders or conditions, and each corresponding feature value may indicate the degree of presence of the feature in the specific subject. For example, a feature may be the ability of the subject to engage in imaginative or pretend play, and the feature value for a particular subject may be a score of either 0, 1, 2, 3, or 8, wherein each score corresponds to the degree of presence of the feature in the subject (e.g., 0=variety of pretend play; 1=some pretend play; 2=occasional pretending or highly repetitive pretend play; 3=no pretend play; 8=not applicable). The feature may be evaluated in the subject by way of a question presented to the subject or a caretaker such as a parent, wherein the answer to the question comprises the feature value. Alternatively or in combination, the feature may be observed in the subject, for example with a video of the subject engaging in a certain behavior, and the feature value may be identified through the observation. In addition to the array of features and corresponding feature values, each subject's dataset in the training data also comprises a classification of the subject. For example, the classification may be autism, autism spectrum disorder (ASD), or non-spectrum. Preferably, the classification comprises a clinical diagnosis, assigned by qualified personnel such as licensed clinical psychologists, in order to improve the predictive accuracy of the generated assessment model. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 105 can be configured to apply one or more transformations to the extracted training data to clean and normalize the data, for example. The preprocessing module can be configured to discard features which contain spurious metadata or contain very few observations. The preprocessing module can be further configured to standardize the encoding of feature values. Different datasets may often have the same feature value encoded in different ways, depending on the source of the dataset. For example, '900', '900.0', '904', '904.0', '−1', '−1.0', 'None', and 'NaN' may all encode for a "missing" feature value. The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model. For example, for a categorical feature wherein the corresponding feature values are encoded as integers from 1 to 9, each integer value may have a different semantic content that is independent of the other values. For example, a value of '1' and a value of '9' may both be highly correlated with a specific classification, while a value of '5' is not. The original data representation of the feature value, wherein the feature value is encoded as the integer itself, may not be able to capture the unique semantic content of each value, since the values are represented in a linear model (e.g., an answer of '5' would place the subject squarely between a '1' and a '9' when the feature is considered in isolation; however, such an interpretation would be incorrect in the aforementioned case wherein a '1' and a '9' are highly correlated with a given classification while a '5' is not). To ensure that the semantic content of each feature value is captured in the construction of the assessment model, the preprocessing module may comprise instructions to re-encode certain feature values, such as feature values corresponding to categorical features, in a "one-hot" fashion, for example. In a "one-hot" representation, a feature value may be represented as an array of bits having a value of 0 or 1, the number of bits corresponding to the number of possible values for the feature. Only the feature value for the subject may be represented as a "1", with all other values represented as a "0". For example, if a subject answered "4" to a question whose possible answers comprise integers from 1 to 9, the original data representation may be [4], and the one-hot representation may be [0 0 0 1 0 0 0 0 0]. Such a one-hot representation of feature values can allow every value to be considered independently of the other possible values, in cases where such a representation would be necessary. By thus re-encoding the training data using the most appropriate data representation for each feature, the preprocessing module can improve the accuracy of the assessment model constructed using the training data.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module. For features having categorical feature values (e.g., extent of display of a certain behavior in the subject), missing values can be provided as appropriate data representations specifically designated as such. For example, if the categorical features are encoded in a one-hot representation as described herein, the preprocessing module may encode a missing categorical feature value as an array of '0' bits. For features having continuous feature values (e.g., age of the subject), the mean of all of the possible values can be provided in place of the missing value (e.g., age of 4 years).

The training module 110 can utilize a machine learning algorithm or other algorithm to construct and train an assessment model to be used in the assessment procedure, for example. An assessment model can be constructed to capture, based on the training data, the statistical relationship, if any, between a given feature value and a specific developmental disorder to be screened by the assessment procedure. The assessment model may, for example, comprise the statistical correlations between a plurality of clinical characteristics and clinical diagnoses of one or more developmental disorders. A given feature value may have a different predictive utility for classifying each of the plurality of developmental disorders to be evaluated in the assessment procedure. For example, in the aforementioned example of a feature comprising the ability of the subject to engage in imaginative or pretend play, the feature value of "3" or "no variety of pretend play" may have a high predictive utility for classifying autism, while the same feature value may have low predictive utility for classifying ADHD. Accordingly, for each feature value, a probability distribution may be extracted that describes the probability of the specific feature value for predicting each of the plurality of developmental disorders to be screened by the assessment procedure. The machine learning algorithm can be used to extract these statistical relationships from the training data and build an assessment model that can yield an accurate prediction of a developmental disorder when a dataset comprising one or more feature values is fitted to the model.

One or more machine learning algorithms may be used to construct the assessment model, such as support vector machines that deploy stepwise backwards feature selection and/or graphical models, both of which can have advantages of inferring interactions between features. For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once an assessment model is derived from the training data, the model may be used as a prediction tool to assess the risk of a subject for having one or more developmental disorders. Machine learning analyses may be performed using one or more of many programming languages and platforms known in the art, such as R, Weka, Python, and/or Matlab, for example.

A Random Forest classifier, which generally comprises a plurality of decision trees wherein the output prediction is the mode of the predicted classifications of the individual trees, can be helpful in reducing overfitting to training data. An ensemble of decision trees can be constructed using a random subset of features at each split or decision node. The Gini criterion may be employed to choose the best partition, wherein decision nodes having the lowest calculated Gini impurity index are selected. At prediction time, a "vote" can be taken over all of the decision trees, and the majority vote (or mode of the predicted classifications) can be output as the predicted classification.

Figure 3:
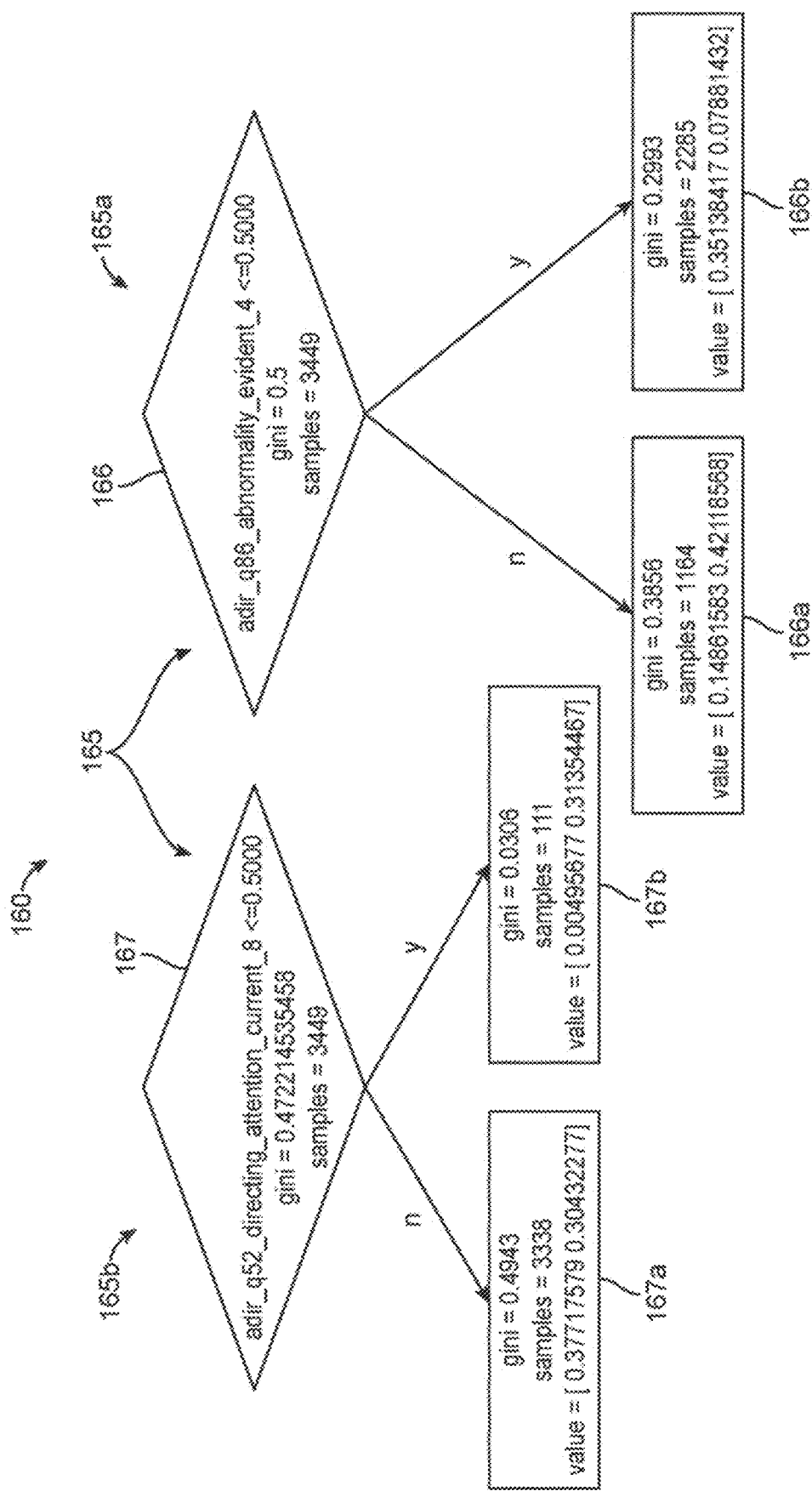
FIG. 3 is a schematic diagram illustrating a portion of an assessment model based on a Random Forest classifier.

FIG. 3 is a schematic diagram illustrating a portion of an assessment model 160 based on a Random Forest classifier. The assessment module may comprise a plurality of individual decision trees 165, such as decision trees 165a and 165b, each of which can be generated independently using a random subset of features in the training data. Each decision tree may comprise one or more decision nodes such as decision nodes 166 and 167 shown in FIG. 3, wherein each decision node specifies a predicate condition. For example, decision node 16 predicates the condition that, for a given dataset of an individual, the answer to question #86 (age when abnormality is first evident) is 4 or less. Decision node 167 predicates the condition that, for the given dataset, the answer to question #52 (showing and direction attention) is 8 or less. At each decision node, a decision tree can be split based on whether the predicate condition attached to the decision node holds true, leading to prediction nodes (e.g., 166a, 166b, 167a, 167b). Each prediction node can comprise output values ('value' in FIG. 3) that represent "votes" for one or more of the classifications or conditions being evaluated by the assessment model. For example, in the prediction nodes shown in FIG. 3, the output values comprise votes for the individual being classified as having autism or being non-spectrum. A prediction node can lead to one or more additional decision nodes downstream (not shown in FIG. 3), each decision node leading to an additional split in the decision tree associated with corresponding prediction nodes having corresponding output values. The Gini impurity can be used as a criterion to find informative features based on which the splits in each decision tree may be constructed. An assessment model can be configured to detect or evaluate a subject for the presence of a disorder or condition. In some cases, a separate assessment model is configured to determine whether a subject having the disorder or condition will be improved by a digital therapy, for example, a digital therapy configured to promote social reciprocity.

When the dataset being queried in the assessment model reaches a "leaf", or a final prediction node with no further downstream splits, the output values of the leaf can be output as the votes for the particular decision tree. Since the Random Forest model comprises a plurality of decision trees, the final votes across all trees in the forest can be summed to yield the final votes and the corresponding classification of the subject. While only two decision trees are shown in FIG. 3, the model can comprise any number of decision trees. A large number of decision trees can help reduce overfitting of the assessment model to the training data, by reducing the variance of each individual decision tree. For example, the assessment model can comprise at least about 10 decision trees, for example at least about 100 individual decision trees or more.

An ensemble of linear classifiers may also be suitable for the derivation of an assessment model as described herein. Each linear classifier can be individually trained with a stochastic gradient descent, without an "intercept term". The lack of an intercept term can prevent the classifier from deriving any significance from missing feature values. For example, if a subject did not answer a question such that the feature value corresponding to said question is represented as an array of '0' bits in the subject's data set, the linear classifier trained without an intercept term will not attribute any significance to the array of '0' bits. The resultant assessment model can thereby avoid establishing a correlation between the selection of features or questions that have been answered by the subject and the final classification of the subject as determined by the model. Such an algorithm can help ensure that only the subject-provided feature values or answers, rather than the features or questions, are factored into the final classification of the subject.

The training module may comprise feature selection. One or more feature selection algorithms (such as support vector machine, convolutional neural nets) may be used to select features able to differentiate between individuals with and without certain developmental disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific developmental disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data. To reduce sample bias in constructing an assessment model using skewed training data, sample weighting may be applied in training the assessment model. Sample weighting can comprise lending a relatively greater degree of significance to a specific set of samples during the model training process. For example, during model training, if the training data is skewed towards individuals diagnosed with autism, higher significance can be attributed to the data from individuals not diagnosed with autism (e.g., up to 50 times more significance than data from individuals diagnosed with autism). Such a sample weighting technique can substantially balance the sample bias present in the training data, thereby producing an assessment model with reduced bias and improved accuracy in classifying data in the real world. To further reduce the contribution of training data sample bias to the generation of an assessment model, a boosting technique may be implemented during the training process. Boosting comprises an iterative process, wherein after one iteration of training, the weighting of each sample data point is updated. For example, samples that are misclassified after the iteration can be updated with higher significances. The training process may then be repeated with the updated weightings for the training data.

The training module may further comprise a validation module 115 configured to validate the assessment model constructed using the training data. For example, a validation module may be configured to implement a Stratified K-fold cross validation, wherein k represents the number of partitions that the training data is split into for cross validation. For example, k can be any integer greater than 1, such as 3, 4, 5, 6, 7, 8, 9, or 10, or possibly higher depending on risk of overfitting the assessment model to the training data.

The training module may be configured to save a trained assessment model to a local memory and/or a remote server, such that the model can be retrieved for modification by the training module or for the generation of a prediction by the prediction module 120.

Figure 4:
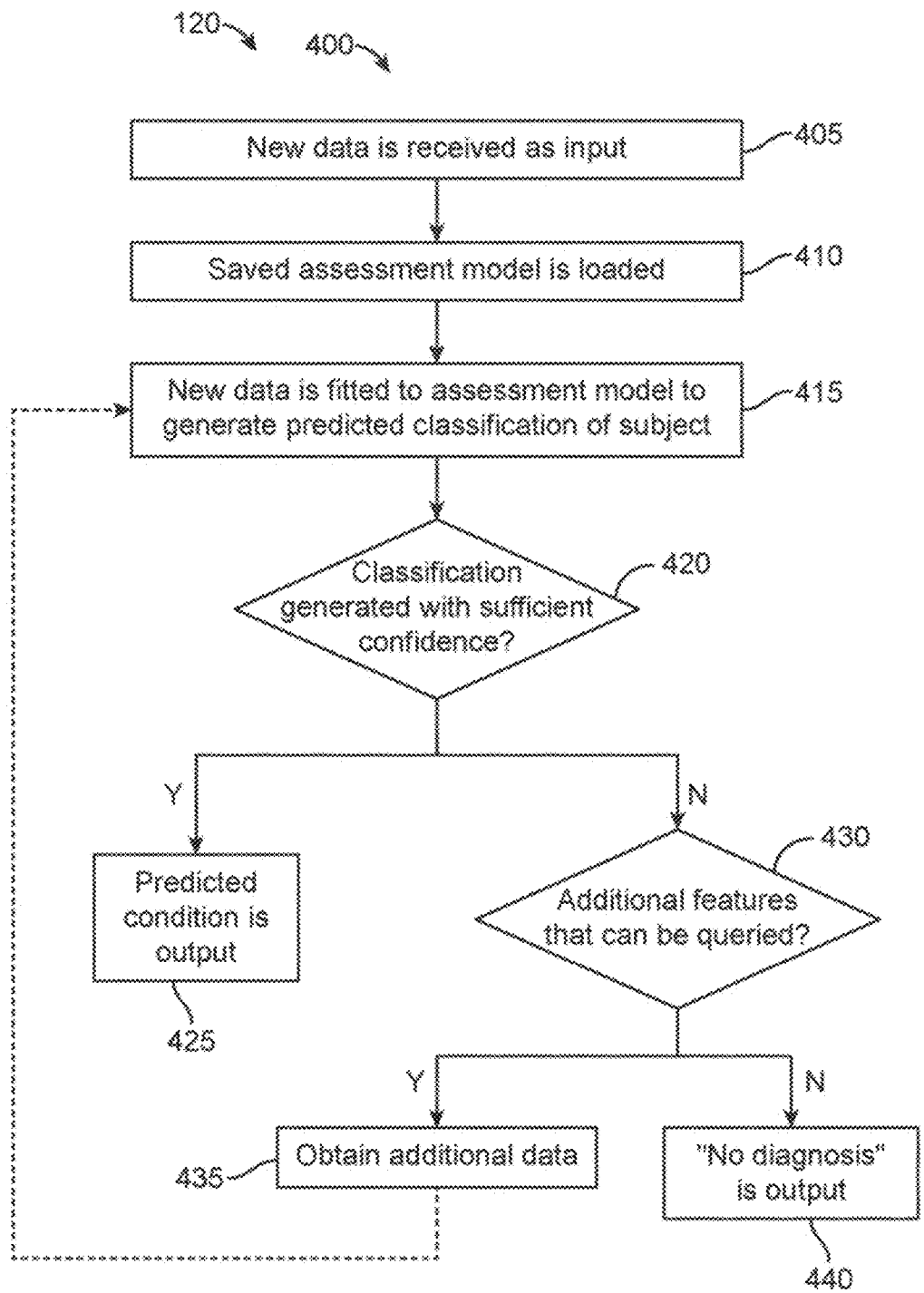
FIG. 4 is an operational flow of a prediction module as described herein.

FIG. 4 is an operational flow 400 of a method of a prediction module 120 as described herein. The prediction module 120 can be configured to generate a predicted classification (e.g., developmental disorder) of a given subject, by fitting new data to an assessment model constructed in the training module. At step 405, the prediction module can receive new data that may have been processed by the preprocessing module to standardize the data, for example by dropping spurious metadata, applying uniform encoding of feature values, re-encoding select features using different data representations, and/or imputing missing data points, as described herein. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The new data provided to the prediction module may or may not have a known classification or diagnosis associated with the data; either way, the prediction module may not use any pre-assigned classification information in generating the predicted classification for the subject. The new data may comprise a previously-collected, complete dataset for a subject to be diagnosed or assessed for the risk of having one or more of a plurality of developmental disorders. Alternatively or in combination, the new data may comprise data collected in real time from the subject or a caretaker of the subject, for example with a user interface as described in further detail herein, such that the complete dataset can be populated in real time as each new feature value provided by the subject is sequentially queried against the assessment model.

At step 410, the prediction module can load a previously saved assessment model, constructed by the training module, from a local memory and/or a remote server configured to store the model. At step 415, the new data is fitted to the assessment model to generate a predicted classification of the subject. At step 420, the module can check whether the fitting of the data can generate a prediction of one or more specific disorders (e.g., autism, ADHD, etc.) within a confidence interval exceeding a threshold value, for example within a 90% or higher confidence interval, for example 95% or more. If so, as shown in step 425, the prediction module can output the one or more developmental disorders as diagnoses of the subject or as disorders for which the subject is at risk. The prediction module may output a plurality of developmental disorders for which the subject is determined to at risk beyond the set threshold, optionally presenting the plurality of disorders in order of risk. The prediction module may output one developmental disorder for which the subject is determined to be at greatest risk. The prediction module may output two or more development disorders for which the subject is determined to risk with comorbidity. The prediction module may output determined risk for each of the one or more developmental disorders in the assessment model. If the prediction module cannot fit the data to any specific developmental disorder within a confidence interval at or exceeding the designated threshold value, the prediction module may determine, in step 430, whether there are any additional features that can be queried. If the new data comprises a previously-collected, complete dataset, and the subject cannot be queried for any additional feature values, "no diagnosis" may be output as the predicted classification, as shown in step 440. If the new data comprises data collected in real time from the subject or caretaker during the prediction process, such that the dataset is updated with each new input data value provided to the prediction module and each updated dataset is fitted to the assessment model, the prediction module may be able to query the subject for additional feature values. If the prediction module has already obtained data for all features included in the assessment module, the prediction module may output "no diagnosis" as the predicted classification of the subject, as shown in step 440. If there are features that have not yet been presented to the subject, as shown in step 435, the prediction module may obtain additional input data values from the subject, for example by presenting additional questions to the subject. The updated dataset including the additional input data may then be fitted to the assessment model again (step 415), and the loop may continue until the prediction module can generate an output.

Figure 5:
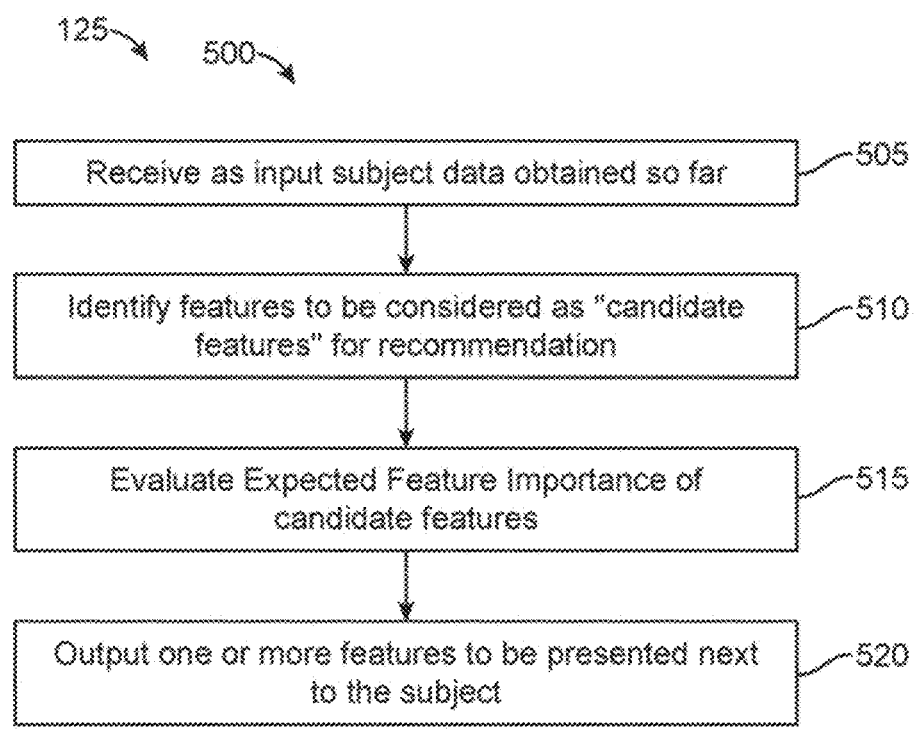
FIG. 5 is an operational flow of a feature recommendation module as described herein.

FIG. 5 is an operational flow 500 of a feature recommendation module 125 as described herein by way of a non-limiting example. The prediction module may comprise a feature recommendation module 125, configured to identify, select or recommend the next most predictive or relevant feature to be evaluated in the subject, based on previously provided feature values for the subject. For example, the feature recommendation module can be a question recommendation module, wherein the module can select the most predictive next question to be presented to a subject or caretaker, based on the answers to previously presented questions. The feature recommendation module can be configured to recommend one or more next questions or features having the highest predictive utility in classifying a particular subject's developmental disorder. The feature recommendation module can thus help to dynamically tailor the assessment procedure to the subject, so as to enable the prediction module to produce a prediction with a reduced length of assessment and improved sensitivity and accuracy. Further, the feature recommendation module can help improve the specificity of the final prediction generated by the prediction module, by selecting features to be presented to the subject that are most relevant in predicting one or more specific developmental disorders that the particular subject is most likely to have, based on feature values previously provided by the subject.

At step 505, the feature recommendation module can receive as input the data already obtained from the subject in the assessment procedure. The input subject data can comprise an array of features and corresponding feature values provided by the subject. At step 510, the feature recommendation module can select one or more features to be considered as "candidate features" for recommendation as the next feature(s) to be presented to one or more of the subject, caretaker or clinician. Features that have already been presented can be excluded from the group of candidate features to be considered. Optionally, additional features meeting certain criteria may also be excluded from the group of candidate features, as described in further detail herein.

At step 515, the feature recommendation module can evaluate the "expected feature importance" of each candidate feature. The candidate features can be evaluated for their "expected feature importance", or the estimated utility of each candidate feature in predicting a specific developmental disorder for the specific subject. The feature recommendation module may utilize an algorithm based on: (1) the importance or relevance of a specific feature value in predicting a specific developmental disorder; and (2) the probability that the subject may provide the specific feature value. For example, if the answer of "3" to question B5 is highly correlated with a classification of autism, this answer can be considered a feature value having high utility for predicting autism. If the subject at hand also has a high probability of answering "3" to said question B5, the feature recommendation module can determine this question to have high expected feature importance. An algorithm that can be used to determine the expected feature importance of a feature is described in further detail in reference to FIG. 6, for example.

At step 520, the feature recommendation module can select one or more candidate features to be presented next to the subject, based on the expected feature importance of the features as determined in step 515. For example, the expected feature importance of each candidate feature may be represented as a score or a real number, which can then be ranked in comparison to other candidate features. The candidate feature having the desired rank, for example a top 10, top 5, top 3, top 2, or the highest rank, may be selected as the feature to the presented next to the subject.

Figure 6:
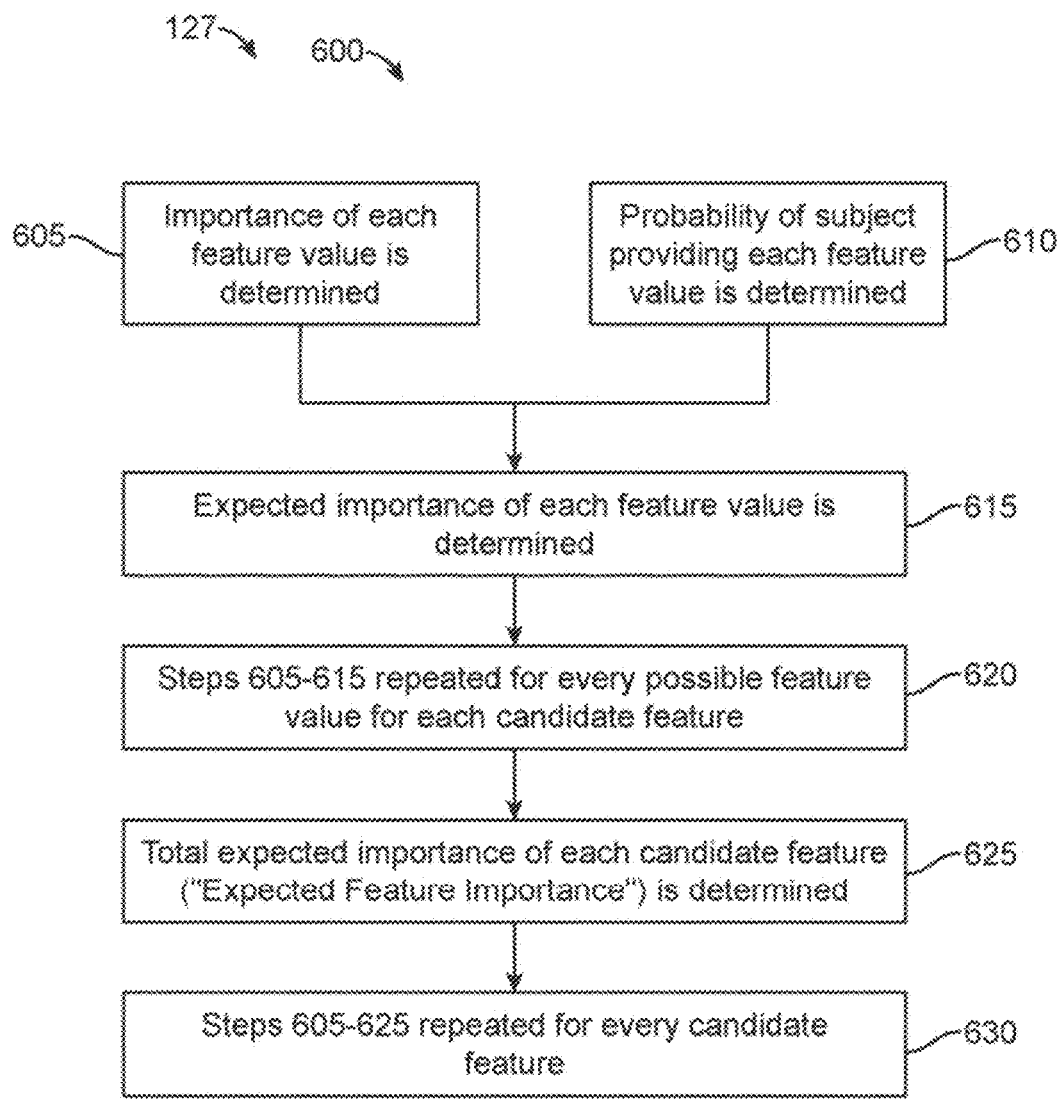
FIG. 6 is an operational flow of an expected feature importance determination algorithm as performed by a feature recommendation module described herein.

FIG. 6 is an operational flow 600 of method of determining an expected feature importance determination algorithm 127 as performed by a feature recommendation module 125 described herein.

At step 605, the algorithm can determine the importance or relevance of a specific feature value in predicting a specific developmental disorder. The importance or relevance of a specific feature value in predicting a specific developmental disorder can be derived from the assessment model constructed using training data. Such a "feature value importance" can be conceptualized as a measure of how relevant a given feature value's role is, should it be present or not present, in determining a subject's final classification. For example, if the assessment model comprises a Random Forest classifier, the importance of a specific feature value can be a function of where that feature is positioned in the Random Forest classifier's branches. Generally, if the average position of the feature in the decision trees is relatively high, the feature can have relatively high feature importance. The importance of a feature value given a specific assessment model can be computed efficiently, either by the feature recommendation module or by the training module, wherein the training module may pass the computed statistics to the feature recommendation module. Alternatively, the importance of a specific feature value can be a function of the actual prediction confidence that would result if said feature value was provided by the subject. For each possible feature value for a given candidate feature, the feature recommendation module can be configured to calculate the actual prediction confidence for predicting one or more developmental disorders, based on the subject's previously provided feature values and the currently assumed feature value.

Each feature value may have a different importance for each developmental disorder for which the assessment procedure is designed to screen. Accordingly, the importance of each feature value may be represented as a probability distribution that describes the probability of the feature value yielding an accurate prediction for each of the plurality of developmental disorders being evaluated.

At step 610, the feature recommendation module can determine the probability of a subject providing each feature value. The probability that the subject may provide a specific feature value can be computed using any appropriate statistical model. For example, a large probabilistic graphical model can be used to find the values of expressions such as:

$$\text{prob}(E=1 | A=1, B=2, C=1)$$

where A, B, and C represent different features or questions in the prediction module and the integers 1 and 2 represent different possible feature values for the feature (or possible answers to the questions). The probability of a subject providing a specific feature value may then be computed using Bayes' rule, with expressions such as:

$$\text{prob}(E=1 | A=1, B=2, C=1) = \text{prob}(E=1, A=1, B=2, C=1) / \text{prob}(A=1, B=2, C=1)$$

Such expressions may be computationally expensive, in terms of both computation time and required processing resources. Alternatively or in combination with computing the probabilities explicitly using Bayes' rule, logistic regression or other statistical estimators may be used, wherein the probability is estimated using parameters derived from a machine learning algorithm. For example, the following expression may be used to estimate the probability that the subject may provide a specific feature value:

$$\text{prob}(E=1 | A=1, B=2, C=1) \approx \text{sigmoid}(a1^*A + a2^*B + a3^*C + a4),$$

wherein a1, a2, a3, and a4 are constant coefficients determined from the trained assessment model, learned using an optimization algorithm that attempts to make this expression maximally correct, and wherein sigmoid is a nonlinear function that enables this expression to be turned into a probability. Such an algorithm can be quick to train, and the resulting expressions can be computed quickly in application, e.g., during administration of the assessment procedure. Although reference is made to four coefficients, as many coefficients as are helpful may be used as will be recognized by a person of ordinary skill in the art.

At step 615, the expected importance of each feature value can be determined based on a combination of the metrics calculated in steps 605 and 610. Based on these two factors, the feature recommendation module can determine the expected utility of the specific feature value in predicting a specific developmental disorder. Although reference is made herein to the determination of expected importance via multiplication, the expected importance can be determined by combining coefficients and parameters in many ways, such as with look up tables, logic, or division, for example.

At step 620, steps 605-615 can be repeated for every possible feature value for each candidate feature. For example, if a particular question has 4 possible answers, the expected importance of each of the 4 possible answers is determined.

At step 625, the total expected importance, or the expected feature importance, of each candidate feature can be determined. The expected feature importance of each feature can be determined by summing the feature value importances of every possible feature value for the feature, as determined in step 620. By thus summing the expected utilities across all possible feature values for a given feature, the feature recommendation module can determine the total expected feature importance of the feature for predicting a specific developmental disorder in response to previous answers.

At step 630, steps 605-625 can be repeated for every candidate feature being considered by the feature recommendation module. The candidate features may comprise a subset of possible features such as questions. Thus, an expected feature importance score for every candidate feature can be generated, and the candidate features can be ranked in order of highest to lowest expected feature importance.

Optionally, in addition to the two factors determined in steps 605 and 610, a third factor may also be taken into account in determining the importance of each feature value. Based on the subject's previously provided feature values, the subject's probability of having one or more of the plurality of developmental disorders can be determined. Such a probability can be determined based on the probability distribution stored in the assessment model, indicating the probability of the subject having each of the plurality of screened developmental disorders based on the feature values provided by the subject. In selecting the next feature to be presented to the subject, the algorithm may be configured to give greater weight to the feature values most important or relevant to predicting the one or more developmental disorders that the subject at hand is most likely to have. For example, if a subject's previously provided feature values indicate that the subject has a higher probability of having either an intellectual disability or speech and language delay than any of the other developmental disorders being evaluated, the feature recommendation module can favor feature values having high importance for predicting either intellectual disability or speech and language delay, rather than features having high importance for predicting autism, ADHD, or any other developmental disorder that the assessment is designed to screen for. The feature recommendation module can thus enable the prediction module to tailor the prediction process to the subject at hand, presenting more features that are relevant to the subject's potential developmental disorder to yield a final classification with higher granularity and confidence.

Although the above steps show an operational flow 600 of an expected feature importance determination algorithm 127, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

A non-limiting implementation of the feature recommendation module is now described. Subject X has provided answers (feature values) to questions (features) A, B, and C in the assessment procedure:

$$\text{Subject } X = \{`A`:1, `B`:2, `C`:1\}$$

The feature recommendation module can determine whether question D or question E should be presented next in order to maximally increase the predictive confidence with which a final classification or diagnosis can be reached. Given Subject X's previous answers, the feature recommendation module determines the probability of Subject X providing each possible answer to each of questions D and E, as follows:

$$\text{prob}(E=1|A=1, B=2, C=1)=0.1$$

$$\text{prob}(E=2|A=1, B=2, C=1)=0.9$$

$$\text{prob}(D=1|A=1, B=2, C=1)=0.7$$

$$\text{prob}(D=2|A=1, B=2, C=1)=0.3$$

The feature importance of each possible answer to each of questions D and E can be computed based on the assessment model as described. Alternatively, the feature importance of each possible answer to each of questions D and E can be computed as the actual prediction confidence that would result if the subject were to give the specific answer. The importance of each answer can be represented using a range of values on any appropriate numerical scale. For example:

$$\text{importance}(E=1)=1$$

$$\text{importance}(E=2)=3$$

$$\text{importance}(D=1)=2$$

$$\text{importance}(D=2)=4$$

Based on the computed probabilities and the feature value importances, the feature recommendation module can compute the expected feature importance of each question as follows:

$$\begin{aligned}\text{Exceptation}[\text{importance}(E)] &= (prob(E=2|A=1, B=2, C=1)* \\ &\quad \text{importance}(E=2) + \\ &= 0.1*1 + 0.9*3 \\ &= 2.8\end{aligned}$$

$$\begin{aligned}\text{Expectation}[\text{importance}(D)] &= (prob(D=1|A=1, B=2, C=1)* \\ &\quad \text{importance}(D=1) + \\ &\quad (prob(D=2|A=1, B=2, C=1)* \\ &\quad \text{importance}(D=2) \\ &= 0.7*2 + 0.3*4 \\ &= 2.6\end{aligned}$$

Hence, the expected feature importance (also referred to as relevance) from the answer of question E is determined to be higher than that of question D, even though question D has generally higher feature importances for its answers. The feature recommendation module can therefore select question E as the next question to be presented to Subject X.

When selecting the next best feature to be presented to a subject, the feature recommendation module 125 may be further configured to exclude one or more candidate features from consideration, if the candidate features have a high co-variance with a feature that has already been presented to the subject. The co-variance of different features may be determined based on the training data, and may be stored in the assessment model constructed by the training module. If a candidate feature has a high co-variance with a previously presented feature, the candidate feature may add relatively little additional predictive utility, and may hence be omitted from future presentation to the subject in order to optimize the efficiency of the assessment procedure.

The prediction module 120 may interact with the person participating in the assessment procedure (e.g., a subject or the subject's caretaker) with a user interface 130. The user interface may be provided with a user interface, such as a display of any computing device that can enable the user to access the prediction module, such as a personal computer, a tablet, or a smartphone. The computing device may comprise a processor that comprises instructions for providing the user interface, for example in the form of a mobile application. The user interface can be configured to display instructions from the prediction module to the user, and/or receive input from the user with an input method provided by the computing device. Thus, the user can participate in the assessment procedure as described herein by interacting with the prediction module with the user interface, for example by providing answers (feature values) in response to questions (features) presented by the prediction module. The user interface may be configured to administer the assessment procedure in real-time, such that the user answers one question at a time and the prediction module can select the next best question to ask based on recommendations made by the feature recommendation module. Alternatively or in combination, the user interface may be configured to receive a complete set of new data from a user, for example by allowing a user to upload a complete set of feature values corresponding to a set of features.

As described herein, the features of interest relevant to identifying one or more developmental disorders may be evaluated in a subject in many ways. For example, the subject or caretaker or clinician may be asked a series of questions designed to assess the extent to which the features of interest are present in the subject. The answers provided can then represent the corresponding feature values of the subject. The user interface may be configured to present a series of questions to the subject (or any person participating in the assessment procedure on behalf of the subject), which may be dynamically selected from a set of candidate questions as described herein. Such a question-and-answer based assessment procedure can be administered entirely by a machine, and can hence provide a very quick prediction of the subject's developmental disorder(s).

Alternatively or in combination, features of interest in a subject may be evaluated with observation of the subject's behaviors, for example with videos of the subject. The user interface may be configured to allow a subject or the subject's caretaker to record or upload one or more videos of the subject. The video footage may be subsequently analyzed by qualified personnel to determine the subject's feature values for features of interest. Alternatively or in combination, video analysis for the determination of feature values may be performed by a machine. For example, the video analysis may comprise detecting objects (e.g., subject, subject's spatial position, face, eyes, mouth, hands, limbs, fingers, toes, feet, etc.), followed by tracking the movement of the objects. The video analysis may infer the gender of the subject, and/or the proficiency of spoken language(s) of the subject. The video analysis may identify faces globally, or specific landmarks on the face such as the nose, eyes, lips and mouth to infer facial expressions and track these expressions over time. The video analysis may detect eyes, limbs, fingers, toes, hands, feet, and track their movements over time to infer behaviors. In some cases, the analysis may further infer the intention of the behaviors, for example, a child being upset by noise or loud music, engaging in self-harming behaviors, imitating another person's actions, etc. The sounds and/or voices recorded in the video files may also be analyzed. The analysis may infer a context of the subject's behavior. The sound/voice analysis may infer a feeling of the subject. The analysis of a video of a subject, performed by a human and/or by a machine, can yield feature values for the features of interest, which can then be encoded appropriately for input into the prediction module. A prediction of the subject's developmental disorder may then be generated based on a fitting of the subject's feature values to the assessment model constructed using training data.

Alternatively or in combination, features of interest in a subject may be evaluated through structured interactions with the subject. For example, the subject may be asked to play a game such as a computer game, and the performance of the subject on the game may be used to evaluate one or more features of the subject. The subject may be presented with one or more stimuli (e.g., visual stimuli presented to the subject via a display), and the response of the subject to the stimuli may be used to evaluate the subject's features. The subject may be asked to perform a certain task (e.g., subject may be asked to pop bubbles with his or her fingers), and the response of the subject to the request or the ability of the subject to carry out the requested task may be used to evaluate to the subject's features.

The methods and devices described herein can be configured in many ways to determine the next most predictive or relevant question. At least a portion of the software instructions as described herein can be configured to run locally on a local device so as to provide the user interface and present questions and receive answers to the questions. The local device can be configured with software instructions of an application program interface (API) to query a remote server for the most predictive next question. The API can return an identified question based on the feature importance as described herein, for example. Alternatively or in combination, the local processor can be configured with instructions to determine the most predictive next question in response to previous answers. For example, the prediction module 120 may comprise software instructions of a remote server, or software instructions of a local processor, and combinations thereof. Alternatively or in combination, the feature recommendation module 125 may comprise software instructions of a remote server, or software instructions of a local processor, and combinations thereof, configured to determine the most predictive next question, for example. The operational flow 600 of method of determining an expected feature importance determination algorithm 127 as performed by a feature recommendation module 125 described herein can be performed with one or more processors as described herein, for example.

Figure 7:
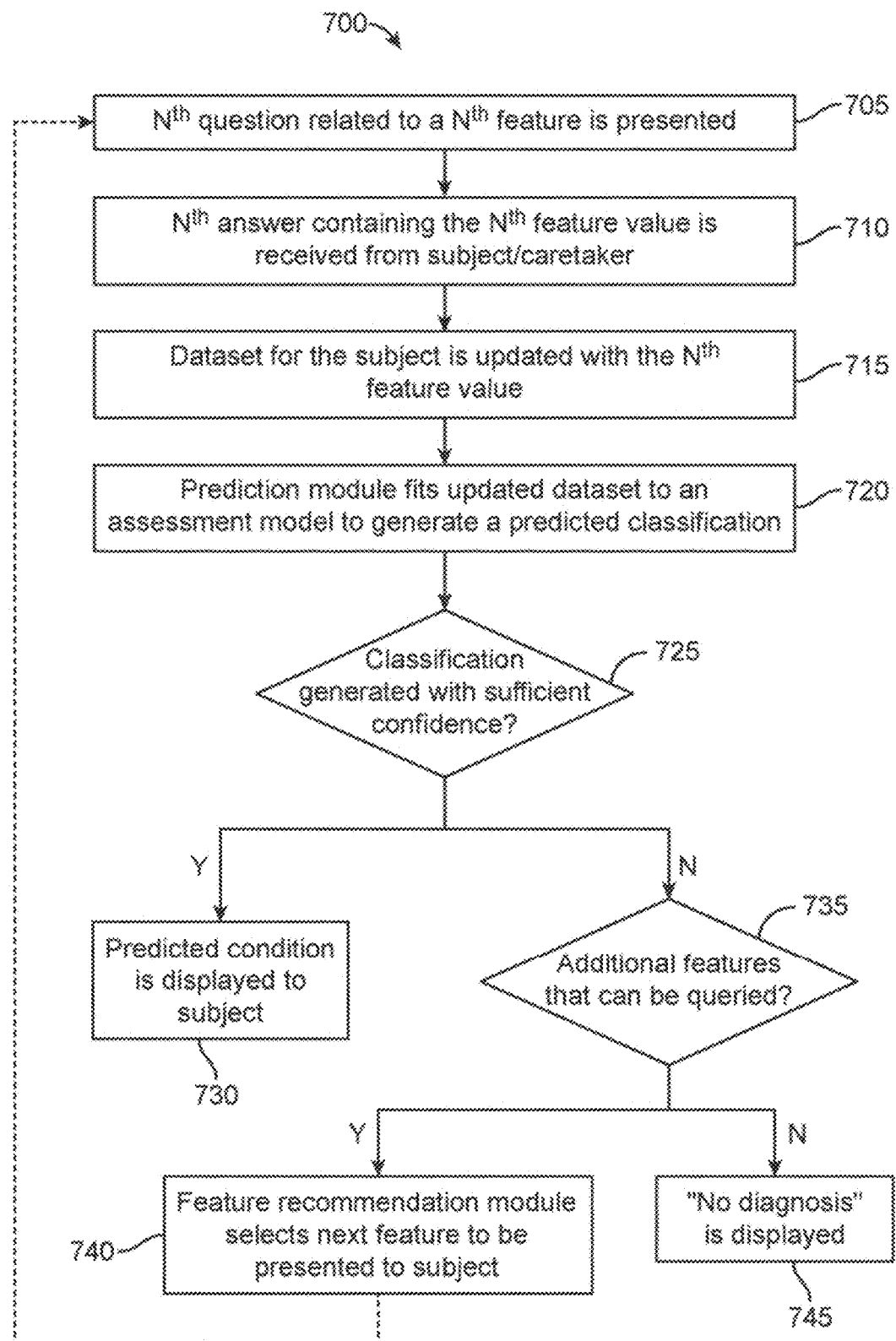
FIG. 7 illustrates a method of administering an assessment procedure as described herein.

FIG. 7 illustrates a method 700 of administering an assessment procedure as described herein. The method 700 may be performed with a user interface provided on a computing device, the computing device comprising a display and a user interface for receiving user input in response to the instructions provided on the display. The user participating in the assessment procedure may be the subject himself, or another person participating in the procedure on behalf of the subject, such as the subject's caretaker. At step 705, an $N^{th}$ question related an $N^{th}$ feature can be presented to the user with the display. At step 710, the subject's answer containing the corresponding $N^{th}$ feature value can be received. At step 715, the dataset for the subject at hand can be updated to include $N^{th}$ the feature value provided for the subject. At step 720, the updated dataset can be fitted to an assessment model to generate a predicted classification. Step 720 may be performed by a prediction module, as described herein. At step 725, a check can be performed to determine whether the fitting of the data can generate a prediction of a specific developmental disorder (e.g., autism, ADHD, etc.) sufficient confidence (e.g., within at least a 90% confidence interval). If so, as shown at step 730, the predicted developmental disorder can be displayed to the user. If not, in step 735, a check can be performed to determine whether there are any additional features that can be queried. If yes, as shown at step 740, the feature recommendation module may select the next feature to be presented to the user, and steps 705-725 may be repeated until a final prediction (e.g., a specific developmental disorder or "no diagnosis") can be displayed to the subject. If no additional features can be presented to the subject, "no diagnosis" may be displayed to the subject, as shown at step 745.

Although the above steps show a non-limiting method 700 of administering an assessment procedure, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 8:
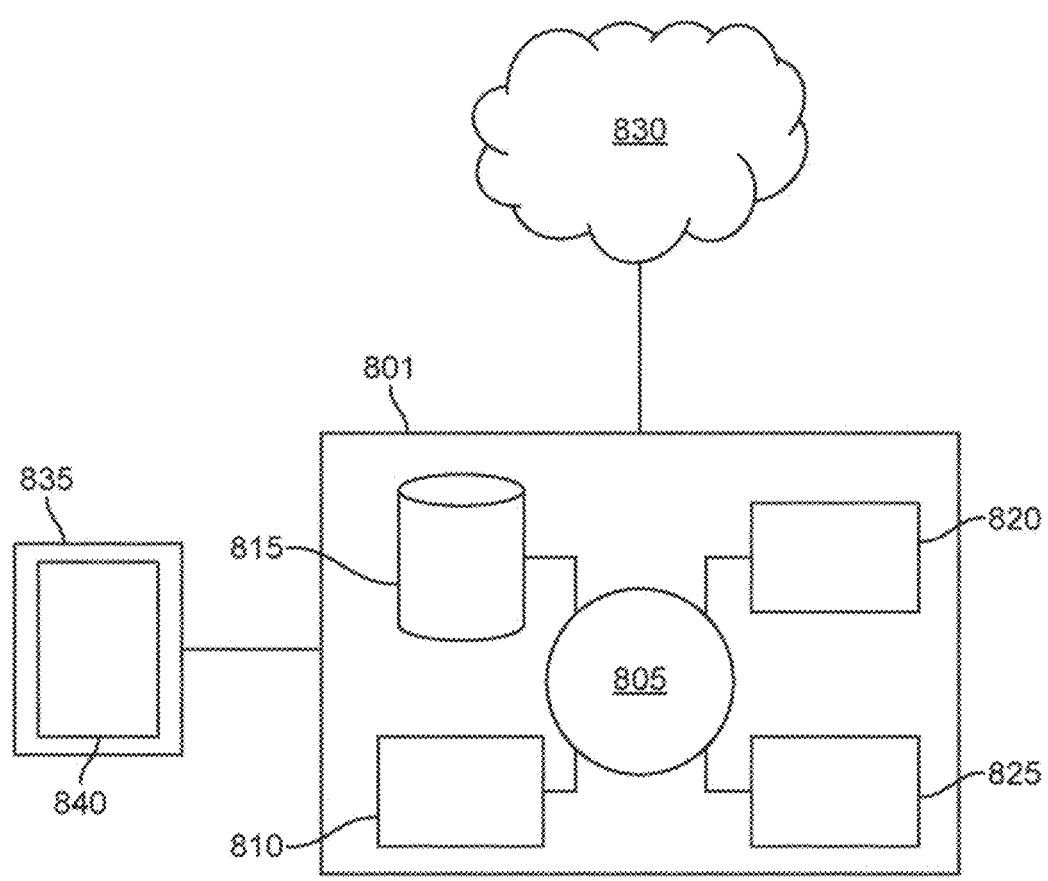
FIG. 8 shows a computer system suitable for incorporation with the methods and devices described herein.

The present disclosure provides computer control devices that are programmed to implement methods of the disclosure. FIG. 8 shows a computer device 801 suitable for incorporation with the methods and devices described herein. The computer device 801 can process various aspects of information of the present disclosure, such as, for example, questions and answers, responses, statistical analyses. The computer device 801 can be an electronic device of a user or a computer device that is remotely located with respect to the electronic device. The electronic device can be a mobile electronic device.

The computer device 801 includes a central processing unit (CPU, also "processor" and "computer processor" herein) 805, which can be a single core or multi core processor, or a plurality of processors for parallel processing. The computer device 801 also includes memory or memory location 810 (e.g., random-access memory, read-only memory, flash memory), electronic storage unit 815 (e.g., hard disk), communication interface 820 (e.g., network adapter) for communicating with one or more other devices, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer device 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer device 801, can implement a peer-to-peer network, which may enable devices coupled to the computer device 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the device 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer device 801 in some cases can include one or more additional data storage units that are external to the computer device 801, such as located on a remote server that is in communication with the computer device 801 through an intranet or the Internet.

The computer device 801 can communicate with one or more remote computer devices through the network 830. For instance, the computer device 801 can communicate with a remote computer device of a user (e.g., a parent). Examples of remote computer devices and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer device 801 with the network 830.

Methods as described herein can be implemented by way of machine (e.g., computer processor) executable code stored on an electronic storage location of the computer device 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the platforms, systems, devices, methods, and media provided herein, such as the computer device 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer device. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer device 801 can include or be in communication with an electronic display 835 that comprises a user interface (UI) 840 for providing, for example, questions and answers, analysis results, recommendations. Examples of UI's include, without limitation, a graphical user interface (GUI) and web-based user interface.

Methods and devices of the present disclosure can be implemented by way of one or more algorithms and with instructions provided with one or more processors as disclosed herein. An algorithm can be implemented by way of software upon execution by the central processing unit 805. The algorithm can be, for example, random forest, graphical models, support vector machine or other.

Although the above steps show a method of a device in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Experimental Data

A data processing module as described herein was built on Python 2.7, Anaconda Distribution. The training data used to construct and train the assessment model included data generated by the Autism Genetic Resource Exchange (AGRE), which performed in-home assessments to collect ADI-R and ADOS data from parents and children in their homes. ADI-R comprises a parent interview presenting a total of 93 questions, and yields a diagnosis of autism or no autism. ADOS comprises a semi-structured interview of a child that yields a diagnosis of autism, ASD, or no diagnosis, wherein a child is administered one of four possible modules based on language level, each module comprising about 30 questions. The data included clinical diagnoses of the children derived from the assessments; if a single child had discrepant ADI-R versus ADOS diagnoses, a licensed clinical psychologist assigned a consensus diagnosis for the dataset for the child in question. The training data included a total of 3,449 data points, with 3,315 cases (autism or ASD) and 134 controls (non-spectrum). The features evaluated in the training data targeted 3 key domains: language, social communication, and repetitive behaviors.

A boosted Random Forest classifier was used to build the assessment model as described herein. Prior to training the assessment model on the training data, the training data was pre-processed to standardize the data, and re-encode categorical features in a one-hot representation as described herein. Since the training data was skewed towards individuals with autism or ASD, sample weighting was applied to attribute up to 50 times higher significance to data from non-spectrum individuals compared to data from autistic/ASD individuals. The assessment model was trained iteratively with boosting, updating the weighting of data points after each iteration to increase the significance attributed to data points that were misclassified, and retraining with the updated significances.

Figure 9:
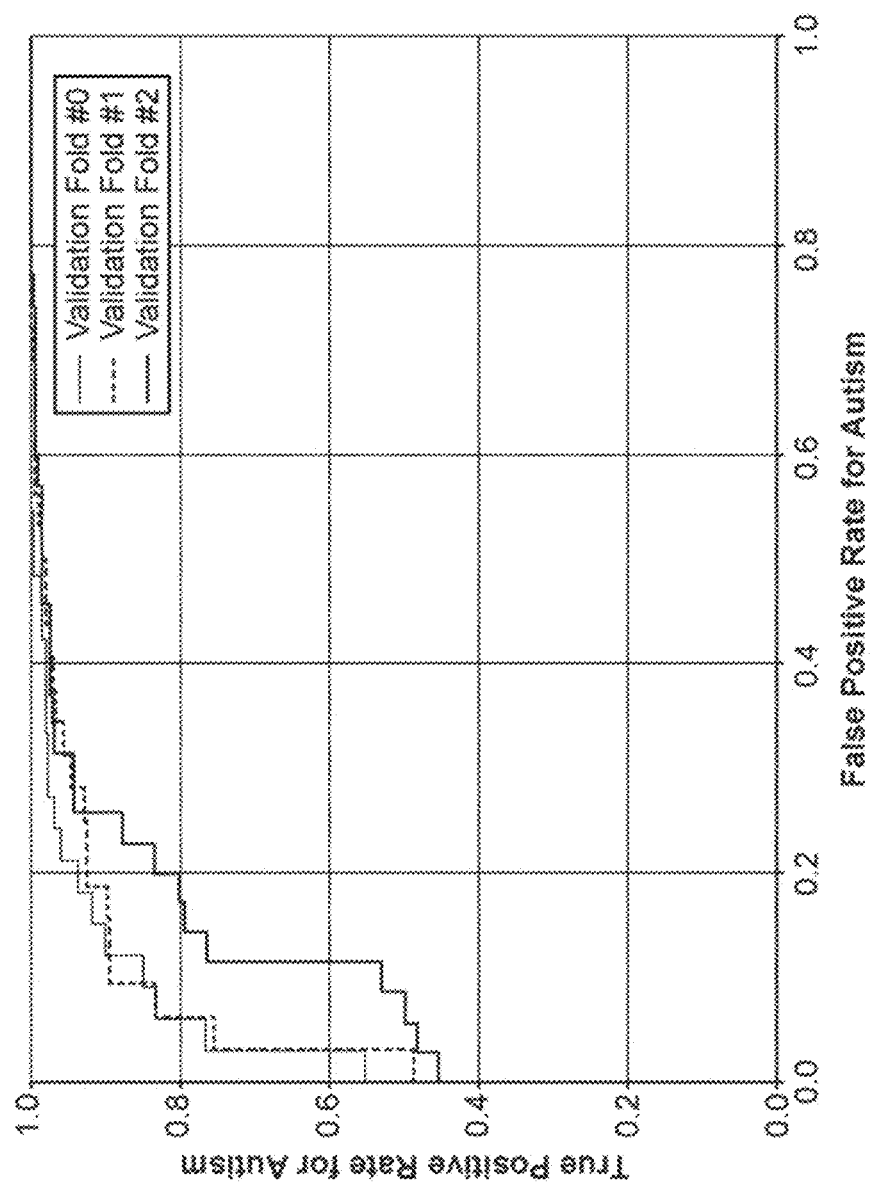
FIG. 9 shows receiver operating characteristic (ROC) curves mapping sensitivity versus fall-out for an assessment model as described herein.

The trained model was validated using Stratified k-fold cross validation with k=5. The cross-validation yielded an accuracy of about 93-96%, wherein the accuracy is defined as the percentage of subjects correctly classified using the model in a binary classification task (autism/non-spectrum). Since the training data contained a sample bias, a confusion matrix was calculated to determine how often the model confused one class (autism or non-spectrum) with another. The percentage of correctly classified autism individuals was about 95%, while the percentage of correctly classified non-spectrum individuals was about 76%. It should be noted, however, that the model may be adjusted to more closely fit one class versus another, in which case the percentage of correct classifications for each class can change. FIG. 9 shows receiver operating characteristic (ROC) curves mapping sensitivity versus fall-out for an assessment model as described herein. The true positive rate (sensitivity) for the diagnosis of autism is mapped on the y-axis, as a function of the false positive rate (fall-out) for diagnosis mapped on the x-axis. Each of the three curves, labeled "Fold #0", "Fold #1", and "Fold #2", corresponds to a different "fold" of the cross-validation procedure, wherein for each fold, a portion of the training data was fitted to the assessment model while varying the prediction confidence threshold necessary to classify a dataset as "autistic". As desired or appropriate, the model may be adjusted to increase the sensitivity in exchange for some increase in fall-out, or to decrease the sensitivity in return for a decrease in fall-out, as according to the ROC curves of the model.

Figure 10:
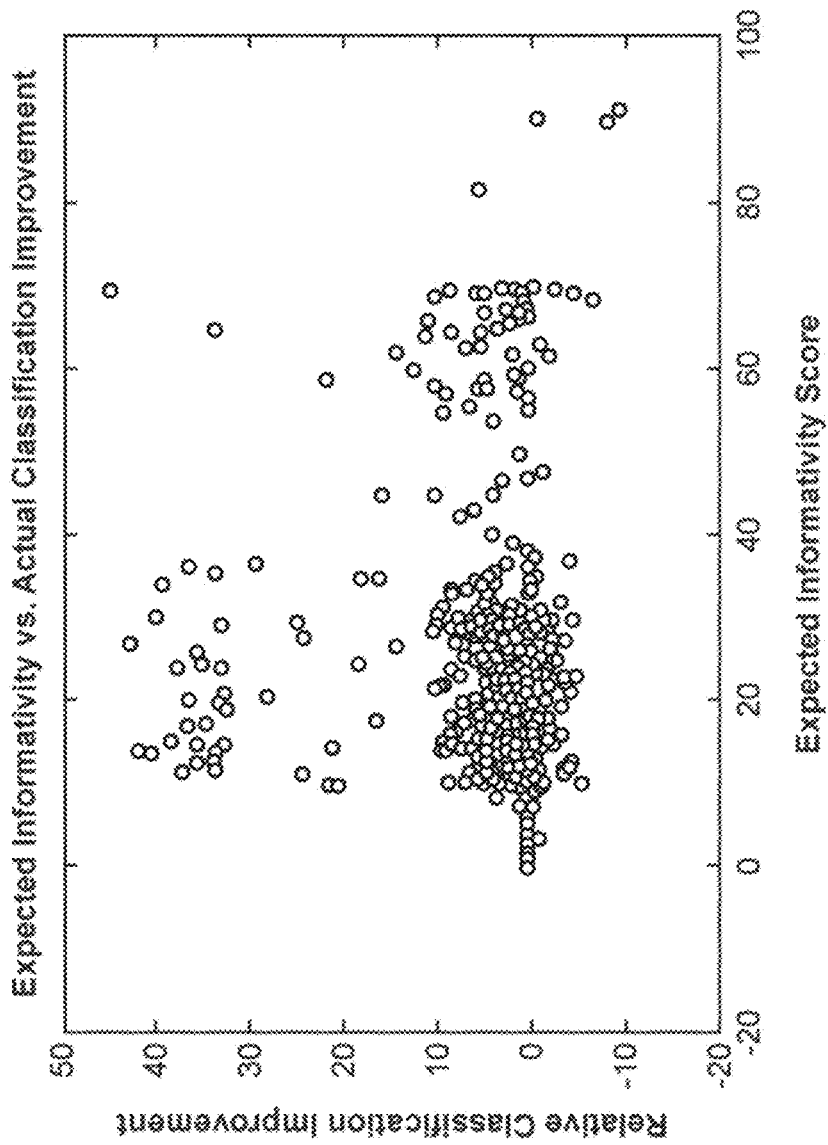
FIG. 10 is a scatter plot illustrating a performance metric for a feature recommendation module as described herein.

The feature recommendation module was configured as described herein, wherein the expected feature importance of each question was computed, and candidate questions ranked in order of computed importance with calls to a server with an application program interface (API). The feature recommendation module's ability to recommend informative questions was evaluated by determining the correlation between a question's recommendation score with the increase in prediction accuracy gained from answering the recommended question. The following steps were performed to compute the correlation metric: (1) the data was split up into folds for cross-validation; (2) already answered questions were randomly removed from the validation set; (3) expected feature importance (question recommendation/score) was generated for each question; (4) one of the questions removed in step 2 was revealed, and the relative improvement in the subsequent prediction accuracy was measured; and (5) the correlation between the relative improvement and the expected feature importance was computed. The calculated Pearson correlation coefficient ranged between 0.2 and 0.3, indicating a moderate degree of correlation between the expected feature importance score and the relative improvement. FIG. 10 is a scatter plot showing the correlation between the expected feature importance ("Expected Informativitiy Score") and the relative improvement ("Relative Classification Improvement") for each question. The plot shows a moderate linear relationship between the two variables, demonstrating the feature recommendation module is indeed able to recommend questions that would increase the prediction accuracy.

The length of time to produce an output using the developed prediction module and the feature recommendation model was measured. The prediction module took about 46 ms to make a prediction of an individual's risk of autism. The feature recommendation module took about 41 ms to generation question recommendations for an individual. Although these measurements were made with calls to a server through an API, the computations can be performed locally, for example.

While the assessment model of the data processing module described with respect to FIGS. 9-10 was constructed and trained to classify subjects as having autism or no autism, a similar approach may be used to build an assessment model that can classify a subject as having one or more of a plurality of developmental disorders, as described herein.

In another aspect, the methods and devices disclosed herein can identify a subject as belonging to one of three categories: having a developmental condition, being developmentally normal or typical, or inconclusive or requiring additional evaluation to determine whether the subject has the developmental condition. The developmental condition can be a developmental disorder or a developmental advancement. The addition of the third category, namely the inconclusive determination, results in improved performance and better accuracy of the categorical evaluations corresponding to the presence or absence of a developmental condition.

Figure 11:
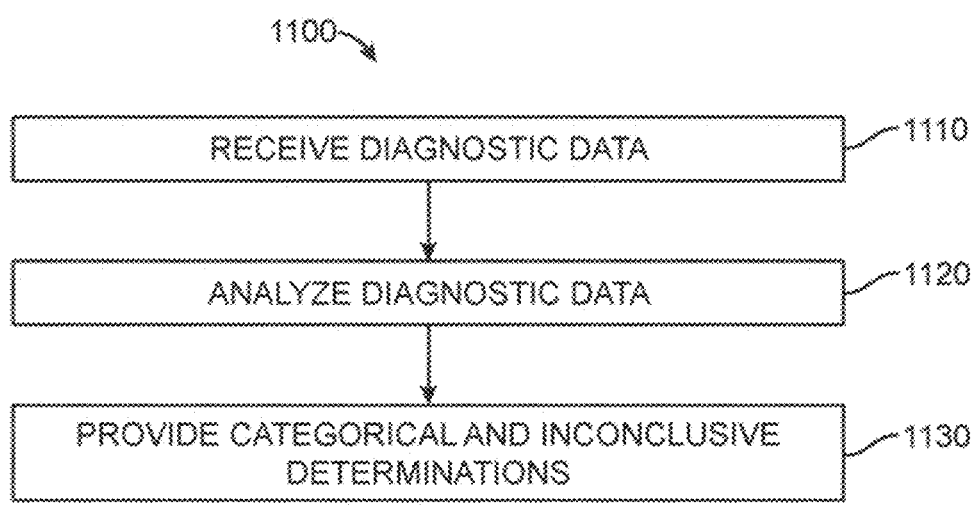
FIG. 11 is an operational flow of an evaluation module as described herein.

FIG. 11 is an operational flow of an evaluation module identifying a subject as belonging to one of three categories. As shown in FIG. 11, a method 1100 is provided for evaluating at least one behavioral developmental condition of a subject. The evaluation module receives diagnostic data of the subject related to the behavioral developmental at 1110, evaluates the diagnostic data at 1120 using a selected subset of a plurality of machine learning assessment models and provides categorical determinations for the subject at 1130. The categorical determination can be inconclusive, or can indicate the presence or absence of the behavioral developmental condition.

Figure 12:
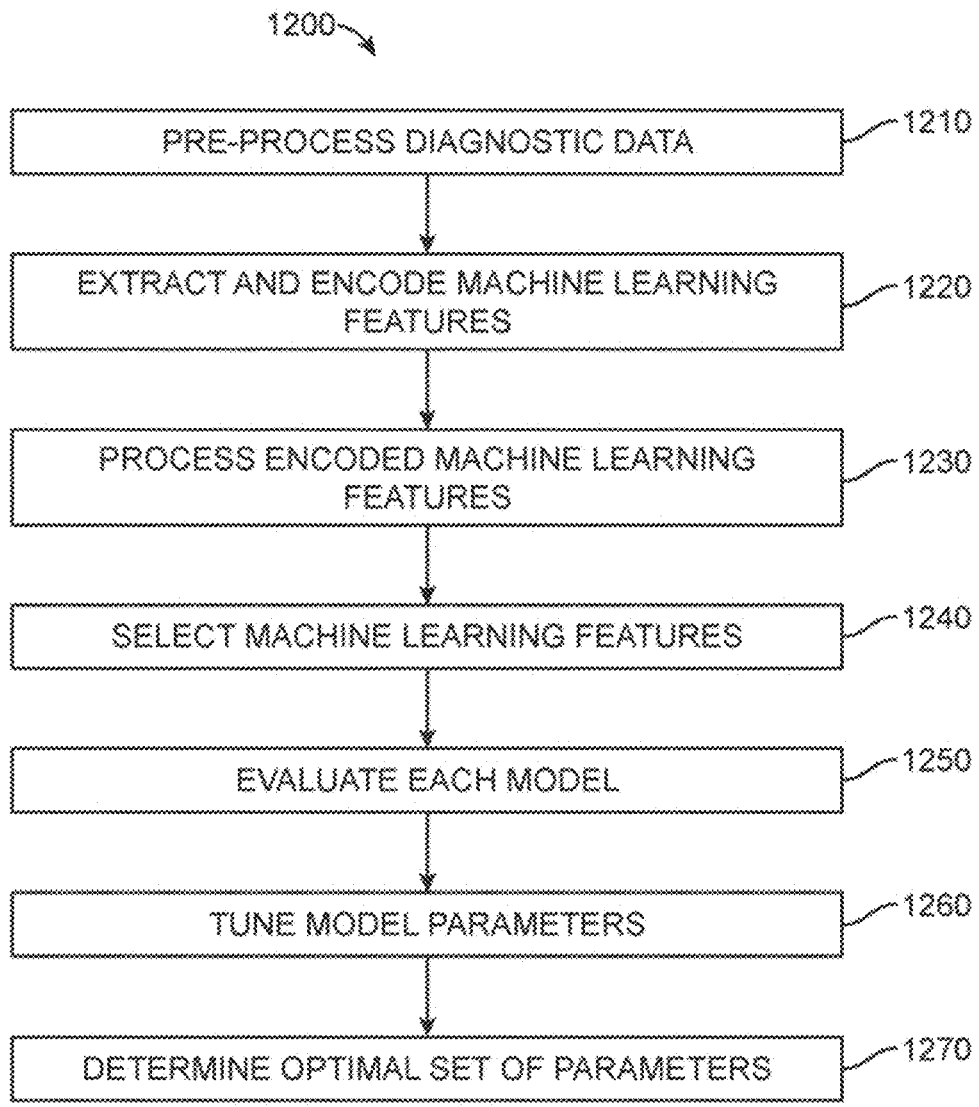
FIG. 12 is an operational flow of a model tuning module as described herein.

FIG. 12 is an operational flow of a model training module as described herein. As shown in FIG. 12, a method 1200 is provided for using machine learning to train an assessment model and tune its configuration parameters optimally. Multiple machine learning predictive models can be trained and tuned using the method 1200, each using datasets prepared offline and comprising a representative sample of a standardized clinical instrument such as ADI-R, ADOS, or SRS. Models can also be trained using datasets comprising data other than clinical instruments, such as demographic data. The model training module pre-processes diagnostic data from a plurality of subjects using machine learning techniques at 1210. Datasets can be pre-processed using well-established machine learning techniques such as data cleaning, filtering, aggregation, imputation, normalization, and other machine learning techniques as known in the art.

The model training module extracts and encodes machine learning features from the pre-processed diagnostic data at 1220. Columns comprising the datasets can be mapped into machine learning features using feature encoding techniques such as, for example, one-hot encoding, severity encoding, presence-of-behavior encoding or any other feature encoding technique as known in the art. Some of these techniques are novel in nature and not commonly used in machine learning applications, but they are advantageous in the present application because of the nature of the problem at hand, specifically because of the discrepancy between the setting where clinical data is collected and the intended setting where the model will be applied.

Presence of behavior encoding in particular is advantageous for the problem at hand especially, since the machine learning training data is comprised of clinical questionnaires filled by psycho-metricians having observed subjects for multiple hours. The answer codes they fill in can correspond to subtle levels of severity or differences in behavioral patterns that may only become apparent throughout the long period of observation. This data is then used to train models destined to be applied in a setting where only a few minutes of subject observation is available. Hence the subtleties in behavioral patterns are expected to be less often noticeable. Presence of behavioral encoding as described herein mitigates this problem by abstracting away the subtle differences between the answer choices and extracting data from the questionnaires only at the level of granularity that is expected to be reliably attained in the application setting.

The model training module processes the encoded machine learning features at 1230. In an embodiment, questionnaire answers can be encoded into machine learning features, after which, a sample weight can be computed and assigned to every sample of diagnostic data in a dataset, each sample corresponding to each subject having diagnostic data. Samples can be grouped according to subject-specific dimensions and sample weights can be computed and assigned to balance one group of samples against every other group of samples to mirror the expected distribution of subjects in an intended setting. For example, samples with positive classification labels might be balanced against those with negative classification labels. Alternatively or additionally, samples in each of multiple age group bins can be made to amount to an equal total weight. Additional sample balancing dimensions can be used such as gender, geographic region, sub-classification within the positive or negative class, or any other suitable dimension.

The process of sample-weight adjustment might be further refined to mirror the expected distribution of subjects in the intended application setting. This can allow the trained models to be adapted to various specific application settings. For example, a model can be trained for use specifically as a level two screening tool by adjusting the sample weights in the training dataset to reflect the expected prevalence rates of diagnostic conditions in a level two diagnostic clinic. Another variant of the same screener can be trained for use as a general public screening tool, again by adjusting the weights of training samples to reflect and expected population of mostly neuro-typical subjects and a minority of positive samples with prevalence rates to match those in the general population. to mirror an expected distribution of subjects in an intended application setting.

The model training module selects a subset of the processed machine learning features at 1240. In an embodiment, with the training samples weighted accordingly, and all potential machine learning features encoded appropriately, feature selection can take place using a machine learning process generally known as bootstrapping, where multiple iterations of model training can be run, each using a random subsample of the training data available. After each run, a tally can be updated with the features the training process deemed necessary to include in the model. This list can be expected to vary from run to run, since the random data subsets used in training might contain apparent patterns that are incidental to the choice of data samples and not reflective of real life patterns for the problem at hand. Repeating this process multiple times can allow for the incidental patterns to cancel out, revealing the features that are reflective of patterns that can be expected to generalize well outside the training dataset and into the real world. The top features of the bootstrapping runs can then be selected and used exclusively for training the final model, which is trained using the entire training dataset, and saved for later application.

Several models can be trained instead of one model, in order to specialize the models over a demographic dimension in situations where the dimension is expected to affect the choice of useful features. For example, multiple questionnaire-based models can be built, each for a specific age group, since the best questions to ask of a subject are expected to be different for each age group. In this case, only the right model for each subject is loaded at application time.

The model training module evaluates each model at 1250. In particular, each model can be evaluated for performance, for example, as determined by sensitivity and specificity for a pre-determined inclusion rate. In an embodiment, using a held-out dataset that was not used during the model training phase, the models can be evaluated for performance, in terms of inclusion rate, sensitivity, and specificity.

The model training module tunes each model at 1260. More specifically, to assess the performance of the models in different tuning settings, the tuning parameters of each model can be changed in iterative increments and the same metrics can be computed over the same held-out set in every iteration. The optimal settings can then be locked in and the corresponding models saved. Tuning parameters can include, for example, the number of trees in a boosted decision tree model, the maximum depth of every tree, the learning rate, the threshold of positive determination score, the range of output deemed inconclusive, and any other tuning parameter as known in the art.

In a preferable embodiment, the parameter tuning process of 1260 can comprise a brute-force grid search, an optimized gradient descent or simulated annealing, or any other space exploration algorithm as known in the art. The models being tuned can undergo separate, independent tuning runs, or alternatively the models can be tuned in an ensemble fashion, with every parameter of every model explored in combination, in order to arrive at the optimal overall set of parameters at 1270 to maximize the benefit of using all the models in an ensemble.

Moreover, in yet another aspect, tuning the inconclusive range of each predictive model can be augmented with an external condition, determined by a business need rather than a performance metric. For example, it can be deemed necessary for a particular classifier to have an inclusion rate of no less than 70%. In other words, the classifier would be expected to provide an evaluation indicating either the presence or the absence of a developmental condition for at least 70% of the subjects being classified, yielding an inconclusive determination for less than 30% of the subjects. Accordingly, the corresponding tuning process for the inconclusive output range would have to be limited to only the ranges where this condition is met.

The models are tunable based on the context of the application. The predictive model can be configured to output a diagnosis having a particular degree of certainty that can be adjusted based on tuning of the inconclusive range.

In addition, tuning of the inconclusive range can be exposed outside the offline machine learning phase. More specifically, tuning of the inconclusive range can be a configurable parameter accessible to agents operating the models after deployment. In this way, it is possible for an operator to dial the overall device up or down along the tradeoff between more inclusion and more accuracy. To support this case, multiple optimal inconclusive ranges might be explored and stored during the model training phase, each with its corresponding inclusion rate. The agent can then affect that change by selecting an optimal point from a menu of previously determined optimal settings.

Figure 13:
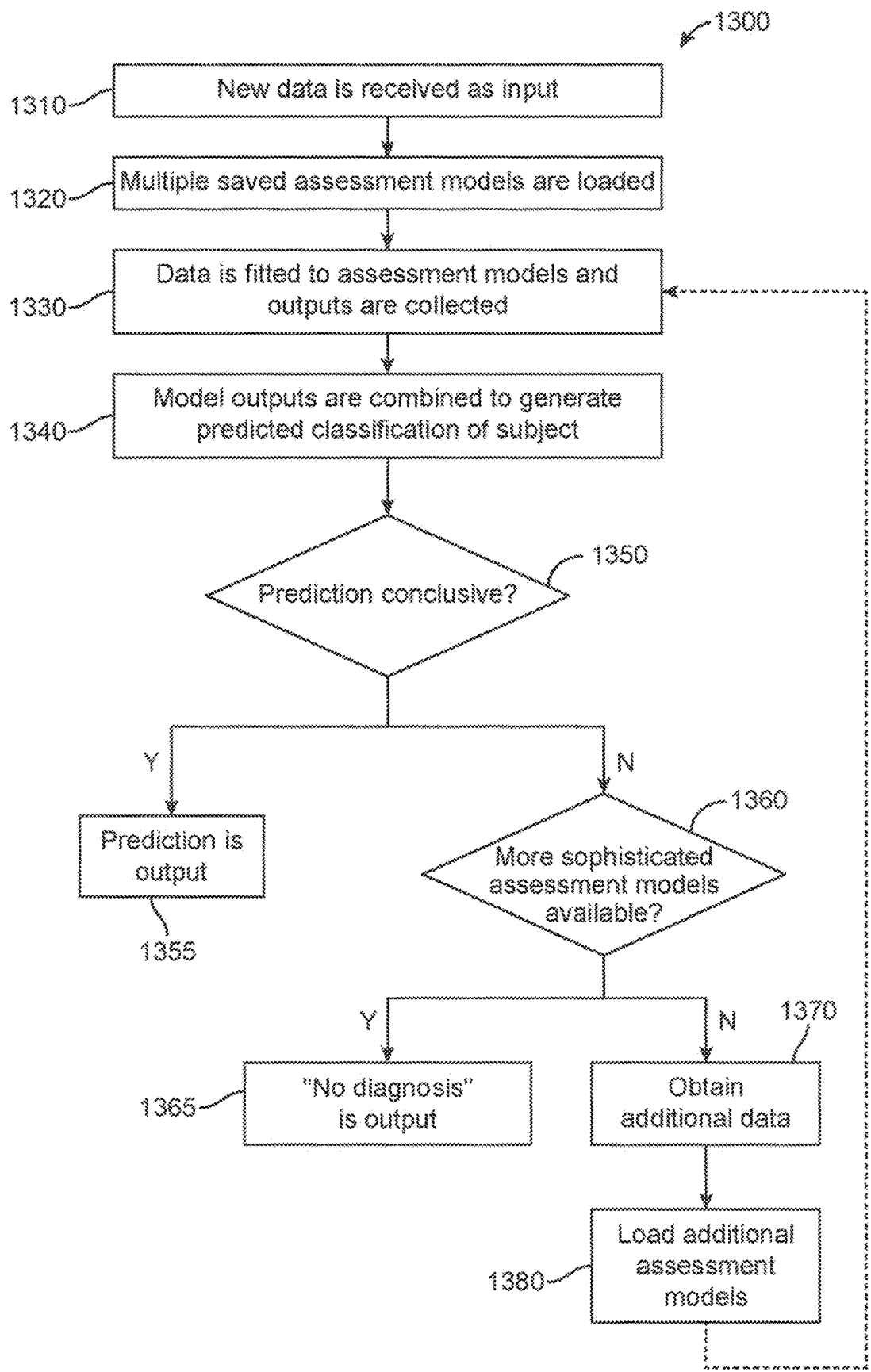
FIG. 13 is another operational flow of an evaluation module as described herein.

FIG. 13 is another operational flow of an evaluation module as described herein. As shown in FIG. 13, a method 1300 is provided for outputting a conclusive prediction at 1355 indicating the presence or absence of a developmental condition, or an inconclusive determination of "No diagnosis" at 1365.

The evaluation module as depicted in FIG. 13 receives new data such as diagnostic data from or associated with a subject to be evaluated as having or not having a developmental condition at 1310. Multiple saved assessment models that have been trained, tuned, and optimized as depicted in FIG. 12 and as described herein can be loaded at 1320. Diagnostic data can be fit to these initial assessment models and outputs can be collected at 1330. The evaluation module can combine the initial assessment model outputs at 1340 to generate a predicted initial classification of the subject. If the evaluation module determines that the initial prediction is conclusive at 1350, it can output a conclusive determination indicating either the presence or absence of the developmental condition in the subject. If the evaluation module determines that the initial prediction is inconclusive at 1350, it can then proceed to determine whether additional or more sophisticated assessment models are available and applicable at 1360. If no additional assessment models are available or applicable, the evaluation module outputs an inconclusive determination of "No diagnosis." If however, the evaluation module determines that additional or more sophisticated assessment models are available and applicable, it can proceed to obtain additional diagnostic data from or associated with the subject at 1370. Next, the evaluation module can load the additional or more sophisticated assessment models at 1380 and can repeat the process of fitting data to the models, only this time, the additional data obtained at 1370 is fitted to the additional assessment models loaded at 1380 to produce new model outputs, which are then evaluated at 1350 for a conclusive prediction. This process as depicted by the loop comprising steps 1350, 1355, 1360, 1365, 1370, 1380 and back to 1330 and 1340 can be repeated until either a conclusive prediction is output at 1355, or if no more applicable classification models are available to use, an inconclusive determination of "No diagnosis" is output at 1365.

In particular, when data from a new subject is received as input at 1310 in FIG. 13, each available model for preliminary determination is loaded at 1320 and run, outputting a numerical score at 1330. The scores can then be combined using a combinatorial model.

Figure 14:
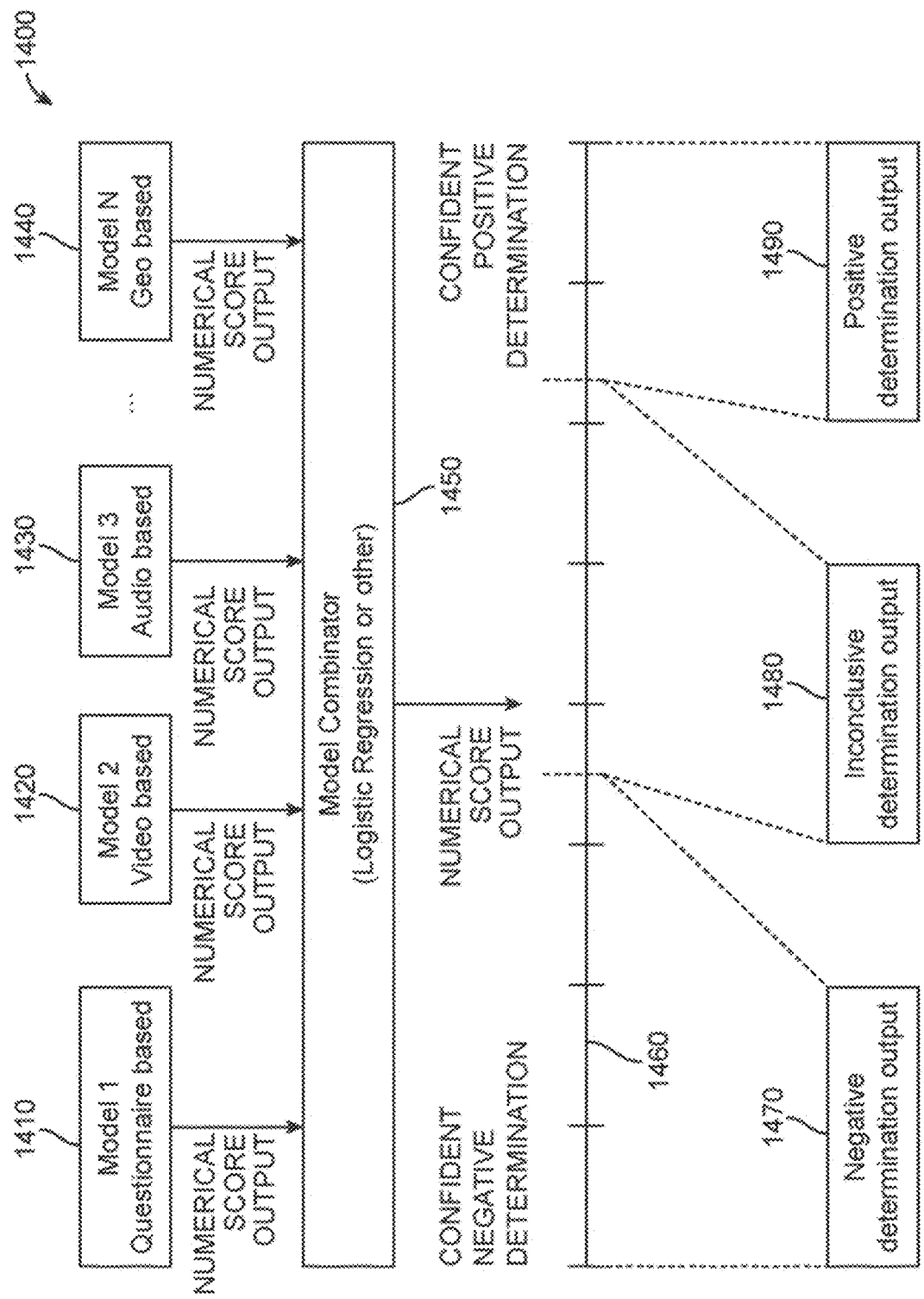
FIG. 14 is an operational flow of the model output combining step depicted in FIG. 13.

FIG. 14 is a non-limiting operational flow of the model output combining step depicted in FIG. 13. As shown in FIG. 14, a combiner module 1400 can collect the outputs from multiple assessment models 1410, 1420, 1430, and 1440, which are received by a model combinatory or combinatorial model 1450. The combinatorial model can employ simple rule-based logic to combine the outputs, which can be numerical scores. Alternatively, the combinatorial model can use more sophisticated combinatorial techniques such as logistic regression, probabilistic modeling, discriminative modeling, or any other combinatorial technique as known in the art. The combinatorial model can also rely on context to determine the best way to combine the model outputs. For example, it can be configured to trust the questionnaire-based model output only in a certain range, or to defer to the video-based model otherwise. In another case, it can use the questionnaire-based model output more significantly for younger subjects than older ones. In another case, it can exclude the output of the video-based model for female subjects, but include the video-based model for male subjects.

The combinatorial model output score can then be subjected to thresholds determined during the model training phase as described herein. In particular, as shown in FIG. 14, these thresholds are indicated by the dashed regions that partition the range of numerical scores 1460 into three segments corresponding to a negative determination output 1470, an inconclusive determination output 1480, and a positive determination output 1490. This effectively maps the combined numerical score to a categorical determination, or to an inconclusive determination if the output is within the predetermined inconclusive range.

In the case of an inconclusive output, the evaluation module can determine that additional data should be obtained from the subject in order to load and run additional models beyond the preliminary or initial set of models. The additional models might be well suited to discern a conclusive output in cases where the preliminary models might not. This outcome can be realized by training additional models that are more sophisticated in nature, more demanding of detailed input data, or more focused on the harder-to-classify cases to the exclusion of the straightforward ones.

Figure 15:
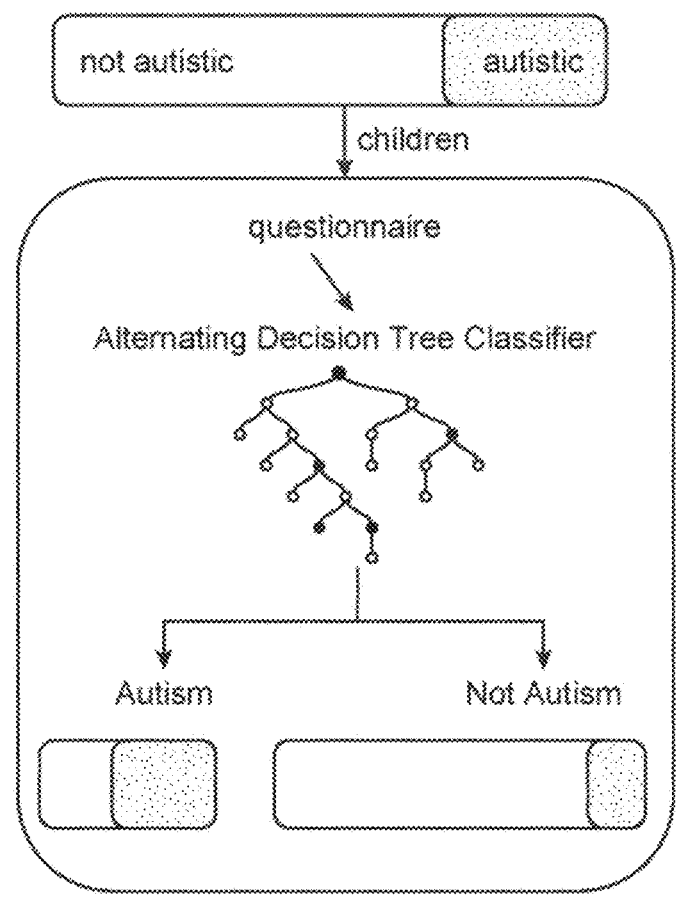
FIG. 15 shows a questionnaire screening algorithm configured to provide only categorical determinations as described herein.

FIG. 15 shows an example of a questionnaire screening algorithm configured to provide only categorical determinations of a developmental condition as described herein. In particular, the questionnaire screening algorithm depicted in FIG. 15 shows an alternating decision tree classifier that outputs a determination indicating only the presence or the absence of autism. The different shading depicts the total population of children who are autistic and not autistic and who are evaluated via the questionnaire. Also depicted are the results of the classifier, showing the correctly and incorrectly diagnosed children populations for each of the two categorical determinations.

Figure 16:
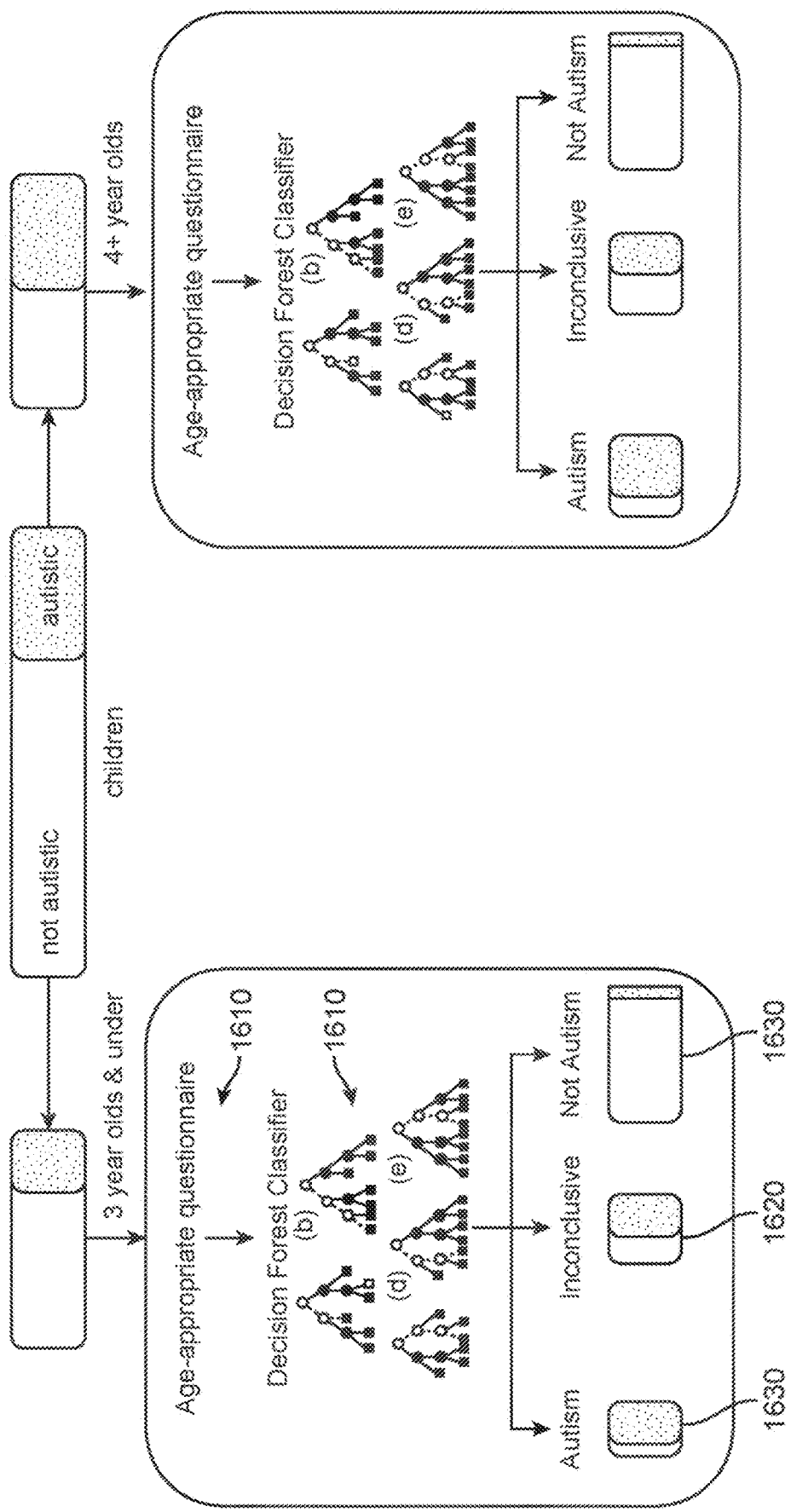
FIG. 16 shows a questionnaire screening algorithm configured to provide categorical and inconclusive determinations as described herein.

In contrast, FIG. 16 shows an example of a Triton questionnaire screening algorithm configured to provide both categorical and inconclusive determinations as described herein. In particular, the Triton algorithm depicted in FIG. 16 implements both age-appropriate questionnaires and age-specific models to yield specialized classifiers for each of two subgroups (i.e. "3 years old & under" and "4+ year olds") within a relevant age group (i.e. "children"). It is clear from this example that the categorical determinations indicating the presence and absence of Autism in the two subgroups in FIG. 16 each have a higher accuracy when compared with the categorical determinations in FIG. 15, as indicated by the different shaded areas showing the correctly and incorrectly diagnosed children populations for each of the two categorical determinations. By providing a separate category for inconclusive determinations, the Triton algorithm of FIG. 16 is better able to isolate hard-to-screen cases that result in inaccurate categorical determinations as seen in FIG. 15.

Figure 17:
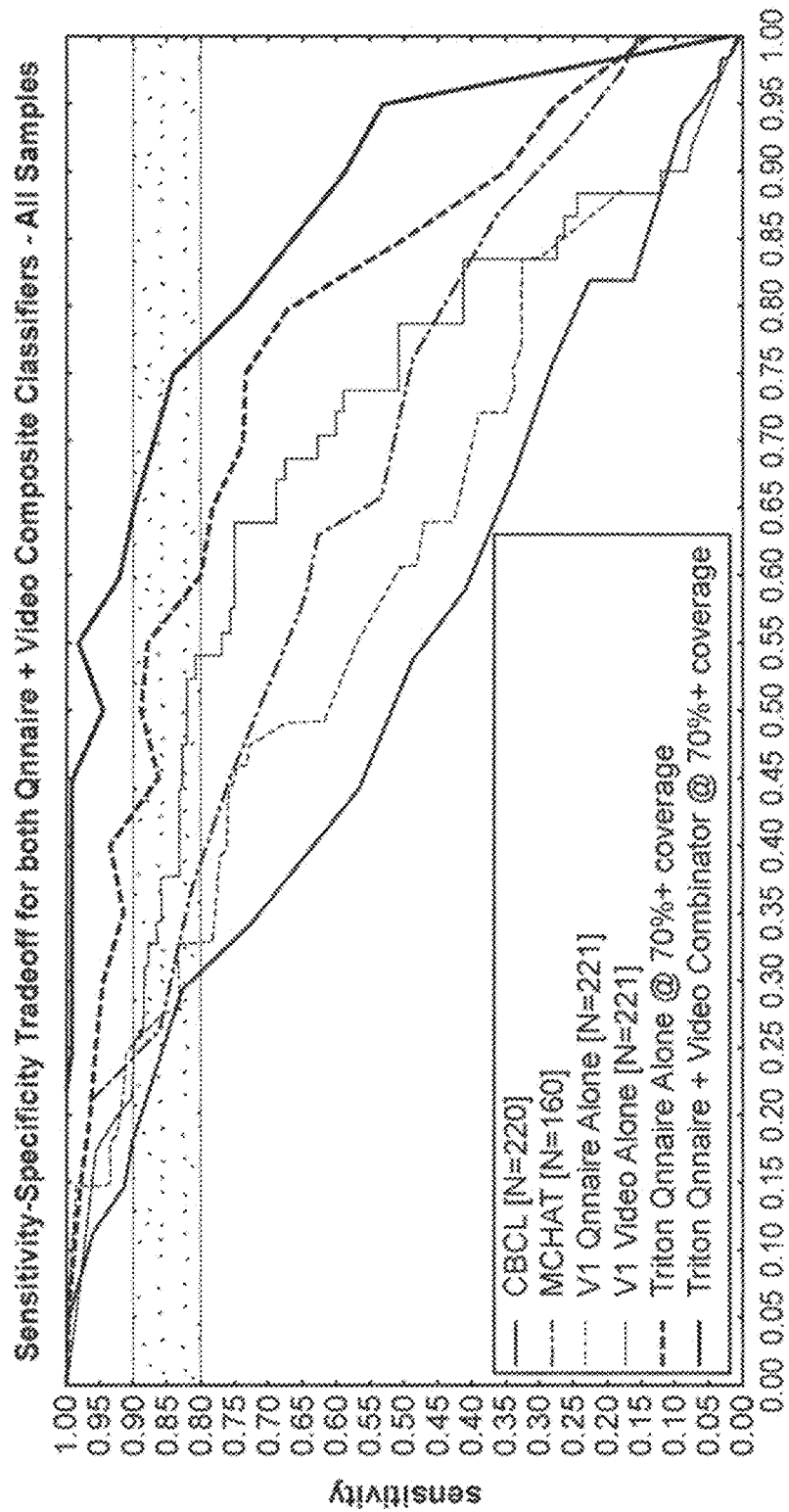
FIG. 17 shows a comparison of the performance for various algorithms for all samples as described herein.

A comparison of the performance for various algorithms highlights the advantages of the Triton algorithm, and in particular, the Triton algorithm having a context-dependent combination of questionnaire and video inputs. FIG. 17 shows a comparison of the performance for various algorithms in terms of a sensitivity-specificity tradeoff for all samples in a clinical sample as described herein. As shown in FIG. 17, the best performance in terms of both sensitivity and specificity is obtained by the Triton algorithm configured for 70% coverage when combined with the video combinator (i.e. context-dependent combination of questionnaire and video inputs).

Figure 18:
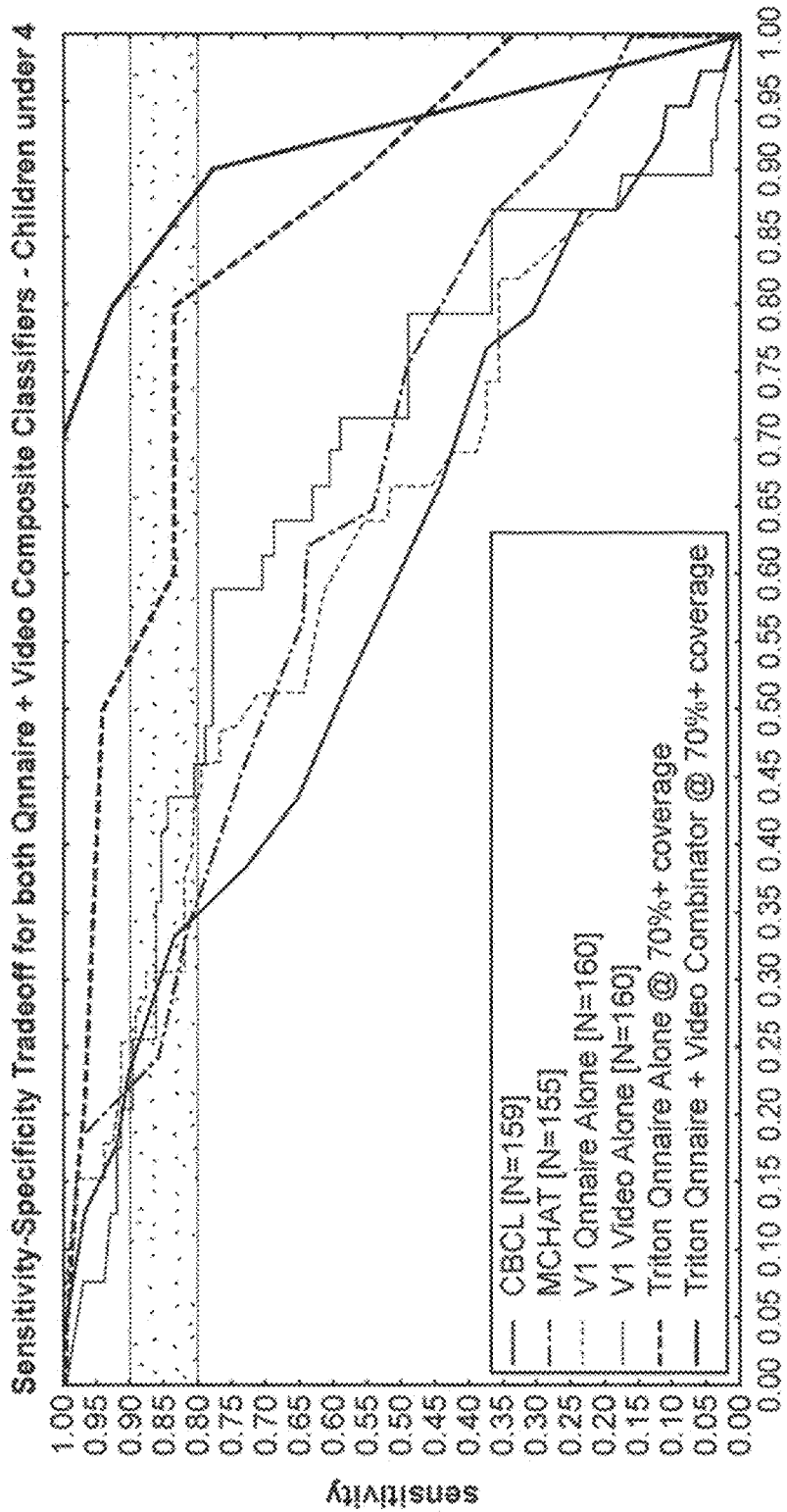
FIG. 18 shows a comparison of the performance for various algorithms for samples taken from Children Under 4 as described herein.

FIG. 18 shows a comparison of the performance for various algorithms in terms of a sensitivity-specificity tradeoff for samples taken from children under 4 as described herein. The Triton algorithm configured for 70% coverage when combined with the video combinator (i.e. context-dependent combination of questionnaire and video inputs) has the best performance.

Figure 19:
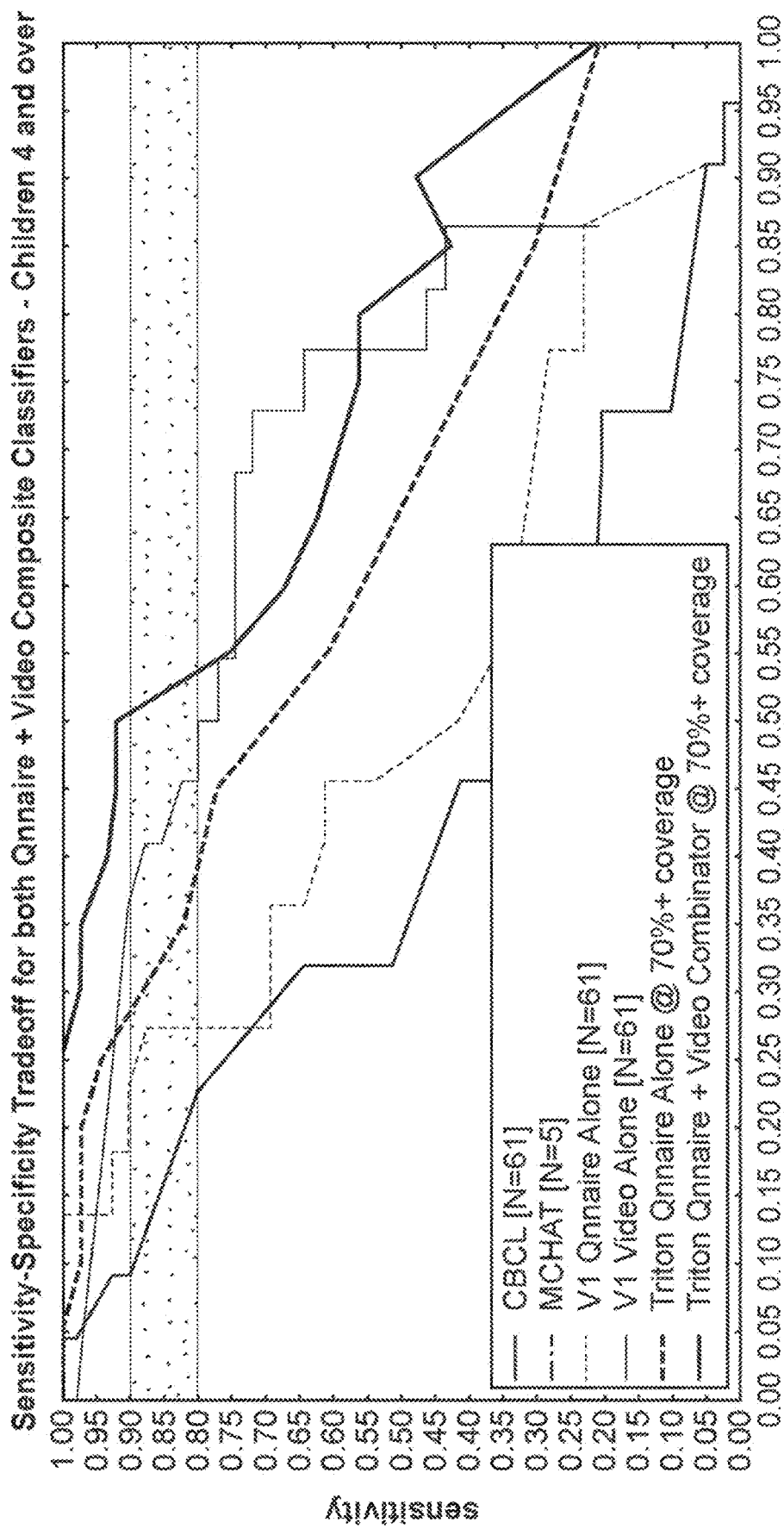
FIG. 19 shows a comparison of the performance for various algorithms for samples taken from Children 4 and Over described herein.

FIG. 19 shows a comparison of the performance for various algorithms in terms of a sensitivity-specificity tradeoff for samples taken from children 4 and over described herein. For the most part, the Triton algorithm configured for 70% coverage when combined with the video combinator appears to have the best performance.

Figure 20:
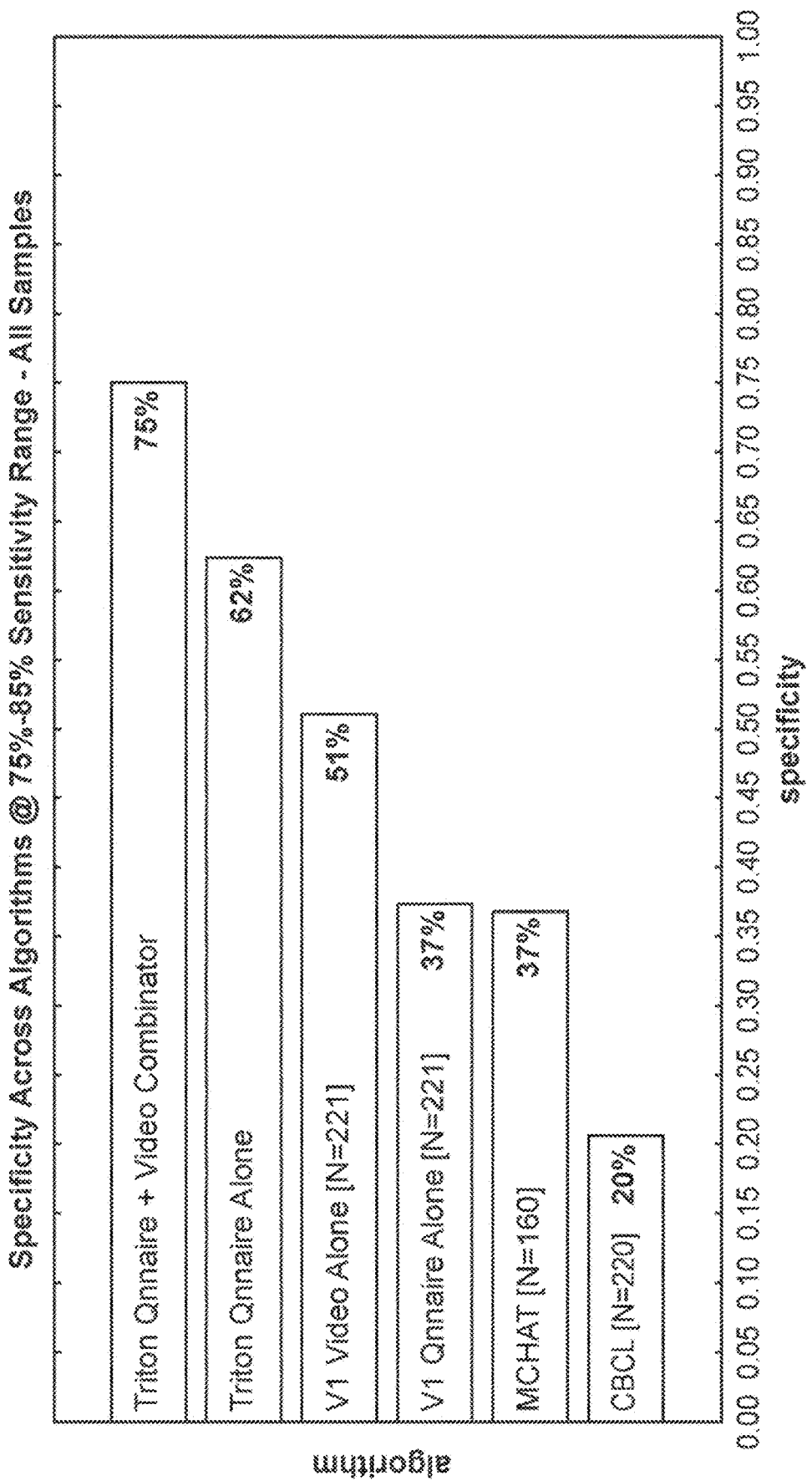
FIG. 20 shows the specificity across algorithms at 75%-85% sensitivity range for all samples as described herein.
Figure 21:
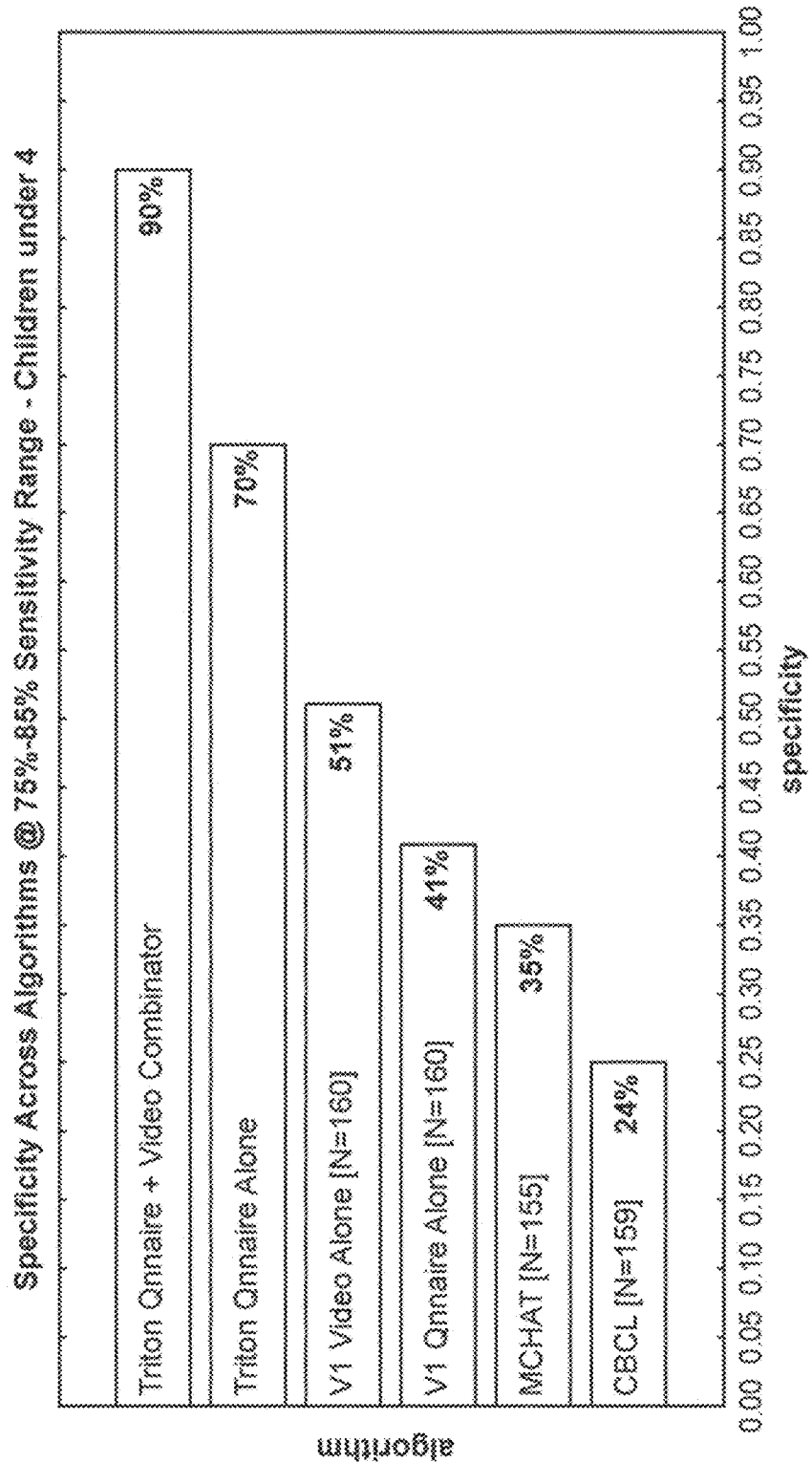
FIG. 21 shows the specificity across algorithms at 75%-85% sensitivity range for Children Under 4 as described herein.
Figure 22:
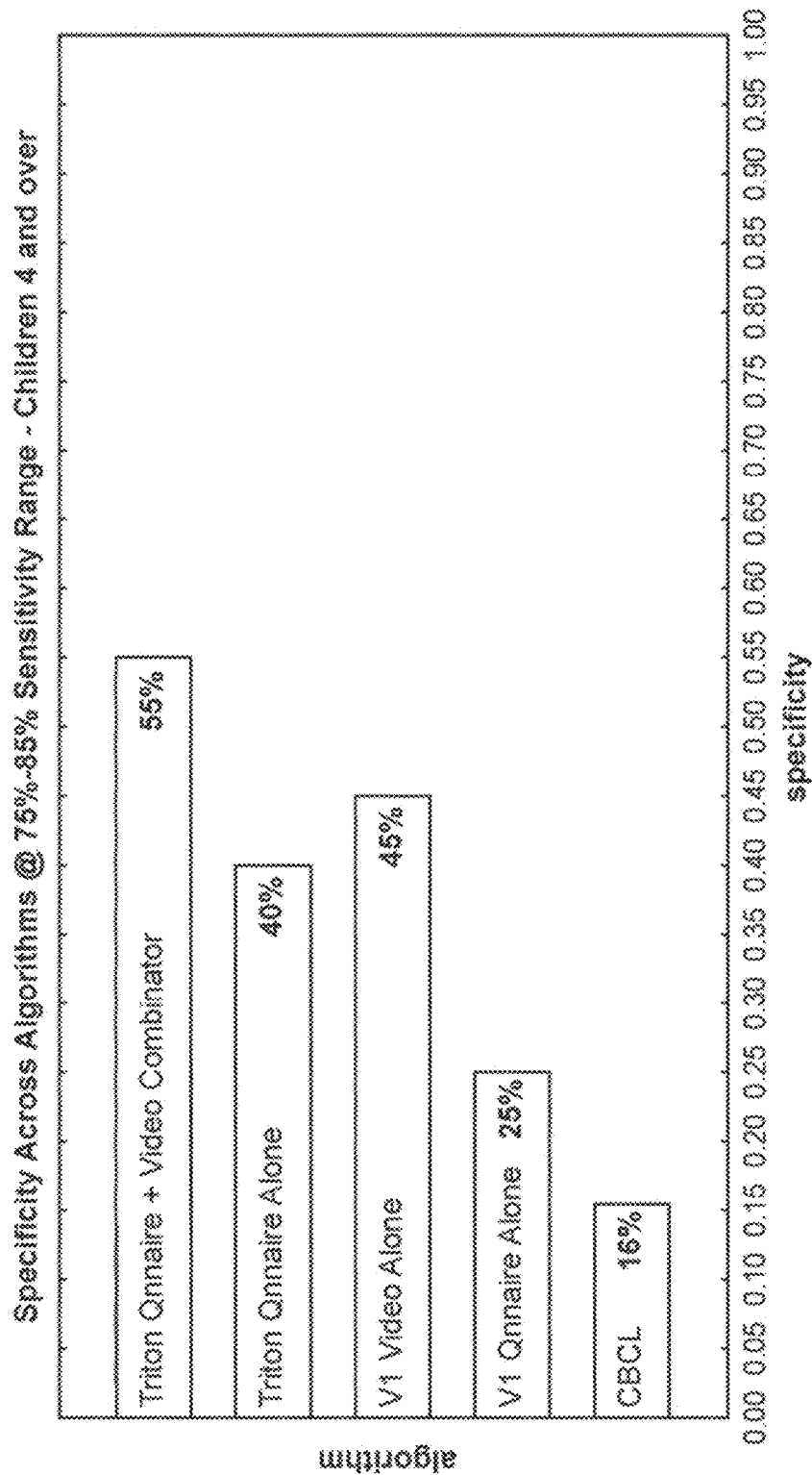
FIG. 22 shows the specificity across algorithms at 75%-85% sensitivity range for Children 4 and Over as described herein.

FIGS. 20-22, show the specificity for different algorithms at 75%-85% sensitivity range for all samples, for children under 4, and for children 4 and over. In all three cases, the Triton algorithm configured for 70% coverage when combined with the video combinator has the best performance, having 75% specificity for all samples, 90% specificity for children under 4, and 55% specificity for children 4 and over. Note that the Triton algorithm has the further advantage of flexibility. For example, tunable models are provided as described herein, wherein the inconclusive ratio or inclusion rate may be controlled or adjusted to control the tradeoff between coverage and reliability. In addition, the models described herein may be tuned to an application setting with respect to expected prevalence rates or based on expected population distributions for a given application setting. Finally, support for adaptive retraining enables improved performance over time given the feedback training loop of the method and device described herein.

A person of ordinary skill in the art can generate and obtain additional datasets and improve the sensitivity and specificity and confidence interval of the methods and devices disclosed herein to obtain improved results without undue experimentation. Although these measurements were performed with example datasets, the methods and devices can be configured with additional datasets as described herein and the subject identified as at risk with a confidence interval of 80% in a clinical environment without undue experimentation. The sensitivity and specificity of 80% or more in a clinical environment can be similarly obtained with the teachings provided herein by a person of ordinary skill in the art without undue experimentation, for example with additional datasets. In some instances, an additional dataset is obtained based on clinician questionnaires and used to generate assessment models that can be used alone or in combination with other models. For example, a parent or caregiver questionnaire, clinician questionnaire, results of video analysis, or any combination thereof can provide the inputs to one or more preliminary assessment models corresponding to each data source. These preliminary assessment models can generate outputs such as preliminary output scores that may be combined to generate a combined preliminary output score as described herein.

In certain instances, the assessment and/or diagnosis of the patient can be performed using an assessment module comprising a series of assessment models. The assessment module may interface or communicate with an input module configured to collect or obtain input data from a user. The series of assessment models can be used to inform the data collection process such that enough data is obtained to generate a conclusive determination. In some cases, the systems and methods disclosed herein collect an initial data set (e.g., including a parent or caregiver questionnaire) corresponding to the parent or caregiver assessment model using a first assessment module. The data set includes data corresponding to features of the assessment model, which can be evaluated in order to generate a determination, for example, a positive or negative determination (e.g., categorical determination) or an inconclusive determination regarding a behavioral disorder or condition such as autism. If the determination is inconclusive, then an additional data set may be obtained, for example, results of video analysis (e.g., an algorithmic or video analyst-based assessment of a captured video of the individual) using a second assessment module. Alternatively, in some cases, the results of video analysis are used along with the initial parent or caregiver data set to generate an assessment. This information may be incorporated into an assessment model configured to incorporate the additional data set from the video analysis to generate an updated determination. If the updated determination is still inconclusive, then another data set may be obtained, for example, a supplemental questionnaire by a healthcare provider such as a doctor or clinician (e.g., based on an in-person assessment) using a third assessment module. Such scenarios may occur in the case of especially difficult cases. Alternatively, the new data set may be optional and decided by the healthcare provider. The next data set may be obtained and then evaluated using an assessment model configured to incorporate this data in generating the next determination. Each of the series of assessment models may be configured to account for the existing data set and the new or additional data set in generating a determination. Alternatively, each of the series of assessment models may be only configured to account for the new or additional data set, and the outcome or score of the assessment models are simply combined as disclosed herein in order to generate the new or updated assessment outcome. The data sets can be obtained via one or more computing devices. For example, a smartphone of the parent or caregiver may be used to obtain input for the parent or caregiver questionnaire and to capture the video for analysis.

In some cases, the computing device is used to analyze the video, and alternatively, a remote computing device or a remote video analyst analyzes the video and answers an analyst-based questionnaire to provide the input data set. In some cases, a computing device of a doctor or clinician is used to provide the input data set. The analysis of the video and the assessment or diagnosis based on the input data using the one or more assessment models can be performed locally by one or more computing devices (e.g., parent's smartphone) or remotely such as via cloud computing (e.g., computation takes place on the cloud, and the outcome/result is transmitted to the user device for display). For example, a system for carrying out the methods disclosed herein can include a parent or caregiver mobile application and/or device, a video analyst portal and/or device, and a healthcare provider device and/or dashboard. A benefit of this approach of dynamically obtaining new data sets based on the status of the current assessment outcome or determination is that the evaluation or diagnostic process is performed more efficiently without requiring more data than is necessary to generate a conclusive determination.

Additional datasets may be obtained from large archival data repositories as described herein, such as the Autism Genetic Resource Exchange (AGRE), Boston Autism Consortium (AC), Simons Foundation, National Database for Autism Research, and the like. Alternatively or in combination, additional datasets may comprise mathematically simulated data, generated based on archival data using various simulation algorithms. Alternatively or in combination, additional datasets may be obtained via crowd-sourcing, wherein subjects self-administer the assessment procedure as described herein and contribute data from their assessment. In addition to data from the self-administered assessment, subjects may also provide a clinical diagnosis obtained from a qualified clinician, so as to provide a standard of comparison for the assessment procedure.

In another aspect, a digital personalized medicine device as described herein comprises digital devices with processors and associated software configured to: receive data to assess and diagnose a patient; capture interaction and feedback data that identify relative levels of efficacy, compliance and response resulting from the therapeutic interventions; and perform data analysis, including at least one or machine learning, artificial intelligence, and statistical models to assess user data and user profiles to further personalize, improve or assess efficacy of the therapeutic interventions.

The assessment and diagnosis of the patient in the digital personalized medicine device can categorize a subject into one of three categories: having one or more developmental conditions, being developmentally normal or typical, or inconclusive (i.e. requiring additional evaluation to determine whether the subject has any developmental conditions). In particular, a separate category can be provided for inconclusive determinations, which results in greater accuracy with respect to categorical determinations indicating the presence or absence of a developmental condition. A developmental condition can be a developmental disorder or a developmental advancement. Moreover, the methods and devices disclosed herein are not limited to developmental conditions, and may be applied to other cognitive functions, such as behavioral, neurological or mental health conditions.

In some instances, the device can be configured to use digital diagnostics and digital therapeutics. Digital diagnostics and digital therapeutics can comprise a device or methods comprising collecting digital information and processing and evaluating the provided data to improve the medical, psychological, or physiological state of an individual. The device and methods described herein can categorize a subject into one of three categories: having one or more developmental conditions, being developmentally normal or typical, or inconclusive (i.e. requiring additional evaluation to determine whether the subject has any developmental conditions). In particular, a separate category can be provided for inconclusive determinations, which results in greater accuracy with respect to categorical determinations indicating the presence or absence of a developmental condition. A developmental condition can be a developmental disorder or a developmental advancement. Moreover, the methods and devices disclosed herein are not limited to developmental conditions, and may be applied to other cognitive functions, such as behavioral, neurological or mental health conditions. In addition, a digital therapeutic device can apply software based learning to evaluate user data, monitor and improve the diagnoses and therapeutic interventions provided by the device.

Digital diagnostics in the device can comprise of data and meta-data collected from the patient, or a caregiver, or a party that is independent of the individual being assessed. In some instances the collected data can comprise monitoring behaviors, observations, judgements, or assessments may be made by a party other than the individual. In further instances, the assessment can comprise an adult performing an assessment or provide data for an assessment of a child or juvenile.

Data sources can comprise either active or passive sources, in digital format via one or more digital devices such as mobile phones, video capture, audio capture, activity monitors, or wearable digital monitors. Examples of active data collection comprise devices, devices or methods for tracking eye movements, recording body or appendage movement, monitoring sleep patterns, recording speech patterns. In some instances, the active sources can include audio feed data source such as speech patterns, lexical/syntactic patterns (for example, size of vocabulary, correct/incorrect use of pronouns, correct/incorrect inflection and conjugation, use of grammatical structures such as active/passive voice etc., and sentence flow), higher order linguistic patterns (for example, coherence, comprehension, conversational engagement, and curiosity). Active sources can also include touch-screen data source (for example, fine-motor function, dexterity, precision and frequency of pointing, precision and frequency of swipe movement, and focus/attention span). Video recording of subject's face during activity (for example, quality/quantity of eye fixations vs saccades, heat map of eye focus on the screen, focus/attention span, variability of facial expression, and quality of response to emotional stimuli) can also be considered an active source of data.

Passive data collection can comprise devices, devices, or methods for collecting data from the user using recording or measurements derived from mobile applications, toys with embed sensors or recording units. In some instances, the passive source can include sensors embedded in smart toys (for example, fine motor function, gross motor function, focus/attention span and problem solving skills) and wearable devices (for example, level of activity, quantity/quality of rest).

The data used in the diagnosis and treatment can come from a plurality of sources, and may comprise a combination of passive and active data collection gathered from one device such as a mobile device with which the user interacts, or other sources such as microbiome sampling and genetic sampling of the subject.

The methods and devices disclosed herein are well suited for the diagnosis and digital therapeutic treatment of cognitive and developmental disorders, mood and mental illness, and neurodegenerative diseases. Examples of cognitive and developmental disorders include speech and learning disorders and other disorders as described herein. Examples of mood and mental illness disorders, which can affect children and adults, include behavioral disorders, mood disorders, depression, attention deficit hyperactivity disorder ("ADHD"), obsessive compulsive disorder ("OCD"), schizophrenia, and substance-related disorders such as eating disorders and substance abuse. Examples of neurodegenerative diseases include age related cognitive decline, cognitive impairment progressing to Alzheimer's and senility, Parkinson's disease and Huntington's disease, and amyotrophic lateral sclerosis ("ALS"). The methods and devices disclosed herein are capable of digitally diagnosing and treating children and continuing treatment until the subject becomes an adult, and can provide lifetime treatment based on personalized profiles.

The digital diagnosis and treatment as described herein is well suited for behavioral intervention coupled with biological or chemical therapeutic treatment. By gathering user interaction data as described herein, therapies can be provided for combinations of behavioral intervention data pharmaceutical and biological treatments.

The mobile devices as described herein may comprise sensors to collect data of the subject that can be used as part of the feedback loop so as to improve outcomes and decrease reliance on user input. The mobile device may comprise passive or active sensors as described herein to collect data of the subject subsequent to treatment. The same mobile device or a second mobile device, such as an iPad™ or iPhone™ or similar device, may comprise a software application that interacts with the user to tell the user what to do in improve treatment on a regular basis, e.g. day by day, hour by hour, etc. The user mobile device can be configured to send notifications to the user in response to treatment progress. The mobile device may comprise a drug delivery device configured to monitor deliver amounts of a therapeutic agent delivered to the subject.

The methods and devices disclosed herein are well suited for treatment of both parents and children, for example. Both a parent and a child can receive separate treatments as described herein. For example, neurological condition of the parent can be monitored and treated, and the developmental progress of the child monitored and treated.

The mobile device used to acquire data of the subject can be configured in many ways and may combine a plurality of devices, for example. For example, since unusual sleep patterns may be related to autism, sleep data acquired using the therapeutic apparatus described herein can be used as an additional input to the machine learning training process for autism classifiers used by the diagnostic apparatus described above. The mobile device may comprise a mobile wearable for sleep monitoring for a child, which can be provide as input for diagnosis and treatment and may comprise a component of the feedback loop as described herein.

Many types of sensor, biosensors and data can be used to gather data of the subject and input into the diagnosis and treatment of the subject. For example, work in relation to embodiments suggests that microbiome data can be useful for the diagnosis and treatment of autism. The microbiome data can be collected in many ways known to one of ordinary skill in the art, and may comprise data selected from a stool sample, intestinal lavage, or other sample of the flora of the subject's intestinal track. Genetic data can also be acquired an input into the diagnostic and therapeutic modules. The genetic data may comprise full genomic sequencing of the subject, of sequencing and identification of specific markers.

The diagnostic and therapeutic modules as disclosed herein can receive data from a plurality of sources, such as data acquired from the group consisting of genetic data, floral data, a sleep sensor, a wearable anklet sleep monitor, a booty to monitor sleep, and eye tracking of the subject. The eye tracking can be performed in many ways to determine the direction and duration of gaze. The tracking can be done with glasses, helmets or other sensors for direction and duration of gaze. The data can be collected during a visual session such as a video playback or video game, for example. This data can be acquired and provided to the therapeutic module and diagnostic module as described herein before, during and after treatment, in order to initially diagnose the subject, determine treatment of the subject, modify treatment of the subject, and monitor the subject subsequent to treatment.

The visual gaze, duration of gaze and facial expression information can be acquired with methods and devices known to one of ordinary skill in the art, and acquired as input into the diagnostic and therapeutic modules. The data can be acquired with an app comprising software instructions, which can be downloaded. For example, facial processing has been described by Gloarai et al. "Autism and the development of face processing", Clinical Neuroscience Research 6 (2006) 145-160. An autism research group at Duke University has been conducting the Autism and beyond research study with a software app downloaded onto mobile devices as described on the web page at autismandbeyond.researchkit.duke.edu. Data from such devices is particularly well suited for combination in accordance with the present disclosure. Facial recognition data and gaze data can be input into the diagnostic and therapeutic modules as described herein.

The platforms, systems, devices, methods, and media disclosed herein can provide an activity mode including various activities such as facial expression recognition activities. Facial expression recognition can be performed on one or more images. A computing device, for example a smartphone, can be configured to perform automatic facial expression recognition and deliver real-time social cues as described herein.

The system can track expressive events in faces using the outward-facing camera on the smartphone and read the facial expressions or emotions by passing video and/or image or photographic data to a smartphone app for real-time machine learning-based classification of commonly used emotions (e.g., standardized Ekman "basic" emotions). Examples of such emotions include anger, disgust, fear, happiness, sadness, surprise, contempt, and neutral. The system can then provide real-time social cues about the facial expressions (e.g., "happy," "angry," etc.) to the subject or user through the smartphone. The cues can be visual, shown on the app, and/or auditory, through a speaker on the smartphone, or any combination thereof. The system can also record social responses, such as the amount and type of facial engagement and level of social interaction observed. In some embodiments, the emotion recognition system includes a computer vision pipeline beginning with a robust 23-point face tracker, followed by several lighting optimization steps such as gamma correction, difference of Gaussian filtering, and contrast equalization, or any combination thereof. In some embodiments, a histogram of oriented gradient features is extracted for the whole face and a logistic regression classifier is applied for final emotion prediction. The classifier model can be trained on a number of large existing facial expression recognition databases, as well as additional data gathered from other participants or subjects. In some embodiments, while a session is being conducted, a technique termed "neutral subtraction" allows the system to be calibrated in real-time to specific faces it sees during an interaction, allowing for increased personalize predictions for specific users.

In certain instances, various modes of feedback is provided to the subject (e.g., the child), parents or caregivers, interventionists, clinicians, or any combination thereof. The system can be configured to provide progress feedback to clinicians, for example, through a healthcare provider portal as described herein. Feedback can include performance scores on various activities or games, indicating whether an emotional response is correct, explanation of incorrect answers, improvements or progress (e.g., progress in terms of emotion recognition activities over the past month), or other observations or commentary. Feedback can include performance metrics such as facial attention looking time, correct emotional responses, scores, and other metrics that can be optionally provided in a simple interface for review by clinicians and interventionists so that they can monitor the progress of the subject. Progress feedback can correspond to various domains or subdomains of behavior. For example, progress feedback and/or subject improvements can pertain to the socialization domain and/or specific subdomains including interpersonal relationships, play and leisure, and coping skills. Specific improvements can be tracked, for example, by monitoring and assessing performance and other metrics of the subject during the various digital therapeutic activities. As an example, an inward facing camera and/or microphone can be used to monitor facial engagement, emotional expression, gaze, verbal interactions (e.g., whether child verbally responds to a caregiver's question), and other behavior by the subject.

The digital therapeutic platforms, systems, devices, methods, and media disclosed herein can be configured to evaluate a subject with respect to subdomains and associated deficits as well as determine whether the subject will benefit or improve with digital therapy. For example, interpersonal relationships can entail deficits in social-emotional reciprocity, deficits in nonverbal communicative behaviors used for social interaction, and deficits in developing, maintaining, and understanding relationships. The improvements provided herein can include increases in facial engagement, increases in understanding of emotional expression, and increases in opportunity and motivation for social engagement. The play and leisure subdomain can include deficits in developing, maintaining, and understanding relationships, which can be improved by digital therapeutic games and/or activities that encourage social play. Due to increases in facial engagement and understanding of emotional expression, the subject can become more adept at maintaining relationships. Social coping can entail an insistence on sameness, inflexible adherence to routines, or ritualized patterns of verbal or nonverbal behavior, and due to increases in facial engagement and understanding of emotional expression, the subject can become more able to cope with environmental stressors including that of better understanding social interactions. The therapeutic effects or results of subjects engaging in the therapeutic activities and/or games disclosed herein can be collected as additional data that is used to train machine learning models or classifiers for determining responsiveness to the therapy. In some embodiments, a subject who has been evaluated and positively identified as having (or predicted as having) autism spectrum disorder by a diagnostic or evaluation module can be then assessed by a machine learning model or classifier that predicts or determines the subject will be responsive or will benefit from one or more digital therapies disclosed herein. In some cases, individual activities or games or a plurality of activities or games are predicted to provide a significant therapeutic benefit with respect to one or more forms of social reciprocity. In some cases, the benefit is generally with respect to social reciprocity. Alternatively, or in combination, the benefit is determined with respect to specific domains or subdomains relating to social behavior or reciprocity, or other behavioral deficiencies.

The digital therapeutic can be customized or personalized based on some or all of the diagnostic dimensions used in evaluating a subject for the presence of a disorder, condition, or impairment. For example, a subject may be assessed based on using a machine learning model that predicts the subject will benefit from emotion recognition activities in the socialization domain and/or specific subdomains such as interpersonal relationships, play and leisure, and/or coping skills. This can be based on the various diagnostic dimensions generated during the diagnostic process, which are then incorporated into the therapeutic customization process. A machine learning model may incorporate these dimensions in assessing a predicted or likelihood of improvement or benefit a subject may obtain from specific therapeutics, for example, emotion recognition activities or social reciprocity. In some cases, the subject is predicted to benefit regarding specific behaviors such as increased facial engagement or increased understanding of emotions expressed by others. A significant benefit or improvement may be established statistically using conventional statistical tools or metrics, or can be set (e.g., a threshold such as an average 10% improvement in emotion recognition scores after 3 weeks of treatment). In some embodiments, subject performance is monitored and collected onto a remote database server where it can be anonymized and combined with data for other subjects to form data sets used to train such machine learning models.

The classifiers as disclosed herein are particularly well suited for combination with this data to provide improved therapy and treatment. The data can be stratified and used with a feedback loop as described herein. For example, the feedback data can be used in combination with a drug therapy to determine differential responses and identify responders and non-responders. Alternatively or in combination, the feedback data can be combined with non-drug therapy, such as behavioral therapy (e.g., a digital therapy described herein).

With regards to genetics, recent work suggests that some people may have genes that make them more susceptible to autism. The genetic composition of the subject may render the subject more susceptible to environmental influences, which can cause symptoms and may influence the severity of symptoms. The environmental influence may comprise an insult from a toxin, virus or other substance, for example. Without being bound by any particular theory, this may result in mechanisms that change the regulation of expression genes. The change in expression of genes may be related to change in gastro-intestinal ("GI") flora, and these changes in flora may affect symptoms related to Autism. Alternatively or in combination, an insult to the intestinal microbiome may result in a change in the microbiome of the subject, resulting in the subject having less than ideal homeostasis, which may affect associated symptoms related to Autism. The inventors note that preliminary studies with *B. fragilis* conducted by Sarkis K. Mazmanian and others, suggest changes in this micro-organism can be related to autism and the development of autisms. (See also, "Gut Bacteria May Play a Role in Autism" by Melinda Wenner Moyer, *Scientific American*, Sep. 1, 2014)

The digital diagnostic uses the data collected by the device about the patient, which may include complimentary diagnostic data captured outside the digital diagnostic, with analysis from tools such as machine learning, artificial intelligence, and statistical modeling to assess or diagnose the patient's condition. The digital diagnostic can also provide assessment of a patient's change in state or performance, directly or indirectly via data and meta-data that can be analyzed and evaluated by tools such as machine learning, artificial intelligence, and statistical modeling to provide feedback into the device to improve or refine the diagnoses and potential therapeutic interventions.

Analysis of the data comprising digital diagnostic, digital therapeutics, and corresponding responses, or lack thereof, from the therapeutic interventions can lead to the identification of novel diagnoses for patients and novel therapeutic regimens for both patents and caregivers.

Types of data collected and utilized by the device can include patient and caregiver video, audio, responses to questions or activities, and active or passive data streams from user interaction with activities, games or software features of the device, for example. Such data can also represent patient or caregiver interaction with the device, for example, when performing recommended activities. Specific examples include data from a user's interaction with the device's device or mobile app that captures aspects of the user's behaviors, profile, activities, interactions with the software device, interactions with games, frequency of use, session time, options or features selected, and content and activity preferences. Data may also include streams from various third party devices such as activity monitors, games or interactive content.

Digital therapeutics as described herein can comprise of instructions, feedback, activities or interactions provided to the patient or caregiver by the device. Examples include suggested behaviors, activities, games or interactive sessions with device software and/or third party devices (for example, the Internet of Things "IoT" enabled therapeutic devices as understood by one of ordinary skill in the art).

Figure 23A:
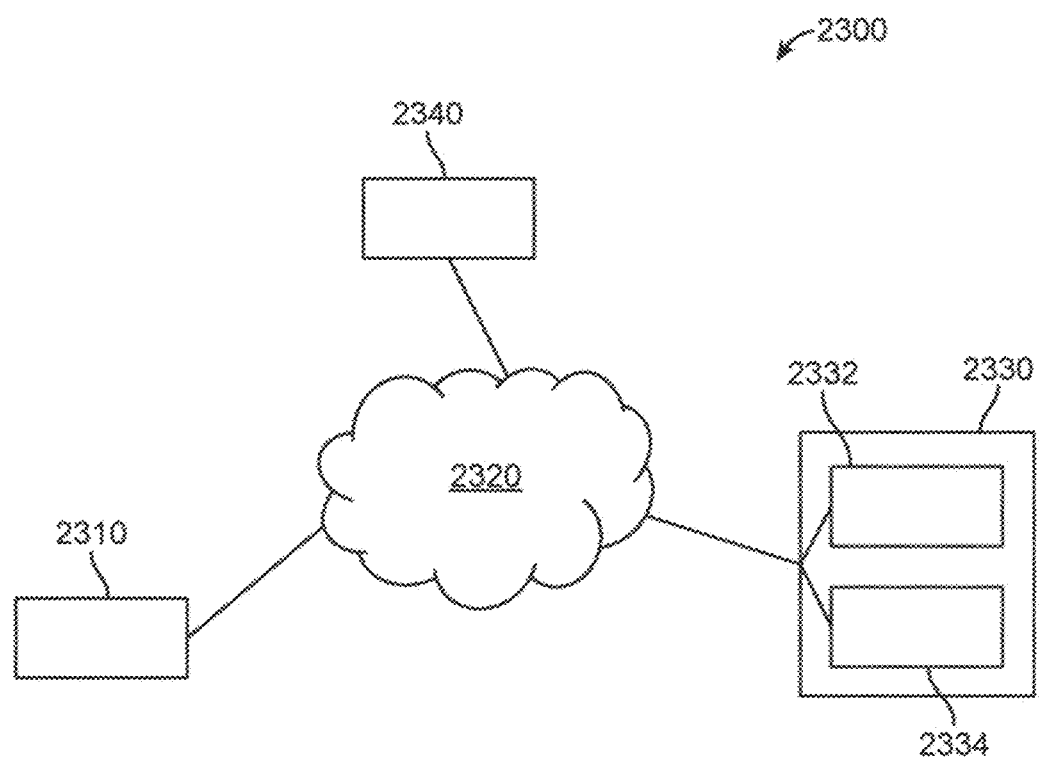
FIG. 23A illustrates a system diagram for a digital personalized medicine platform.

FIG. 23A illustrates a device diagram for a digital personalized medicine platform 2300 for providing diagnosis and therapy related to behavioral, neurological or mental health disorders. The platform 2300 can provide diagnosis and treatment of pediatric cognitive and behavioral conditions associated with developmental delays, for example. A user digital device 2310—for example, a mobile device such as a smart phone, an activity monitor, or a wearable digital monitor—records data and metadata related to a patient. Data may be collected based on interactions of the patient with the device, as well as based on interactions with caregivers and health care professionals. The data may be collected actively, such as by administering tests, recording speech and/or video, and recording responses to diagnostic questions. The data may also be collected passively, such as by monitoring online behavior of patients and caregivers, such as recording questions asked and topics investigated relating to a diagnosed developmental disorder.

The digital device 2310 is connected to a computer network 2320, allowing it to share data with and receive data from connected computers. In particular, the device can communicate with personalized medical device 2330, which comprises a server configured to communicate with digital device 2310 over the computer network 2320. Personalized medical device 2330 comprises a diagnosis module 2332 to provide initial and incremental diagnosis of a patient's developmental status, as well as a therapeutic module 2334 to provide personalized therapy recommendations in response to the diagnoses of diagnosis module 2332.

Each of diagnosis modules 2332 and 2334 communicate with the user digital device 2310 during a course of treatment. The diagnosis module provides diagnostic tests to and receives diagnostic feedback from the digital device 2310, and uses the feedback to determine a diagnosis of a patient. An initial diagnosis may be based on a comprehensive set of tests and questions, for example, while incremental updates may be made to a diagnosis using smaller data samples. For example, the diagnostic module may diagnose autism-related speech delay based on questions asked to the caregiver and tests administered to the patient such as vocabulary or verbal communication tests. The diagnosis may indicate a number of months or years delay in speech abilities. Later tests may be administered and questions asked to update this diagnosis, for example showing a smaller or larger degree of delay.

The diagnosis module communicates its diagnosis to the digital device 2310, as well as to therapy module 2334, which uses the diagnosis to suggest therapies to be performed to treat any diagnosed symptoms. The therapy module 2334 sends its recommended therapies to the digital device 2310, including instructions for the patient and caregivers to perform the therapies recommended over a given time frame. After performing the therapies over the given time frame, the caregivers or patient can indicate completion of the recommended therapies, and a report can be sent from the digital device 2310 to the therapy module 2334. The therapy module 2334 can then indicate to the diagnosis module 2332 that the latest round of therapy is finished, and that a new diagnosis is needed. The diagnostic module 2332 can then provide new diagnostic tests and questions to the digital device 2310, as well as take input from the therapy module of any data provided as part of therapy, such as recordings of learning sessions or browsing history of caregivers or patients related to the therapy or diagnosed condition. The diagnostic module 2332 then provides an updated diagnosis to repeat the process and provide a next step of therapy.

Information related to diagnosis and therapy can also be provided from personalized medical device 2330 to a third-party device 2340, such as a computer device of a health care professional. The health care professional or other third party can be alerted to significant deviations from a therapy schedule, including whether a patient is falling behind an expected schedule or is improving faster than predicted. Appropriate further action can then be taken by the third party based on this provided information.

Figure 23B:
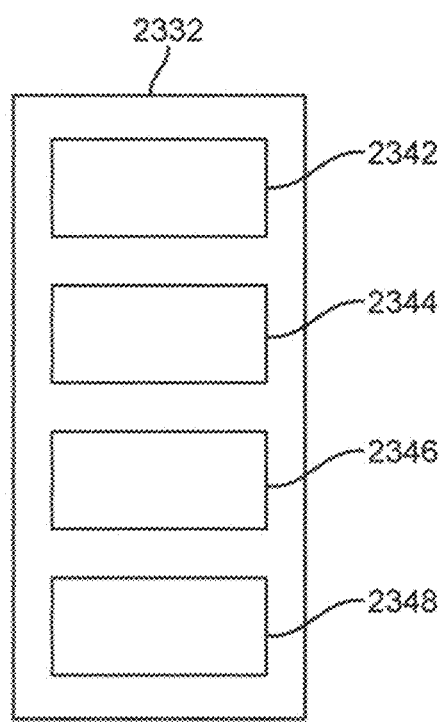
FIG. 23B illustrates a detailed diagram of a diagnosis module.

FIG. 23B illustrates a detailed diagram of diagnosis module 2332. The diagnosis module 2332 comprises a test administration module 2342 that generates tests and corresponding instructions for administration to a subject. The diagnosis module 2332 also comprises a subject data receiving module 2344 in which subject data are received, such as test results; caregiver feedback; meta-data from patient and caregiver interactions with the device; and video, audio, and gaming interactions with the device, for example. A subject assessment module 2346 generates a diagnosis of the subject based on the data from subject data receiving module 2344, as well as past diagnoses of the subject and of similar subjects. A machine learning module 2348 assesses the relative sensitivity of each input to the diagnosis to determine which types of measurement provide the most information regarding a patient's diagnosis. These results can be used by test administration module 2342 to provide tests which most efficiently inform diagnoses and by subject assessment module 2346 to apply weights to diagnosis data in order to improve diagnostic accuracy and consistency. Diagnostic data relating to each treated patient are stored, for example in a database, to form a library of diagnostic data for pattern matching and machine learning. A large number of subject profiles can be simultaneously stored in such a database, for example 10,000 or more.

Figure 23C:
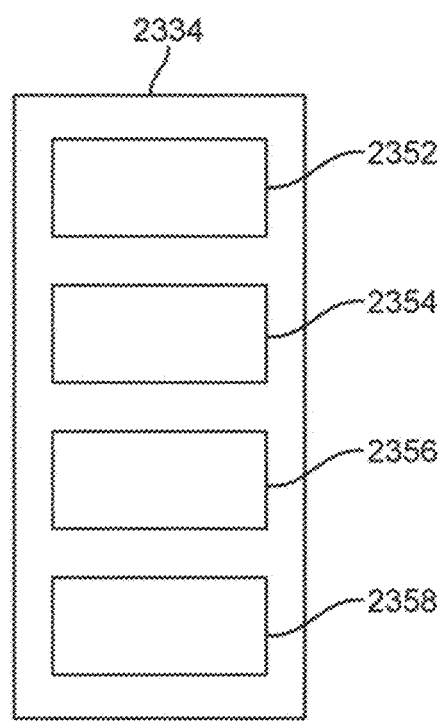
FIG. 23C illustrates a diagram of a therapy module.

FIG. 23C illustrates a detailed diagram of therapy module 2334. Therapy module 2334 comprises a therapy assessment module 2352 that scores therapies based on their effectiveness. A previously suggested therapy is evaluated based on the diagnoses provided by the diagnostic module both before and after the therapy, and a degree of improvement is determined. This degree of improvement is used to score the effectiveness of the therapy. The therapy may have its effectiveness correlated with particular classes of diagnosis; for example, a therapy may be considered effective for subjects with one type of diagnosis but ineffective for subjects with a second type of diagnosis. A therapy matching module 2354 is also provided that compares the diagnosis of the subject from diagnosis module 2332 with a list of therapies to determine a set of therapies that have been determined by the therapy assessment module 2352 to be most effective at treating diagnoses similar to the subject's diagnosis. Therapy recommendation module 2356 then generates a recommended therapy comprising one or more of the therapies identified as promising by the therapy matching module 2354, and sends that recommendation to the subject with instructions for administration of the recommended therapies. Therapy tracking module 2358 then tracks the progress of the recommended therapies, and determines when a new diagnosis should be performed by diagnosis module 2332, or when a given therapy should be continued and progress further monitored. Therapeutic data relating to each patient treated are stored, for example in a database, to form a library of therapeutic data for pattern matching and machine learning. A large number of subject profiles can be simultaneously stored in such a database, for example 10,000 or more. The therapeutic data can be correlated to the diagnostic data of the diagnostic module 2332 to allow a matching of effective therapies (e.g., digital therapies) to diagnoses.

A therapy can comprise a digital therapy. A digital therapy can comprise a single or multiplicity of therapeutic activities or interventions that can be performed by the patient or caregiver. The digital therapeutic can include prescribed interactions with third party devices such as sensors, computers, medical devices and therapeutic delivery devices. Digital therapies can support an FDA approved medical claim, a set of diagnostic codes, or a single diagnostic code.

Figure 24:
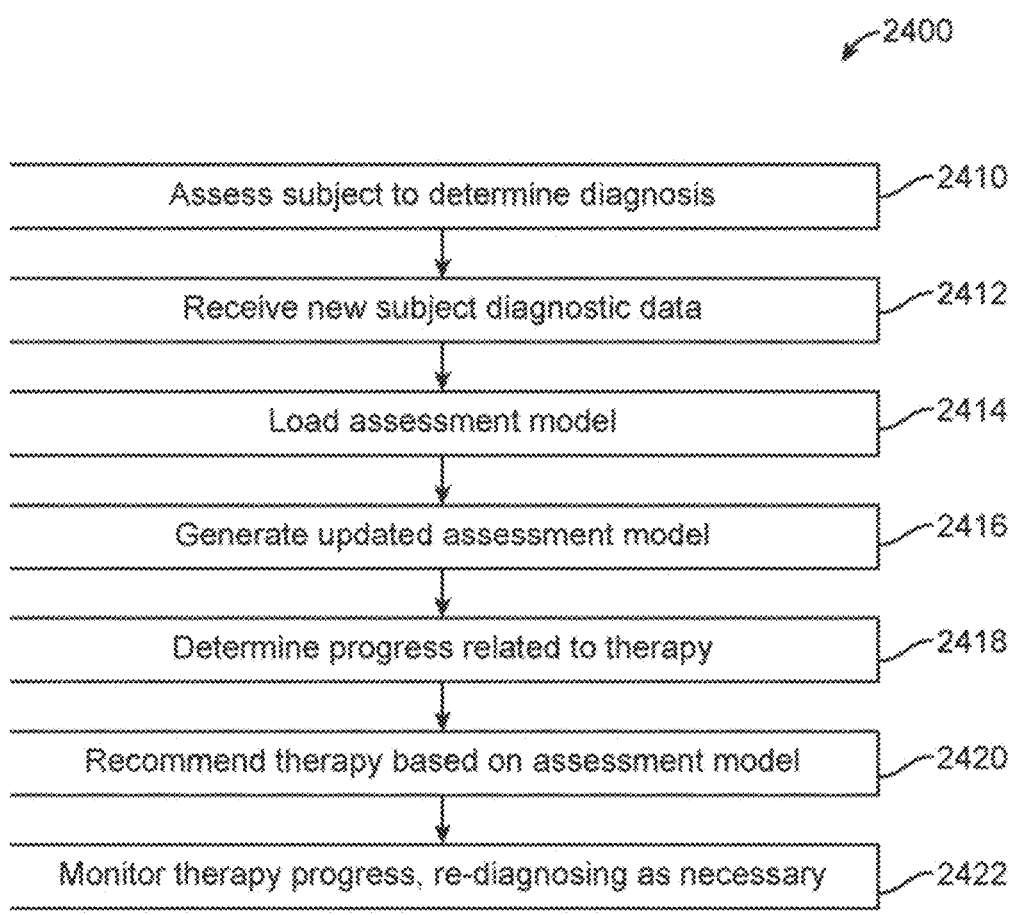
FIG. 24 illustrates a method for diagnosis and therapy to be provided in a digital personalized medicine platform.

FIG. 24 illustrates a method 2400 for diagnosis and therapy to be provided in a digital personalized medicine platform. The digital personalized medicine platform communicates with a subject, which may include a patient with one or more caregivers, to provide diagnoses and recommend therapies.

In step 2410 the diagnosis module assesses the subject to determine a diagnosis, for example by applying diagnostic tests to the subject. The diagnostic tests may be directed at determining a plurality of features and corresponding feature values for the subject. For example, the tests may include a plurality of questions presented to a subject, observations of the subject, or tasks assigned to the subject. The tests may also include indirect tests of the subject, such as feedback from a caregiver of patient performance versus specific behaviors and/or milestones; meta-data from patient and caregiver interactions with the device; and video, audio, and gaming interactions with the device or with third party tools that provide data on patient and caregiver behavior and performance. For initial tests, a more comprehensive testing regimen may be performed, aimed at generating an accurate initial diagnosis. Later testing used to update prior diagnoses to track progress can involve less comprehensive testing and may, for example, rely more on indirect tests such as behavioral tracking and therapy-related recordings and meta-data.

In step 2412, the diagnosis module receives new data from the subject. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The feature values may also comprise recorded feedback, meta-data, and device interaction data as described above.

In step 2414, the diagnosis module can load a previously saved assessment model from a local memory and/or a remote server configured to store the model. Alternatively, if no assessment model exists for the patient, a default model may be loaded, for example, based on one or more initial diagnostic indications.

In step 2416, the new data is fitted to the assessment model to generate an updated assessment model. This assessment model may comprise an initial diagnosis for a previously untreated subject, or an updated diagnosis for a previously treated subject. The updated diagnosis can include a measurement of progress in one or more aspects of a condition, such as memory, attention and joint attention, cognition, behavioral response, emotional response, language use, language skill, frequency of specific behaviors, sleep, socialization, non-verbal communication, and developmental milestones. The analysis of the data to determine progress and current diagnosis can include automated analysis such as question scoring and voice-recognition for vocabulary and speech analysis. The analysis can also include human scoring by analysis reviewing video, audio, and text data.

In step 2418, the updated assessment model is provided to the therapy module, which determines what progress has been made as a result of any previously recommended therapy. The therapy module scores the therapy based on the amount of progress in the assessment model, with larger progress corresponding to a higher score, making a successful therapy and similar therapies more likely to be recommended to subjects with similar assessments in the future. The set of therapies available is thus updated to reflect a new assessment of effectiveness, as correlated with the subject's diagnosis.

In step 2420, a new therapy is recommended based on the assessment model, the degree of success of the previous therapy, if any, and the scores assigned to a collection of candidate therapies based on previous uses of those therapies with the subject and other subjects with similar assessments. The recommended therapy is sent to the subject for administration, along with instructions of a particular span of time to apply it. For example, a therapy might include a language drill to be performed with the patient daily for one week, with each drill to be recorded in an audio file in a mobile device used by a caregiver or the patient.

In step 2422, progress of the new therapy is monitored to determine whether to extend a period of therapy. This monitoring may include periodic re-diagnoses, which may be performed by returning to step 2410. Alternatively, basic milestones may be recorded without a full re-diagnosis, and progress may be compared to a predicted progress schedule generated by the therapy module. For example, if a therapy is unsuccessful initially, the therapy module may suggest repeating it one or more times before either re-diagnosing and suggesting a new therapy or suggesting intervention by medical professionals.

Figure 25:
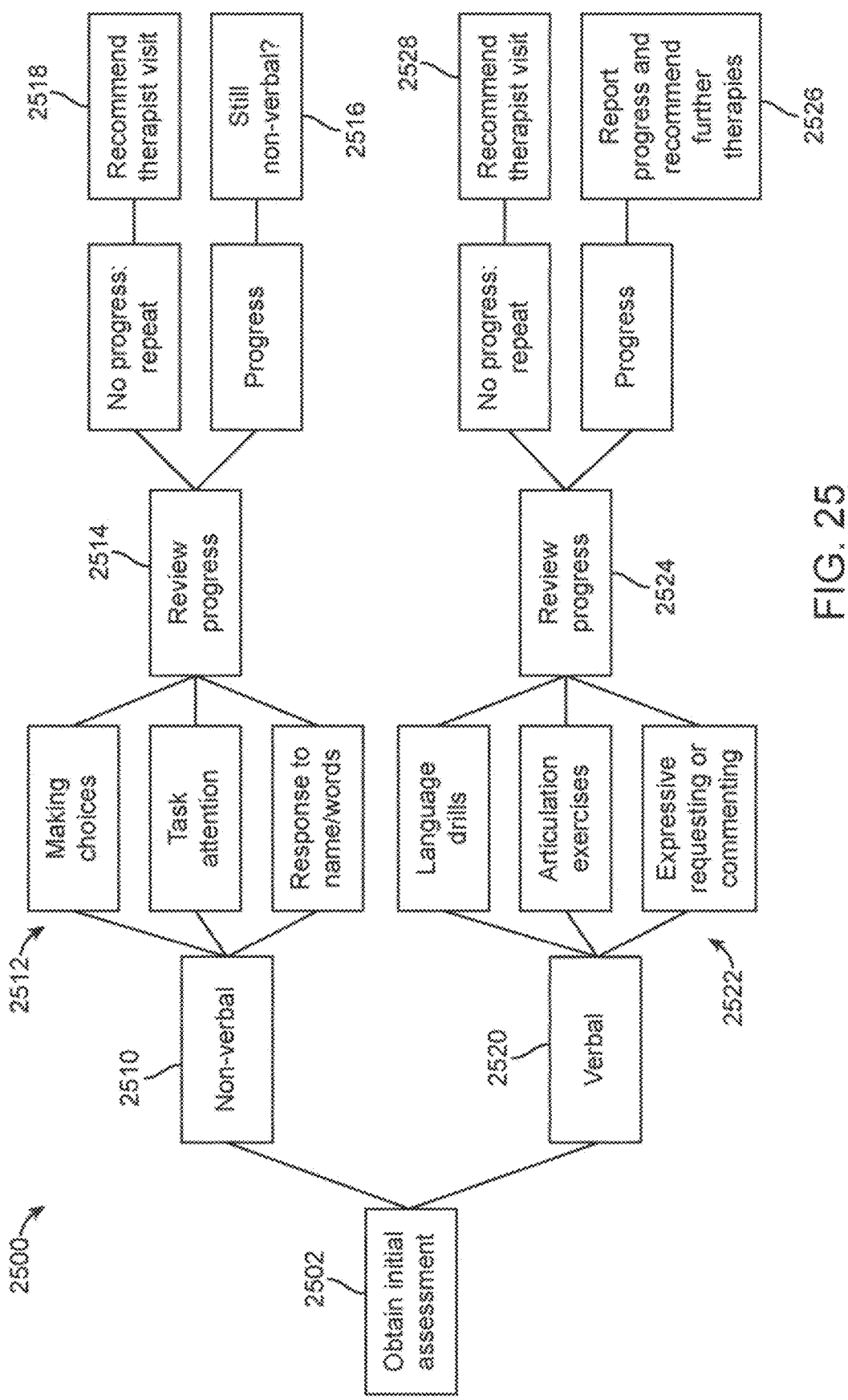
FIG. 25 illustrates a flow diagram showing the handling of autism-related developmental delay.

FIG. 25 illustrates a flow diagram 2500 showing the handling of suspected or confirmed speech and language delay.

In step 2502 an initial assessment is determined by diagnosis module 2532. The initial assessment can assess the patient's performance in one or more domains, such as speech and language use, and assess a degree and type of developmental delay along a number of axes, as disclosed herein. The assessment can further place the subject into one of a plurality of overall tracks of progress; for example, the subject can be assessed as verbal or nonverbal.

If the subject is determined to be non-verbal, as in step 2510, one or more non-verbal therapies 2512 can be recommended by the therapy module 2534, such as tasks related to making choices, paying attention to tasks, or responding to a name or other words. Further suggestions of useful devices and products that may be helpful for progress may also be provided, and all suggestions can be tailored to the subject's needs as indicated by the subject's diagnosis and progress reports.

While applying the recommended therapies, progress is monitored in step 2514 to determine whether a diagnosis has improved at a predicted rate.

If improvement has been measured in step 2514, the device determines whether the subject is still non-verbal in step 2516; if so, then the device returns to step 2510 and generates a new recommended therapy 2512 to induce further improvements.

If no improvement is measured in step 2514, the device can recommend that the therapy be repeated a predetermined number of times. The device may also recommend trying variations in therapy to try and get better results. If such repetitions and variations fail, the device can recommend a therapist visit in step 2518 to more directly address the problems impeding development.

Once the subject is determined to be verbal, as indicated in step 2520, verbal therapies 2522 can be generated by therapy module 2534. For example, verbal therapies 2522 can include one or more of language drills, articulation exercises, and expressive requesting or communicating. Further suggestions of useful devices and products that may be helpful for progress may also be provided, and all suggestions can be tailored to the subject's needs as indicated by the subject's diagnosis and progress reports.

As in the non-verbal track, progress in response to verbal therapies is continually monitored in step 2524 to determine whether a diagnosis has improved at a predicted rate.

If improvement has been measured in step 2524, the device reports on the progress in step 326 and generates a new recommended therapy 2522 to induce further improvements.

If no improvement is detected in step 2524, the device can recommend that the therapy be repeated a predetermined number of times. The device may also recommend trying variations in therapy to try and get better results. If such repetitions and variations fail, the device can recommend a therapist visit in step 2528 to more directly address the problems impeding development.

The steps for non-verbal and verbal therapy can be repeated indefinitely, to the degree needed to stimulate continued learning and progress in the subject, and to prevent or retard regress through loss of verbal skills and abilities. While the specific therapy plan illustrated in FIG. 25 is directed towards pediatric speech and language delay similar plans may be generated for other subjects with developmental or cognitive issues, including plans for adult patients. For example, neurodegenerative conditions and/or age related cognitive decline may be treated with similar diagnosis and therapy schedules, using treatments selected to be appropriate to such conditions. Further conditions that may be treated in adult or pediatric patients by the methods and devices disclosed herein include mood disorders such as depression, OCD, and schizophrenia; cognitive impairment and decline; sleep disorders; addictive behaviors; eating disorders; and behavior related weight management problems.

Figure 26:
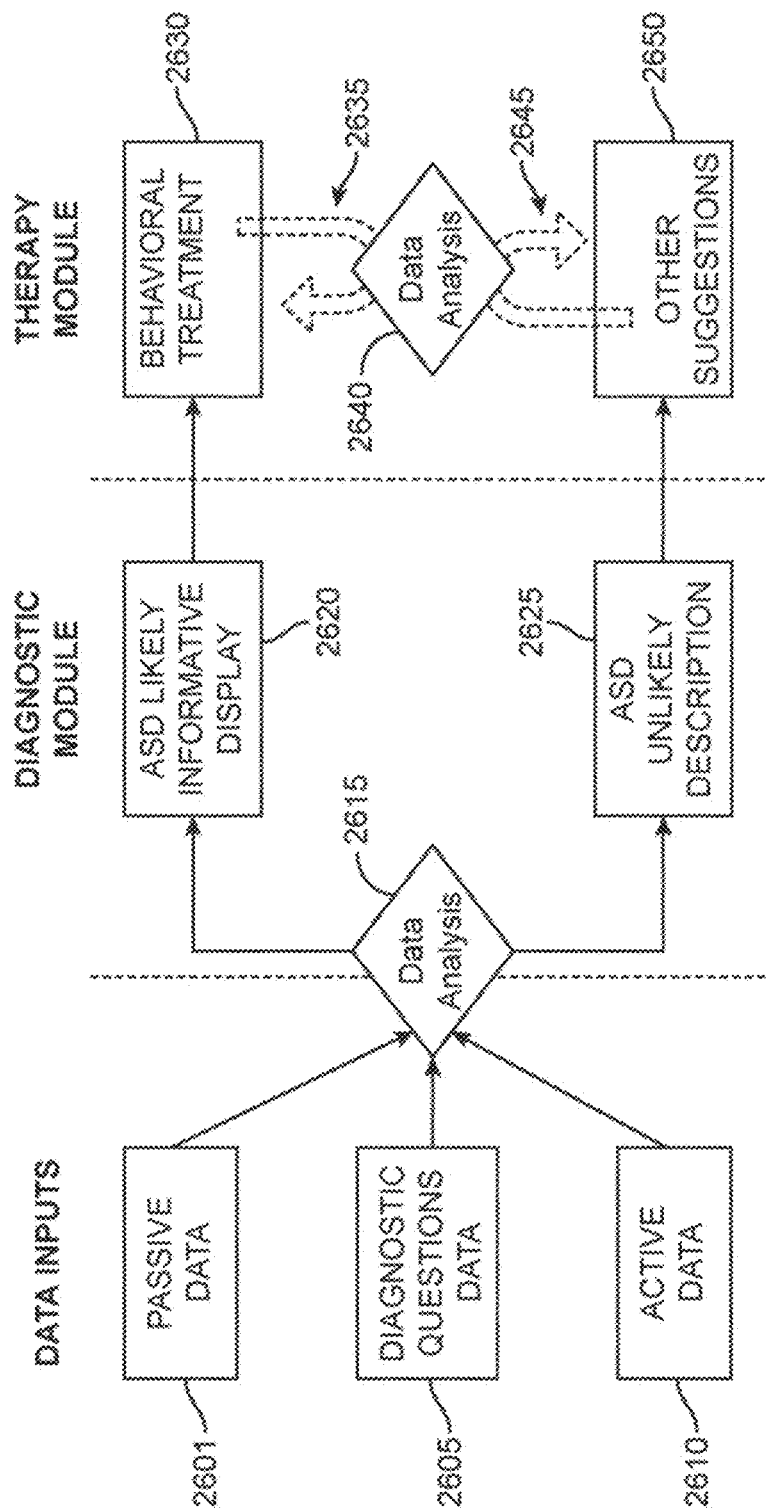
FIG. 26 illustrates an overall of data processing flows for a digital personalized medical system comprising a diagnostic module and a therapeutic module, configured to integrate information from multiple sources.

FIG. 26 illustrates an overall of data processing flows for a digital personalized medical device comprising a diagnostic module and a therapeutic module, configured to integrate information from multiple sources. Data can include passive data sources (2601), passive data can be configured to provide more fine grained information, and can comprise data sets taken over longer periods of time under more natural conditions. Passive data sources can include for example, data collected from wearable devices, data collected from video feeds (e.g. a video-enabled toy, a mobile device, eye tracking data from video playback), information on the dexterity of a subject based on information gathered from three-axis sensors or gyroscopes (e.g. sensors embedded in toys or other devices that the patient may interact with for example at home, or under normal conditions outside of a medical setting), smart devices that measure any single or combination of the following: subject's speech patterns, motions, touch response time, prosody, lexical vocabulary, facial expressions, and other characteristic expressed by the subject. Passive data can comprise data on the motion or motions of the user, and can include subtle information that may or may not be readily detectable to an untrained individual. In some instances, passive data can provide information that can be more encompassing.

Passively collected data can comprise data collected continuously from a variety of environments. Passively collected data can provide a more complete picture of the subject and thus can improve the quality of an assessment. In some instances, for example, passively collected data can include data collected both inside and outside of a medical setting. Passively collected data taken in a medical setting can differ from passively collected data taken from outside a medical setting. Therefore, continuously collected passive data can comprise a more complete picture of a subject's general behavior and mannerisms, and thus can include data or information that a medical practitioner would not otherwise have access to. For example, a subject undergoing evaluation in a medical setting may display symptoms, gestures, or features that are representative of the subject's response to the medical environment, and thus may not provide a complete and accurate picture of the subject's behavior outside of the medical environment under more familiar conditions. The relative importance of one or more features (e.g. features assessed by a diagnostic module) derived from an assessment in the medical environment, may differ from the relative importance of one or more features derived from or assessed outside the clinical setting.

Data can comprise information collected through diagnostic tests, diagnostic questions, or questionnaires (2605). In some instances, data from diagnostic tests (2605) can comprise data collected from a secondary observer (e.g. a parent, guardian, or individual that is not the subject being analyzed). Data can include active data sources (2610), for example data collected from devices configured for tracking eye movement, or measuring or analyzing speech patterns.

As illustrated in FIG. 26, data inputs can be fed into a diagnostic module which can comprise data analysis (2615) using for example a classifier, algorithm (e.g. machine learning algorithm), or statistical model, to make a diagnosis of whether the subject is likely to have a tested disorder (e.g. Autism Spectrum Disorder) (2620) or is unlikely to have the tested disorder (2625). The methods and devices disclosed herein can alternatively be employed to include a third inconclusive category (not depicted in this diagram), which corresponds to the subject requiring additional evaluation to determine whether he/she is or is not likely to have a tested disorder. The methods and devices disclosed herein are not limited to disorders, and may be applied to other cognitive functions, such as behavioral, neurological, mental health, or developmental conditions. The methods and devices may initially categorize a subject into one of the three categories, and subsequently continue with the evaluation of a subject initially categorized as "inconclusive" by collecting additional information from the subject. Such continued evaluation of a subject initially categorized as "inconclusive" may be performed continuously with a single screening procedure (e.g., containing various assessment modules). Alternatively or additionally, a subject identified as belonging to the inconclusive group may be evaluated using separate, additional screening procedures and/or referred to a clinician for further evaluation.

In instances where the subject is determined by the diagnostic model as likely to have the disorder (2620), a secondary party (e.g. medical practitioner, parent, guardian or other individual) may be presented with an informative display. An informative display can provide symptoms of the disorder that can be displayed as a graph depicting covariance of symptoms displayed by the subject and symptoms displayed by the average population. A list of characteristics associated with a particular diagnosis can be displayed with confidence values, correlation coefficients, or other means for displaying the relationship between a subject's performance and the average population or a population comprised of those with a similar disorders.

If the digital personalized medicine device predicts that the user is likely to have a diagnosable condition (e.g. Autism Spectrum Disorder), then a therapy module can provide a behavioral treatment (2630) which can comprise behavioral interventions; prescribed activities or trainings; interventions with medical devices or other therapeutics for specific durations or, at specific times or instances. As the subject undergoes the therapy, data (e.g. passive data and diagnostic question data) can continue to be collected to perform follow-up assessments, to determine for example, whether the therapy is working. Collected data can undergo data analysis (2640) (e.g. analysis using machine learning, statistical modeling, classification tasks, predictive algorithms) to make determinations about the suitability of a given subject. A growth curve display can be used to show the subject's progress against a baseline (e.g. against an age-matched cohort). Performance or progress of the individual may be measured to track compliance for the subject with a suggested behavioral therapy predicted by the therapy module may be presented as a historic and predicted performance on a growth curve. Procedures for assessing the performance of an individual subject may be repeated or iterated (2635) until an appropriate behavioral treatment is identified.

The digital therapeutics treatment methods and devices described with reference to FIGS. 23A-23C and FIGS. 24-26 are particularly well suited for combination with the methods and devices to evaluate subjects with fewer questions described herein with reference to FIGS. 1A to 10. For example, the components of diagnosis module 2332 as described herein can be configured to assess the subject with the decreased set of questions comprising the most relevant question as described herein, and subsequently evaluated with the therapy module 2334 to subsequently assess the subject with subsequent set of questions comprising the most relevant questions for monitoring treatment as described herein.

Figure 27:
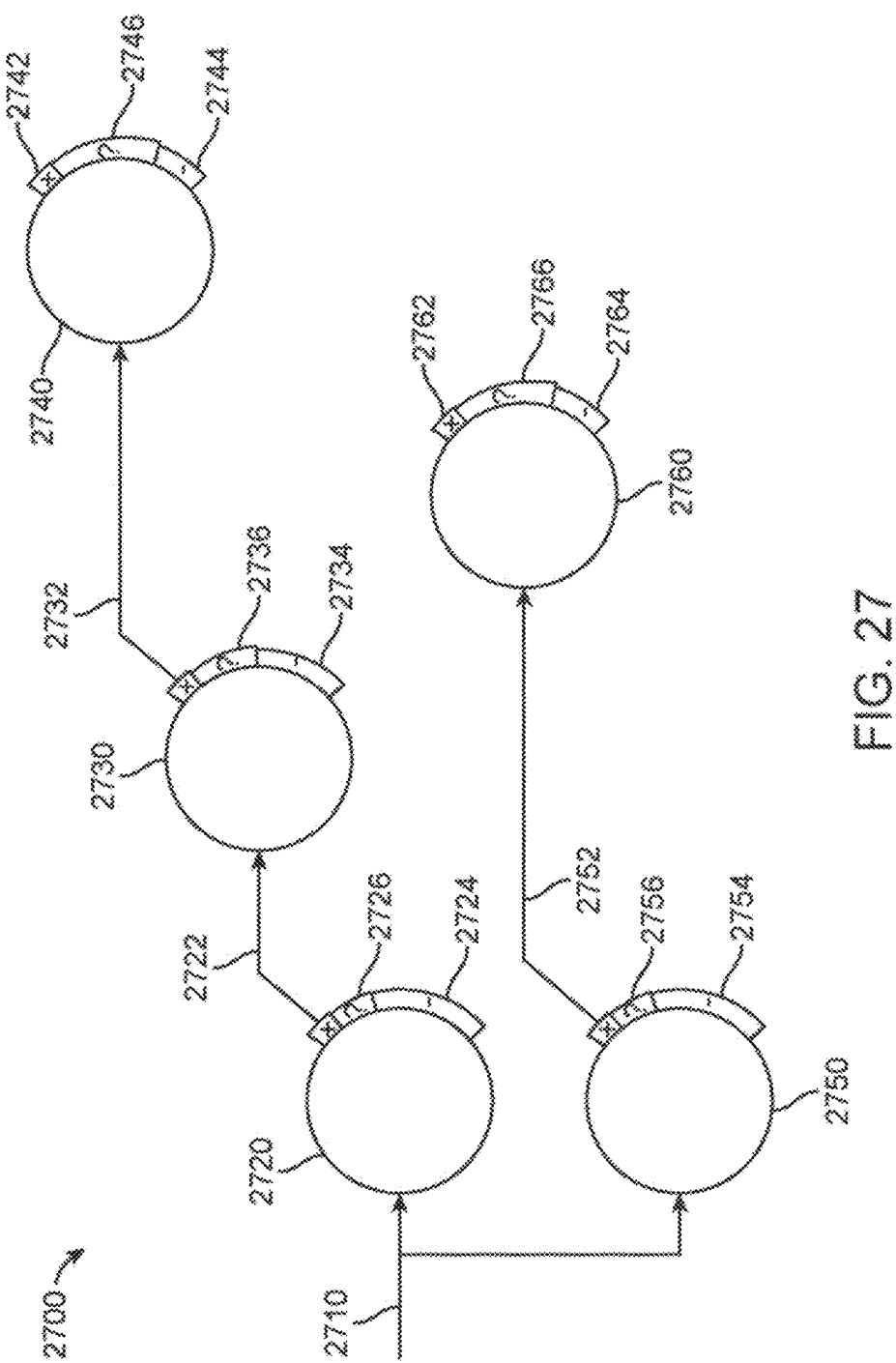
FIG. 27 shows a system for evaluating a subject for multiple clinical indications.

FIG. 27 shows a device 2700 for evaluating a subject for multiple clinical indications. The device 2700 may comprise a plurality of cascaded diagnostic modules (such as diagnostic modules 2720, 2730, 2740, 2750, and 2760). The cascaded diagnostic modules may be operatively coupled (such as in a chain of modules) such that an output from one diagnostic module may form an input to another diagnostic module. As shown in FIG. 27, the device may comprise a social or behavioral delay module 2720, an autism or ADHD module 2730, an autism and ADHD discrimination module 2740, a speech or language delay module 2750, and an intellectual disability module 2760. Modules (e.g., such as the diagnostic modules described with respect to FIG. 27) as described anywhere herein may refer to modules comprising a classifier. Accordingly, a social or behavioral delay module may comprise a social or behavioral delay classifier, an autism or ADHD module may comprise an autism or ADHD classifier, an autism and ADHD discrimination module may comprise an autism and ADHD classifier, a speech or language delay module may comprise a speech or language delay classifier, an intellectual disability module may comprise an intellectual disability classifier, and so forth.

The social or behavioral delay module 2720 may receive information 2710, such as information from an interactive questionnaire described herein. The social or behavioral delay module may utilize any diagnostic operations described herein to determine a social or behavioral delay diagnostic status of the subject. For instance, the social or behavioral delay module may utilize any operations of the procedure 1300 described with respect to FIG. 13 to determine a social or behavioral delay diagnostic status (i.e., whether or not the subject displays behaviors consistent with social or behavioral delay). Upon a determination of the social or behavioral delay diagnostic status, the social or behavioral delay module may output a determination as to whether or not the subject displays social or behavioral delay. The social or behavioral delay module may output a positive identification 2722 indicating that the subject does display social or behavioral delay. The social or behavioral delay module may output a negative indication 2724 indicating that the subject does not display social or behavioral delay. The social or behavioral delay module may output an inconclusive indication 2726 indicating that the social or behavioral delay module has been unable to determine whether or not the subject displays social or behavioral delay.

When the social or behavioral delay module determines that the subject does not display social or behavioral delay or that the result of the social or behavioral delay inquiry is indeterminate, the device may output such a result and halt its inquiry into the subject's social or behavioral health.

However, when the social or behavioral delay module determines that the subject does display social or behavioral delay, the social or behavioral delay module may pass this result, and information 2710, to the autism or ADHD module 2730.

The autism or ADHD delay module may utilize any diagnostic operations described herein to determine an autism or ADHD status of the subject. For instance, the autism or ADHD delay module may utilize any operations of the procedure 1300 described with respect to FIG. 13 to determine an autism or ADHD diagnostic status (i.e., whether or not the subject displays behaviors consistent with autism or ADHD). Upon a determination of the autism or ADHD diagnostic status, the autism or ADHD module may output a determination as to whether or not the subject displays autism or ADHD. The autism or ADHD module may output a positive identification 2732 indicating that the subject does display autism or ADHD. The autism or ADHD module may output a negative indication 2734 indicating that the subject does not display autism or ADHD. The autism or ADHD module may output an inconclusive indication 2736 indicating that the autism or ADHD module has been unable to determine whether or not the subject displays autism or ADHD.

When the autism or ADHD module determines that the subject does not display autism or ADHD or that the result of the autism or ADHD inquiry is indeterminate, the device may output such a result and halt its inquiry into the subject's social or behavioral health. In such a scenario, the device may revert to the earlier diagnosis that the subject displays social or behavioral delay.

However, when the autism or ADHD module determines that the subject does display autism or ADHD, the autism or ADHD module may pass this result, and information 2710, to the autism and ADHD discrimination module 2740.

The autism and ADHD discrimination module may utilize any diagnostic operations described herein to discriminate between autism and ADHD. For instance, the autism and ADHD discrimination module may utilize any operations of the procedure 1300 described with respect to FIG. 13 to discriminate between autism and ADHD for the subject (i.e., to determine whether the subject displays behaviors that are more consistent with autism or with ADHD). Upon a discriminating between autism and ADHD, the autism and ADHD discrimination module may output a determination as to whether displays autism or whether the subject displays ADHD. The autism and ADHD discrimination module may output an indication 2742 indicating that the subject displays autism. The autism and ADHD discrimination module may output an indication 2744 indicating that the subject displays ADHD. The autism and ADHD discrimination module may output an inconclusive indication 2746 indicating that the autism and ADHD discrimination module has been unable to discriminate between whether the subject's behavior is more consistent with autism or with ADHD.

When the autism and ADHD discrimination module determines that the result of the autism and ADHD discrimination inquiry is indeterminate, the device may output such a result and halt its inquiry into the subject's social or behavioral health. In such a scenario, the device may revert to the earlier diagnosis that the subject displays behavior consistent with autism or ADHD.

Alternatively or in combination, the autism and ADHD discrimination module may be further configured to pass information 2710 to one or more additional modules. For instance, the autism and ADHD discrimination module may be configured to pass information to an obsessive compulsive disorder module (not shown in FIG. 27). The obsessive compulsive disorder module may make a determination as to whether a subject displays behavior consistent with obsessive compulsive disorder using any of the platforms, systems, devices, methods, and media described herein (such as any operations of the procedure 1300).

Alternatively or in combination, the speech or language delay module 2750 may receive the information 2710. The speech or language delay module may utilize any diagnostic operations described herein to determine a speech or language delay diagnostic status of the subject. For instance, the speech or language delay module may utilize any operations of the procedure 1300 described with respect to FIG. 13 to determine a speech or language delay diagnostic status (i.e., whether or not the subject displays behaviors consisting with speech or language delay). Upon a determination of the speech or language delay diagnostic status, the speech or language delay module may output a determination as to whether or not the subject displays speech or language delay. The speech or language delay module may output a positive identification 2752 indicating that the subject does display speech or language delay. The speech or language delay module may output a negative indication 2754 indicating that the subject does not display speech or language delay. The speech or language delay module may output an inconclusive indication 2756 indicating that the speech or language delay module has been unable to determine whether or not the subject displays speech or language delay.

When the speech or language delay module determines that the subject does not display speech or language delay or that the result of the speech or language delay inquiry is indeterminate, the device may output such a result and halt its inquiry into the subject's speech or language health.

However, when the speech or language delay module determines that the subject does display speech or language delay, the speech or language delay module may pass this result, and information 2710, to the intellectual disability module 2760.

The intellectual disability module may utilize any diagnostic operations described herein to determine an intellectual disability status of the subject. For instance, the intellectual disability module may utilize any operations of the procedure 1300 described with respect to FIG. 13 to determine an intellectual disability diagnostic status (i.e., whether or not the subject displays behaviors consistent with intellectual disability). Upon a determination of the intellectual disability diagnostic status, the intellectual disability module may output a determination as to whether or not the subject displays intellectual disability. The intellectual disability module may output a positive identification 2762 indicating that the subject does display intellectual disability. The intellectual disability module may output a negative indication 2764 indicating that the subject does not display intellectual disability. The intellectual disability module may output an inconclusive indication 2766 indicating that the intellectual disability module has been unable to determine whether or not the subject displays intellectual disability.

When the intellectual disability module determines that the subject does not display intellectual disability or that the result of the intellectual disability inquiry is indeterminate, the device may output such a result and halt its inquiry into the subject's speech or language health. In such a scenario, the device may revert to the earlier diagnosis that the subject displays speech or language delay.

Alternatively or in combination, the intellectual disability module may be further configured to pass information 2710 to one or more additional modules. For instance, the intellectual disability module may be configured to pass information to a dyslexia module (not shown in FIG. 27). The dyslexia module may make a determination as to whether a subject displays behavior consistent with dyslexia using any of the platforms, systems, devices, methods, and media described herein (such as any operations of the procedure 1300).

Though described with reference to social or behavioral delay, autism, ADHD, obsessive compulsive disorder, speech or language delay, intellectual disability, and dyslexia, the device 2700 may comprise any number of modules (such as 1, 2, 3, 4, 5, 6, 7, 8, 9, 10, or more than 10 modules) that may provide a diagnostic status for any behavioral disorder. The modules may be operatively coupled (such as cascaded or chained) in any possible order.

Disclosed herein, in various embodiments, are machine learning methods for analyzing input data including, for example, images in the case of emotion detection classifiers, parent/video analyst/clinician questionnaires in the case of detection of the presence of a behavioral, developmental, or cognitive disorder or condition, user input or performance (passive or active) or interactions with a digital therapy device (e.g., games or activities configured to promote emotion recognition), and other sources of data described herein.

Disclosed herein, in various aspects, are platforms, systems, devices, methods, and media incorporating machine learning techniques (e.g., deep learning utilizing convolutional neural networks). In some cases, provided herein is an AI transfer learning framework for the analysis of image data for emotion detection.

In certain aspects, disclosed herein are machine learning frameworks for generating models or classifiers that detect one or more disorders or conditions, and/or models or classifiers that determine a responsiveness or efficacy or likelihood of improvement using a digital therapy such as one configured to promote social reciprocity. These models or classifiers can be implemented in any of the systems or devices disclosed herein such as smartphones, mobile computing devices, or wearable devices.

In some embodiments, the machine learning model or classifier exhibits performance metrics such as accuracy, sensitivity, specificity, positive predictive value, negative predictive value, and/or AUC for an independent sample set. In some embodiments, the model is evaluated for performance using metrics such as higher accuracy, sensitivity, specificity, positive predictive value, negative predictive value, and/or AUC for an independent sample set. In some embodiments, the model provides an accuracy of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, or 500 independent samples. In some embodiments, the model provides a sensitivity (true positive rate) of at least 70%, at least 75%, at least 80%, at least 85%, at least 90%, at least 91%, at least 92%, at least 93%, at least 94%, at least 95%, at least 96%, at least 97%, at least 98%, at least 99%, and/or a specificity (true negative rate) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, or 500 independent samples. In some embodiments, the model provides a positive predictive value (PPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, or 500 independent samples. In some embodiments, the model provides a negative predictive value (NPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, or 500 independent samples. In some embodiments, the model has an AUC of at least 0.7, 0.75, 0.8, 0.85, 0.9, 0.91, 0.92, 0.93, 0.94, 0.95, 0.96, 0.97, 0.98 or 0.99 when tested against at least 100, 200, 300, 400, or 500 independent samples.

In some embodiments, the machine learning algorithm or model configured for detecting emotions in one or more images comprises a neural network.

In some embodiments, transfer learning is used to generate a more robust model by first generating a pre-trained model trained on a large dataset of images (e.g., from ImageNet), freezing a portion of the model (e.g., several layers of a convolutional neural network), and transferring the frozen portion into a new model that is trained on a more targeted data set (e.g., images accurately labeled with the correct facial expression or emotion).

In some embodiments, a classifier or trained machine learning model of the present disclosure comprises a feature space. In some embodiments, a feature space comprises information such as pixel data from an image. When training the model, training data such as image data is input into the machine learning algorithm which processes the input features to generate a model. In some embodiments, the machine learning model is provided with training data that includes the classification (e.g., diagnostic or test result), thus enabling the model to be trained by comparing its output with the actual output to modify and improve the model. This is often referred to as supervised learning. Alternatively, in some embodiments, the machine learning algorithm can be provided with unlabeled or unclassified data, which leaves the algorithm to identify hidden structure amongst the cases (referred to as unsupervised learning). Sometimes, unsupervised learning is useful for identifying the features that are most useful for classifying raw data into separate cohorts.

In some embodiments, one or more sets of training data are used to train a machine learning model. In some embodiments, the machine learning algorithm utilizes a predictive model such as a neural network, a decision tree, a support vector machine, or other applicable model. In some embodiments, the machine learning algorithm is selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g., linear, logistic, multivariate, association rule learning, deep learning, dimensionality reduction and ensemble selection algorithms. In some embodiments, the machine learning model is selected from the group consisting of: a support vector machine (SVM), a Naïve Bayes classification, a random forest, and an artificial neural network. Machine learning techniques include bagging procedures, boosting procedures, random forest, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

The platforms, systems, devices, methods, and media described anywhere herein may be used as a basis for a treatment plan, or for administration of a drug, for a disorder diagnosed by any device or method for diagnosis described herein.

The platforms, systems, devices, methods, and media described anywhere herein may be used to administer a drug to treat acute stress disorder, such as propranolol, citalopram, escitalopram, sertraline, paroxetine, fluoxetine, venlafaxine, mirtazapine, nefazodone, carbamazepine, divalproex, lamotrigine, topiramate, prazosin, phenelzine, imipramine, diazepam, clonazepam, lorazepam, or alprazolam.

The platforms, systems, devices, methods, and media described anywhere herein may be used to administer a drug to treat adjustment disorder, such as buspirone, escitalopram, sertraline, paroxetine, fluoxetine, diazepam, clonazepam, lorazepam, or alprazolam.

The platforms, systems, devices, methods, and media described anywhere herein may be used to administer a drug to treat agoraphobia, such as diazepam, clonazepam, lorazepam, alprazolam, citalopram, escitalopram, sertraline, paroxetine, fluoxetine, or buspirone.

The platforms, systems, devices, methods, and media described anywhere herein may be used to administer a drug to treat Alzheimer's disease, such as donepezil, galantamine, memantine, or rivastigmine.

The platforms, systems, devices, methods, and media described anywhere herein may be used to administer a drug to treat anorexia nervosa, such as olanzapine, citalopram, escitalopram, sertraline, paroxetine, or fluoxetine.

The platforms, systems, devices, methods, and media described anywhere herein may be used to administer a drug to treat anxiety disorders, such as sertraline, escitalopram, citalopram, fluoxetine, diazepam, buspirone, venlafaxine, duloxetine, imipramine, desipramine, clomipramine, lorazepam, clonazepam, or pregabalin.

The platforms, systems, devices, methods, and media described anywhere herein may be used to administer a drug to treat attachment disorder.

The platforms, systems, devices, methods, and media described anywhere herein may be used to administer a drug to treat attention deficit/hyperactivity disorder (ADHD/ADD), such as amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or modafinil (for instance, in a dosage of 100 mg to 500 mg).

The platforms, systems, devices, methods, and media described anywhere herein may be used to administer a drug to treat autism or autism spectrum disorders, such as risperidone (for instance, in a dosage of 0.5 mg to 20 mg), quetiapine (for instance, in a dosage of 25 mg to 1000 mg), amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or aripiprazole (for instance, in a dosage of 1 mg to 10 mg).

The platforms, systems, devices, methods, and media described anywhere herein may be used to administer a drug to treat bereavement, such as citalopram, duloxetine, or doxepin.

The platforms, systems, devices, methods, and media described anywhere herein may be used to administer a drug to treat binge eating disorder, such as lisdexamfetamine.

The platforms, systems, devices, methods, and media described anywhere herein may be used to administer a drug to treat bipolar disorder, such as topiramate, lamotrigine, oxcarbazepine, haloperidol, risperidone, quetiapine, olanzapine, aripiprazole, or fluoxetine.

The platforms, systems, devices, methods, and media described anywhere herein may be used to administer a drug to treat body dysmorphic disorder, such as sertraline, escitalopram, or citalopram.

The platforms, systems, devices, methods, and media described anywhere herein may be used to administer a drug to treat brief psychotic disorder, such as clozapine, asenapine, olanzapine, or quetiapine.

The platforms, systems, devices, methods, and media described anywhere herein may be used to administer a drug to treat bulimia nervosa, such as sertraline, or fluoxetine.

The platforms, systems, devices, methods, and media described anywhere herein may be used to administer a drug to treat conduct disorder, such as lorazepam, diazepam, or clobazam.

The platforms, systems, devices, methods, and media described anywhere herein may be used to administer a drug to treat cyclothymic disorder.

The platforms, systems, devices, methods, and media described anywhere herein may be used to administer a drug to treat delusional disorder, such as clozapine, asenapine, risperidone, venlafaxine, bupropion, or buspirone.

The platforms, systems, devices, methods, and media described anywhere herein may be used to administer a drug to treat depersonalization disorder, such as sertraline, fluoxetine, alprazolam, diazepam, or citalopram.

The platforms, systems, devices, methods, and media described anywhere herein may be used to administer a drug to treat depression, such as sertraline, fluoxetine, citalopram, bupropion, escitalopram, venlafaxine, aripiprazole, buspirone, vortioxetine, or vilazodone.

The platforms, systems, devices, methods, and media described anywhere herein may be used to administer a drug to treat disinhibited social engagement disorder.

The platforms, systems, devices, methods, and media described anywhere herein may be used to administer a drug to treat disruptive mood dysregulation disorder, such as quetiapine, clozapine, asenapine, or pimavanserin.

The platforms, systems, devices, methods, and media described anywhere herein may be used to administer a drug to treat dissociative amnesia, such as alprazolam, diazepam, lorazepam, or chlordiazepoxide.

The platforms, systems, devices, methods, and media described anywhere herein may be used to administer a drug to treat dissociative disorder, such as bupropion, vortioxetine, or vilazodone.

The platforms, systems, devices, methods, and media described anywhere herein may be used to administer a drug to treat dissociative fugue, such as amobarbital, aprobarbital, butabarbital, or methohexital.

The platforms, systems, devices, methods, and media described anywhere herein may be used to administer a drug to treat dissociative identity disorder.

The platforms, systems, devices, methods, and media described anywhere herein may be used to administer a drug to treat dyslexia, such as amphetamine (for instance, in a dosage of 5 mg to 50 mg), dextroamphetamine (for instance, in a dosage of 5 mg to 60 mg), methylphenidate (for instance, in a dosage of 5 mg to 60 mg), methamphetamine (for instance, in a dosage of 5 mg to 25 mg), dexmethylphenidate (for instance, in a dosage of 2.5 mg to 40 mg), guanfacine (for instance, in a dosage of 1 mg to 10 mg), atomoxetine (for instance, in a dosage of 10 mg to 100 mg), lisdexamfetamine (for instance, in a dosage of 30 mg to 70 mg), clonidine (for instance, in a dosage of 0.1 mg to 0.5 mg), or modafinil (for instance, in a dosage of 100 mg to 500 mg).

The platforms, systems, devices, methods, and media described anywhere herein may be used to administer a drug to treat dysthymic disorder, such as bupropion, venlafaxine, sertraline, or citalopram.

The platforms, systems, devices, methods, and media described anywhere herein may be used to administer a drug to treat eating disorders, such as olanzapine, citalopram, escitalopram, sertraline, paroxetine, or fluoxetine.

The platforms, systems, devices, methods, and media described anywhere herein may be used to administer a drug to treat expressive language disorder.

The platforms, systems, devices, methods, and media described anywhere herein may be used to administer a drug to treat gender dysphoria, such as estrogen, prostogen, or testosterone.

The platforms, systems, devices, methods, and media described anywhere herein may be used to administer a drug to treat generalized anxiety disorder, such as venlafaxine, duloxetine, buspirone, sertraline, or fluoxetine.

The platforms, systems, devices, methods, and media described anywhere herein may be used to administer a drug to treat hoarding disorder, such as buspirone, sertraline, escitalopram, citalopram, fluoxetine, paroxetine, venlafaxine, or clomipramine.

The platforms, systems, devices, methods, and media described anywhere herein may be used to administer a drug to treat intellectual disability.

The platforms, systems, devices, methods, and media described anywhere herein may be used to administer a drug to treat intermittent explosive disorder, such as asenapine, clozapine, olanzapine, or pimavanserin.

The platforms, systems, devices, methods, and media described anywhere herein may be used to administer a drug to treat kleptomania, such as escitalopram, fluvoxamine, fluoxetine, or paroxetine.

The platforms, systems, devices, methods, and media described anywhere herein may be used to administer a drug to treat mathematics disorder.

The platforms, systems, devices, methods, and media described anywhere herein may be used to administer a drug to treat obsessive-compulsive disorder, such as buspirone (for instance, in a dosage of 5 mg to 60 mg), sertraline (for instance, in a dosage of up to 200 mg), escitalopram (for instance, in a dosage of up to 40 mg), citalopram (for instance, in a dosage of up to 40 mg), fluoxetine (for instance, in a dosage of 40 mg to 80 mg), paroxetine (for instance, in a dosage of 40 mg to 60 mg), venlafaxine (for instance, in a dosage of up to 375 mg), clomipramine (for instance, in a dosage of up to 250 mg), or fluvoxamine (for instance, in a dosage of up to 300 mg).

The platforms, systems, devices, methods, and media described anywhere herein may be used to administer a drug to treat oppositional defiant disorder.

The platforms, systems, devices, methods, and media described anywhere herein may be used to administer a drug to treat panic disorder, such as bupropion, vilazodone, or vortioxetine.

The platforms, systems, devices, methods, and media described anywhere herein may be used to administer a drug to treat Parkinson's disease, such as rivastigmine, selegiline, rasagiline, bromocriptine, amantadine, cabergoline, or benztropine.

The platforms, systems, devices, methods, and media described anywhere herein may be used to administer a drug to treat pathological gambling, such as bupropion, vilazodone, or vartioxetine.

The platforms, systems, devices, methods, and media described anywhere herein may be used to administer a drug to treat pica.

The platforms, systems, devices, methods, and media described anywhere herein may be used to administer a drug to treat postpartum depression, such as sertraline, fluoxetine, citalopram, bupropion, escitalopram, venlafaxine, aripiprazole, buspirone, vortioxetine, or vilazodone.

The platforms, systems, devices, methods, and media described anywhere herein may be used to administer a drug to treat posttraumatic stress disorder, such as sertraline, fluoxetine, or paroxetine.

The platforms, systems, devices, methods, and media described anywhere herein may be used to administer a drug to treat premenstrual dysphoric disorder, such as estradiol, drospirenone, sertraline, citalopram, fluoxetine, or buspirone.

The platforms, systems, devices, methods, and media described anywhere herein may be used to administer a drug to treat pseudobulbar affect, such as dextromethorphan hydrobromide, or quinidine sulfate.

The platforms, systems, devices, methods, and media described anywhere herein may be used to administer a drug to treat pyromania, such as clozapine, asenapine, olanzapine, paliperidone, or quetiapine.

The platforms, systems, devices, methods, and media described anywhere herein may be used to administer a drug to treat reactive attachment disorder.

The platforms, systems, devices, methods, and media described anywhere herein may be used to administer a drug to treat reading disorder.

The platforms, systems, devices, methods, and media described anywhere herein may be used to administer a drug to treat Rett's syndrome.

The platforms, systems, devices, methods, and media described anywhere herein may be used to administer a drug to treat rumination disorder.

The platforms, systems, devices, methods, and media described anywhere herein may be used to administer a drug to treat schizoaffective disorder, such as sertraline, carbamazepine, oxcarbazepine, valproate, haloperidol, olanzapine, or loxapine.

The platforms, systems, devices, methods, and media described anywhere herein may be used to administer a drug to treat schizophrenia, such as chlorpromazine, haloperidol, fluphenazine, risperidone, quetiapine, ziprasidone, olanzapine, perphenazine, aripiprazole, or prochlorperazine.

The platforms, systems, devices, methods, and media described anywhere herein may be used to administer a drug to treat schizophreniform disorder, such as paliperidone, clozapine, risperidone.

The platforms, systems, devices, methods, and media described anywhere herein may be used to administer a drug to treat seasonal affective disorder, such as sertraline, or fluoxetine.

The platforms, systems, devices, methods, and media described anywhere herein may be used to administer a drug to treat separation anxiety disorder.

The platforms, systems, devices, methods, and media described anywhere herein may be used to administer a drug to treat shared psychotic disorder, such as clozapine, pimavanserin, risperidone, or lurasidone.

The platforms, systems, devices, methods, and media described anywhere herein may be used to administer a drug to treat social (pragmatic) communication disorder.

The platforms, systems, devices, methods, and media described anywhere herein may be used to administer a drug to treat social anxiety phobia, such as amitriptyline, bupropion, citalopram, fluoxetine, sertraline, or venlafaxine.

The platforms, systems, devices, methods, and media described anywhere herein may be used to administer a drug to treat somatic symptom disorder.

The platforms, systems, devices, methods, and media described anywhere herein may be used to administer a drug to treat specific phobia, such as diazepam, estazolam, quazepam, or alprazolam.

The platforms, systems, devices, methods, and media described anywhere herein may be used to administer a drug to treat stereotypic movement disorder, such as risperidone, or clozapine.

The platforms, systems, devices, methods, and media described anywhere herein may be used to administer a drug to treat stuttering.

The platforms, systems, devices, methods, and media described anywhere herein may be used to administer a drug to treat Tourette's disorder, such as haloperidol, fluphenazine, risperidone, ziprasidone, pimozide, perphenazine, or aripiprazole.

The platforms, systems, devices, methods, and media described anywhere herein may be used to administer a drug to treat transient tic disorder, such as guanfacine, clonidine, pimozide, risperidone, citalopram, escitalopram, sertraline, paroxetine, or fluoxetine.

Figure 28:
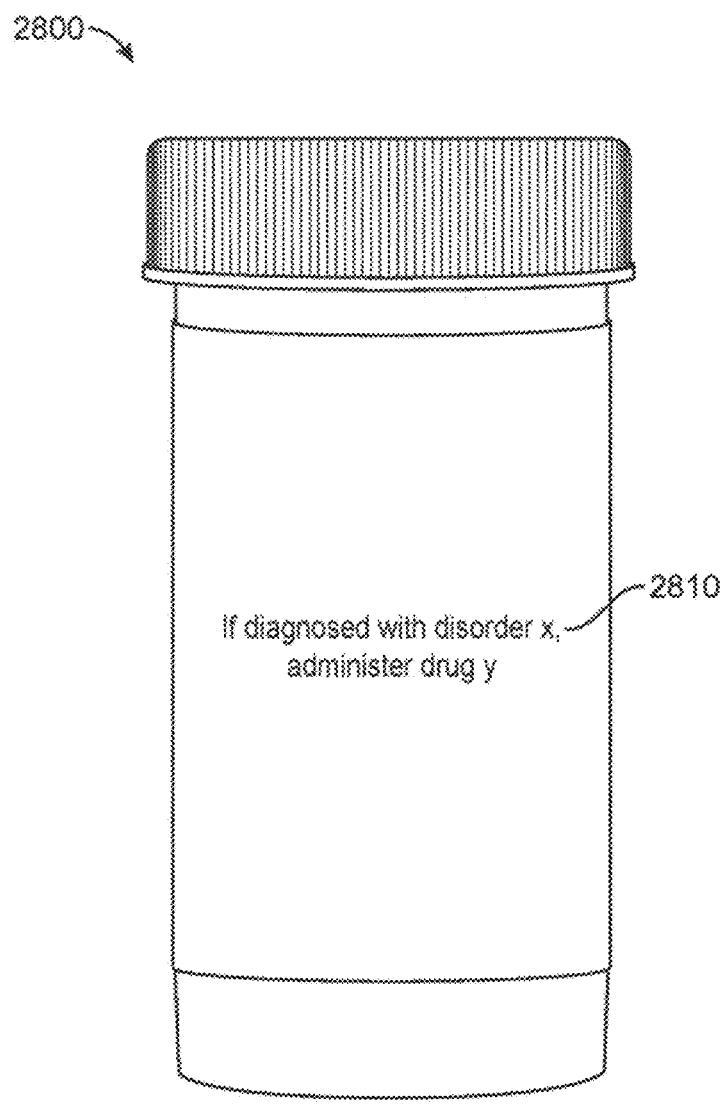
FIG. 28 shows a drug that may be administered in response to a diagnosis by the platforms, systems, devices, methods and media described herein.

FIG. 28 shows a drug that may be administered in response to a diagnosis by the platforms, systems, devices, methods, and media described herein. The drug may be contained within a container 2800, such as a pill bottle. The container may have a label 2810 bearing instructions "If diagnosed with disorder x, administer drug y". The disorder x may be any disorder described herein. The drug y may be any drug described herein.

Figure 29:
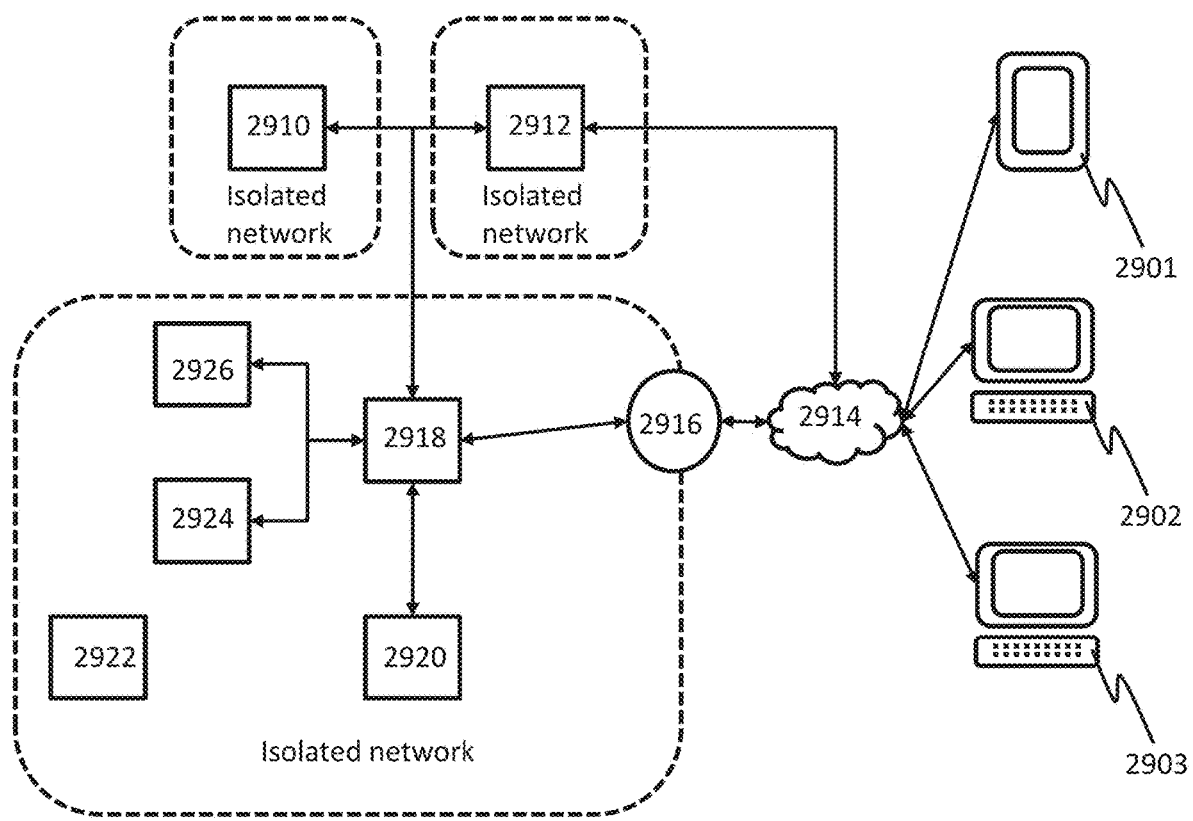
FIG. 29 shows a diagram of a platform for assessing an individual as described herein.

FIG. 29 shows a diagram of a platform for assessing an individual as described herein. The platform architecture as illustrated in FIG. 29 includes the various sources of input, specifically the caregiver or user mobile application or device 2901, the video analyst portal 2902, and the healthcare provider dashboard 2903. These input data sources communicate with the rest of the platform via the internet 2914 which itself interfaces with a video storage service 2912 and a load balancer gateway 2916. The load balancer gateway 2916 is in operative communication with the application server 2918 which utilizes an index service 2924 and an algorithm and questionnaire service 2926 to assist with data analysis. The application server 2918 can source data from the video storage service 2912 and the primary database 2910 for use in the analysis. A logging or audit service may also be used to document any events such as what user data is accessed and how it is used in order to help ensure privacy and HIPAA compliance.

Figure 30:
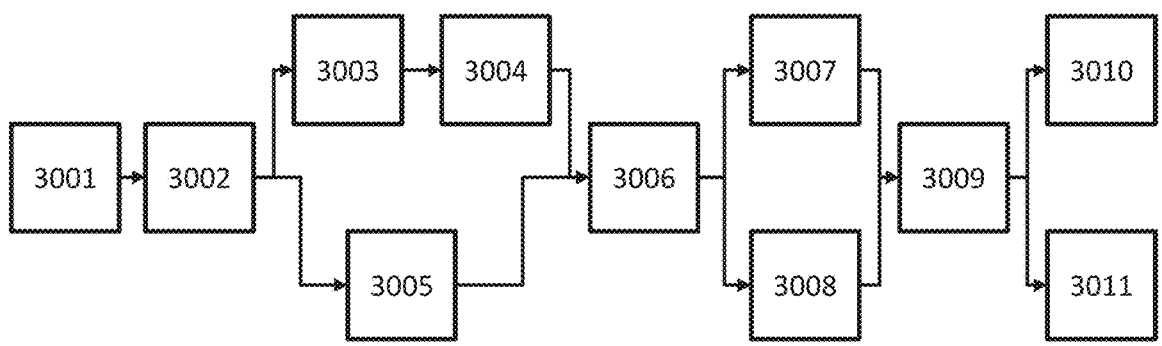
FIG. 30 shows a non-limiting flow diagram for evaluating an individual.

FIG. 30 shows a non-limiting flow diagram for evaluating an individual. A caregiver or healthcare provider raises concerns about a child 3001 after which a ASD device is prescribed for the child 3002 in which the healthcare provider determines the use of this device is appropriate and explains its use to the caregiver. Later, the caregiver completes a first module including a caregiver questionnaire and uploads the response and 2 videos 3003. Next, a video analyst evaluates the uploaded videos 3004 and provides a response to complete the second module. The healthcare provider also has discretion to complete a third module including a clinician/healthcare provider questionnaire 3005. This third module may be completed during the appointment with the child or outside of the appointment. The device then returns the result of the assessment 3006. In the case of a positive assessment 3007 or a negative assessment 3008 for ASD, the healthcare provider provides a review of the result in conjunction with clinical presentation to make a diagnosis. The final assessment result is then a positive ASD diagnosis 3010 or a negative ASD diagnosis 3011.

Figure 31A:
FIG. 31A shows a login screen for a mobile device for assessing an individual in accordance with the platforms, systems, devices, methods, and media described herein.

FIG. 31A shows a login screen for a mobile device for assessing an individual in accordance with the platforms, systems, devices, methods, and media described herein. The login can include a username and password for accessing the personal account associated with a caregiver and/or the subject to be assessed.

Figure 31B:
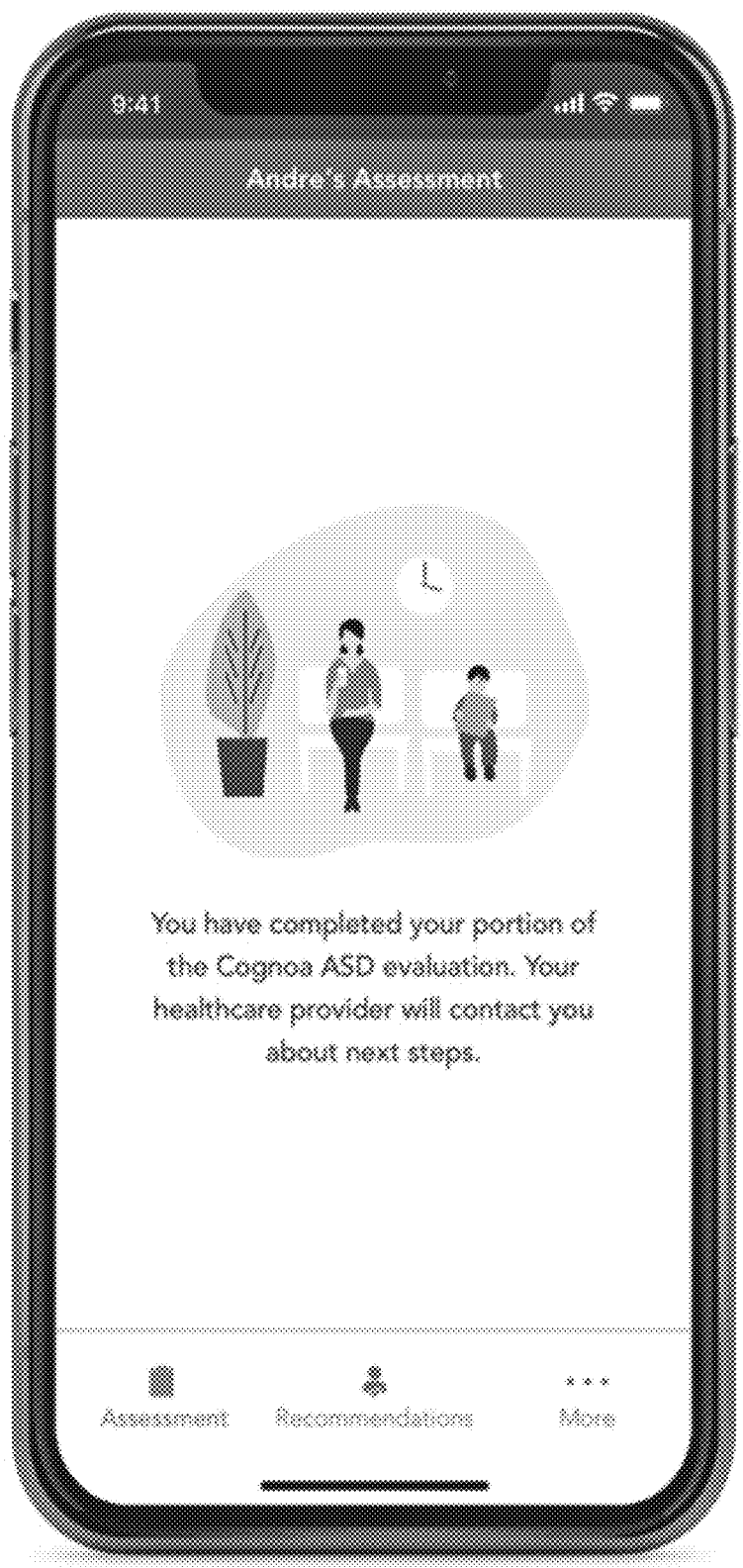
FIG. 31B shows a display screen of the mobile device indicating completion of a user portion of the an ASD evaluation.

FIG. 31B shows a screen of the mobile device indicating completion of a user portion of the an ASD evaluation, for example, of a first assessment module.

Figure 31C:
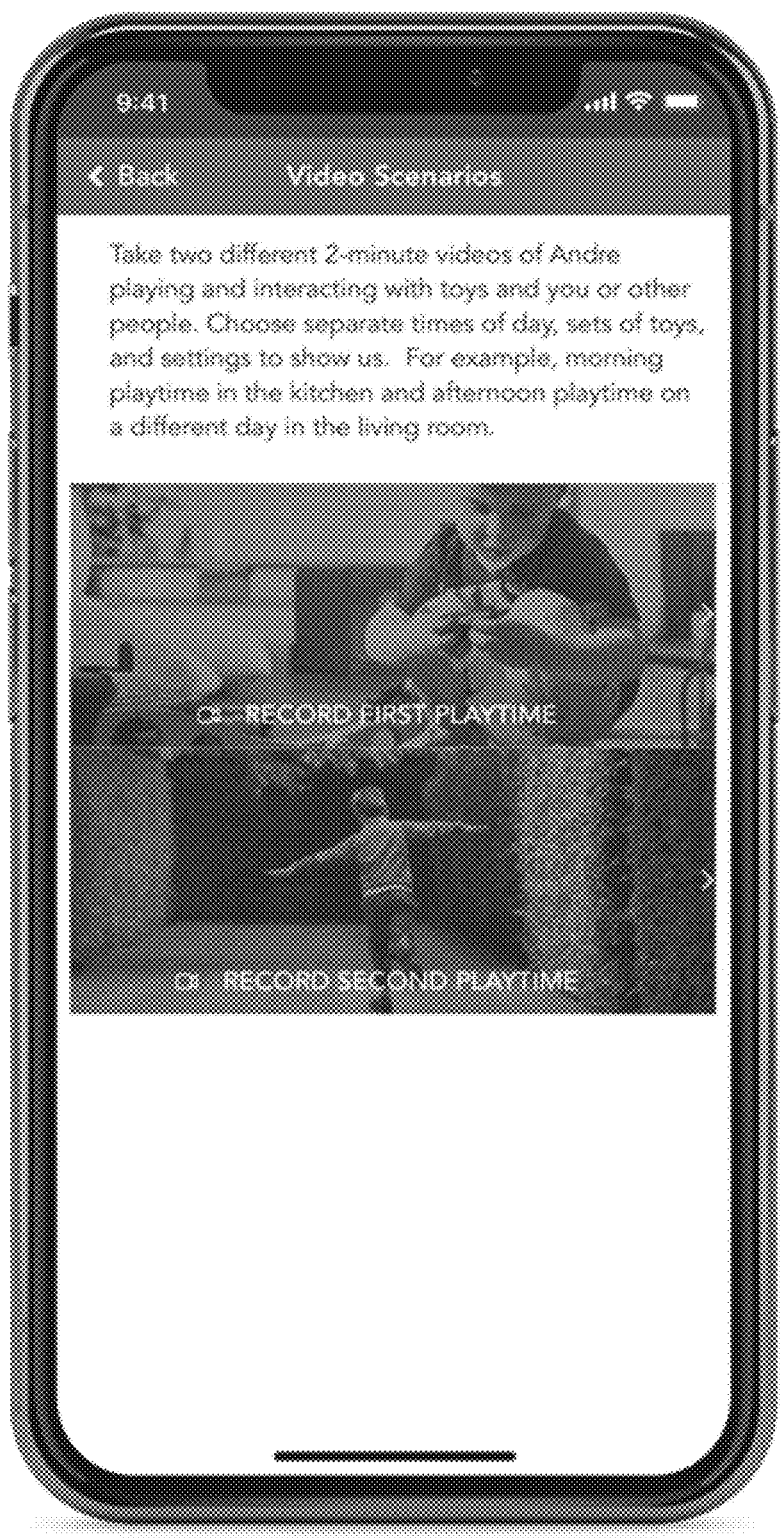
FIG. 31C shows a display screen of the mobile device providing instructions for capturing a video of the subject who is suspected as having ASD.

FIG. 31C shows a screen of the mobile device providing instructions for capturing a video of the subject who is suspected as having ASD. The screen shows interactive elements that are selectable by the user to initiate video recording for a first video and a second video corresponding to different play times by the subject.

Figure 31D:
FIG. 31D, FIG. 31E, and FIG. 31F show the display screens of the mobile device prompting a user to answer questions for use in assessing a subject in accordance with the platforms, systems, devices, methods, and media described herein.
Figure 31E:
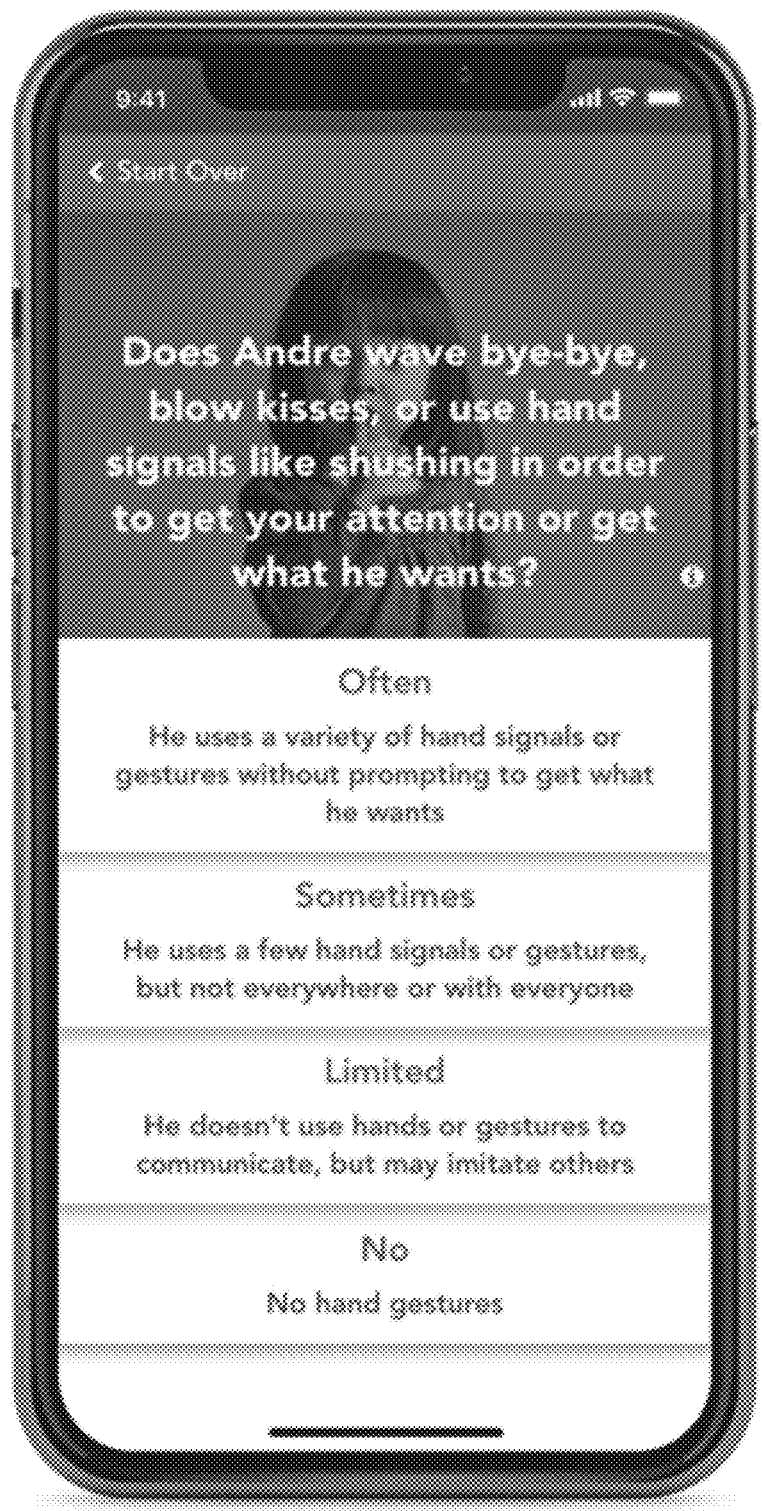
Figure 31F:
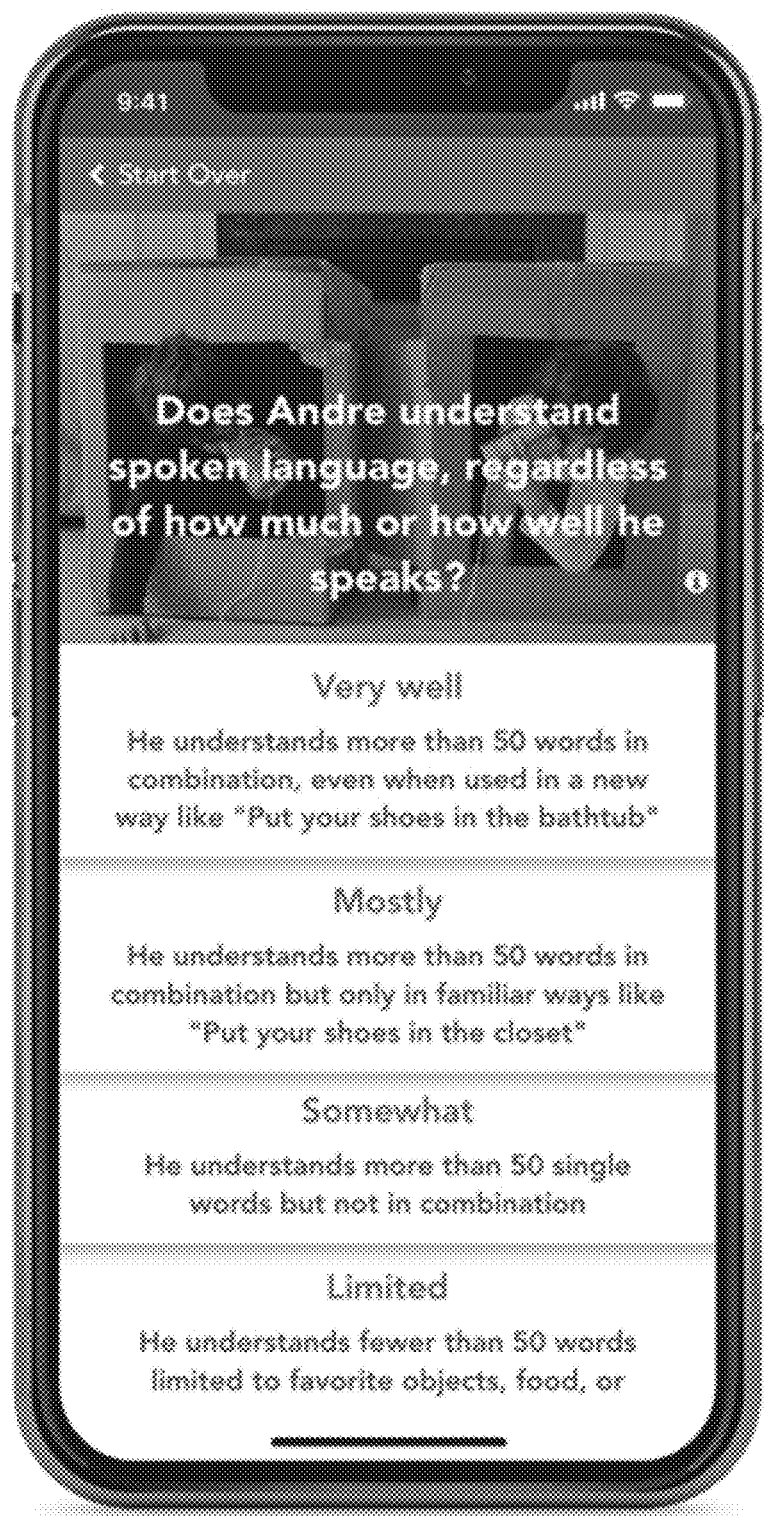

FIG. 31D, FIG. 31E, and FIG. 31F show screens of the mobile device prompting a user to answer questions for use in assessing a subject in accordance with the platforms, systems, devices, methods, and media described herein.

Figure 32:
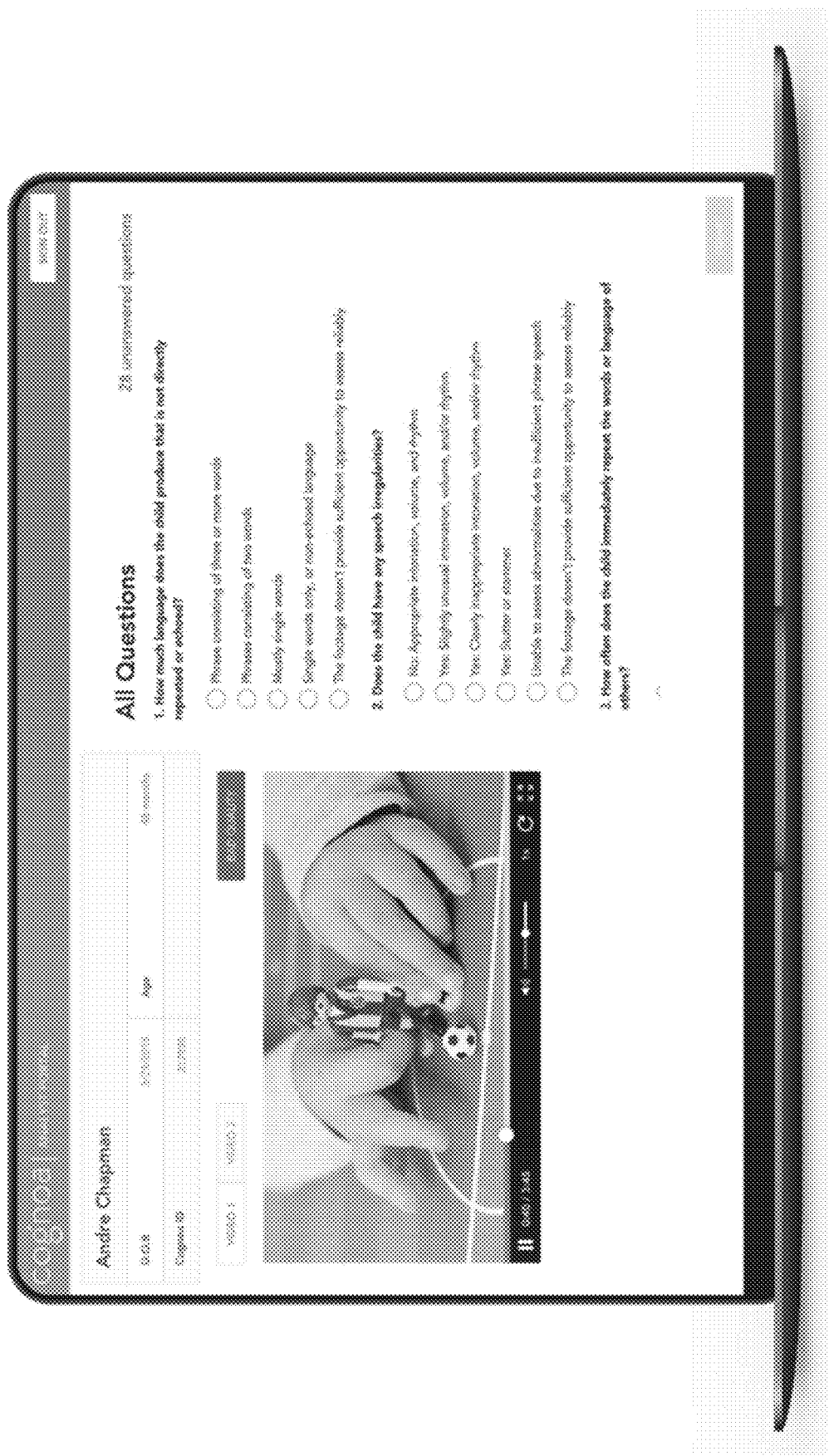
FIG. 32 shows a display screen of a video analyst portal displaying questions as part of a video analyst questionnaire in accordance with the platforms, systems, devices, methods, and media described herein.

FIG. 32 shows a display screen of a video analyst portal displaying questions as part of a video analyst questionnaire. The responses to this questionnaire can form a portion of the input to the assessment model(s) or classifier(s), for example, in a second assessment module as described herein.

Figure 33:
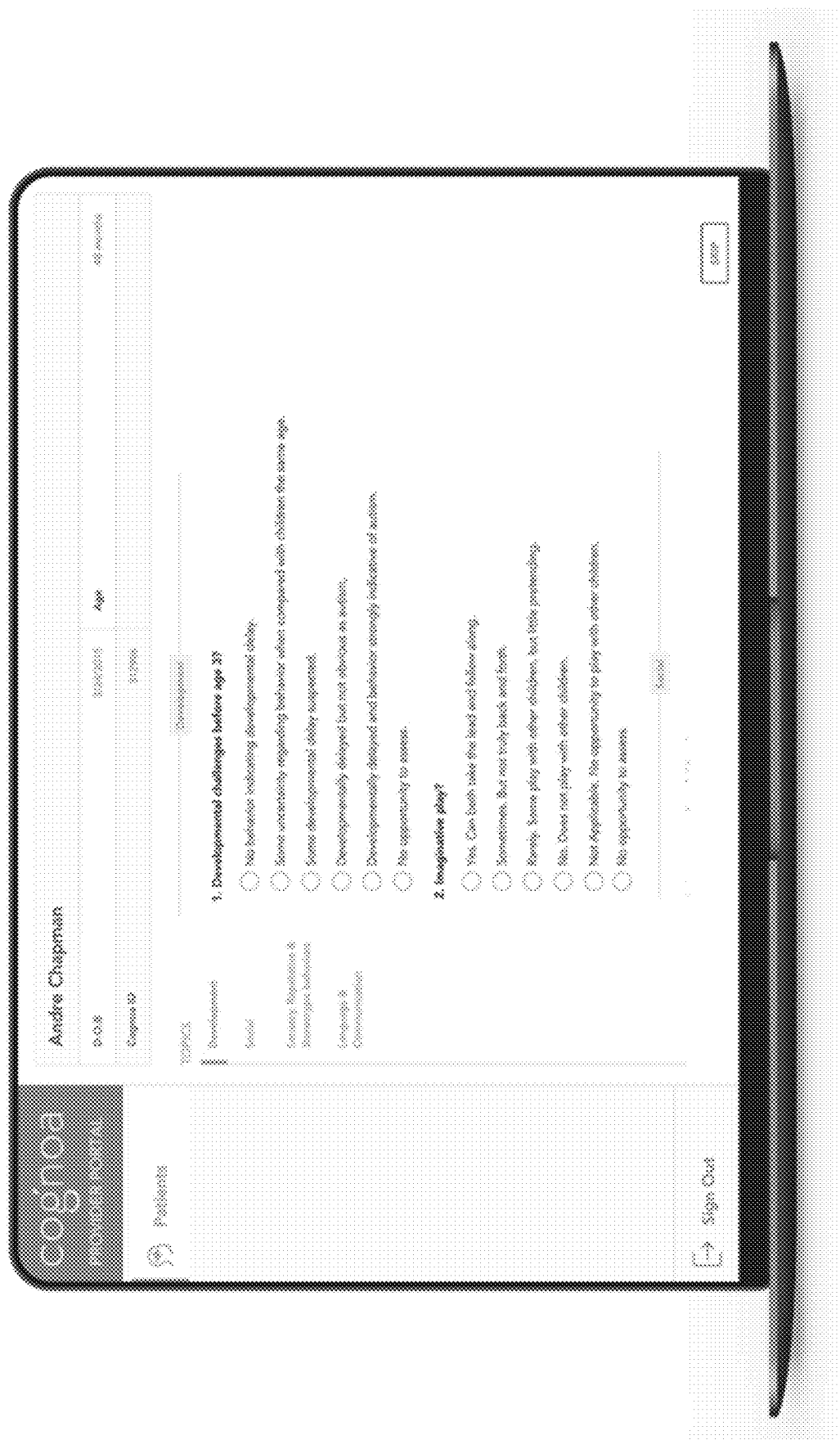
FIG. 33 shows a display screen of a healthcare provider portal displaying questions as part of a healthcare provider questionnaire in accordance with the platforms, systems, devices, methods, and media described herein.

FIG. 33 shows a display screen of a healthcare provider portal displaying questions as part of a healthcare provider questionnaire. The responses to this questionnaire can form a portion of the input to the assessment model(s) or classifier(s), for example, in a third assessment module as described herein.

Figure 34:
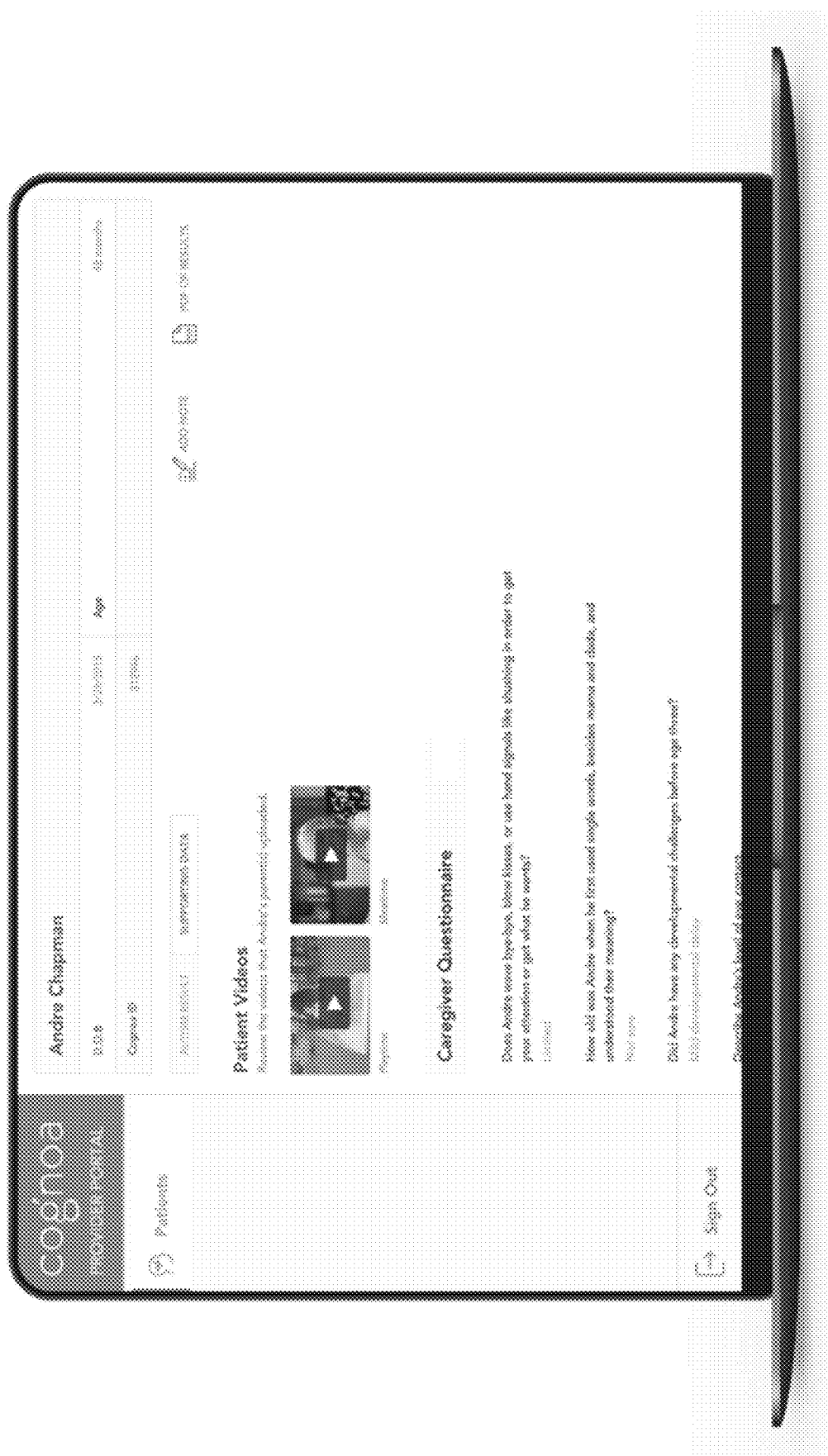
FIG. 34 shows a display screen of a healthcare provider portal displaying uploaded information for an individual including videos and a completed caregiver questionnaire in accordance with the platforms, systems, devices, methods, and media described herein.

FIG. 34 shows a display screen of a healthcare provider portal displaying uploaded information for an individual including videos and a completed caregiver questionnaire in accordance with the platforms, systems, devices, methods, and media described herein.

Figure 35:
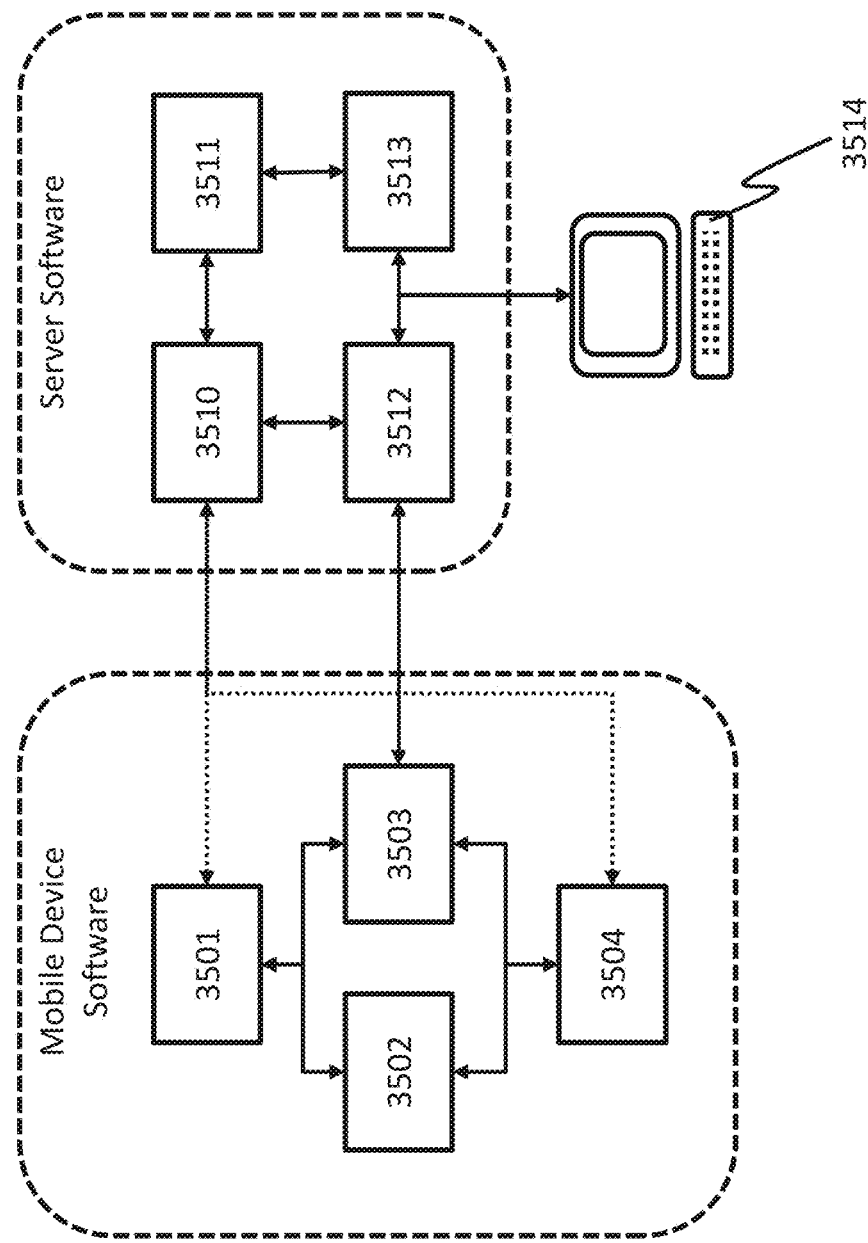
FIG. 35 shows a diagram of a platform for providing digital therapy to a subject as described herein, including the mobile device software and server software.

FIG. 35 shows a diagram of a platform for providing digital therapy to a subject as described herein, including the mobile device software and server software. The mobile device software includes an augmented reality game module 3501, an emotion recognition engine 3502, a video recording/playback module 3503, and a video review game 3504 (e.g., emotion guessing or recognition game). The server software includes an API service 3510, an application database 3511, video storage 3512, healthcare provider portal 3513, and the healthcare provider or therapist review portal 3514 on a local computing device.

Figure 36:
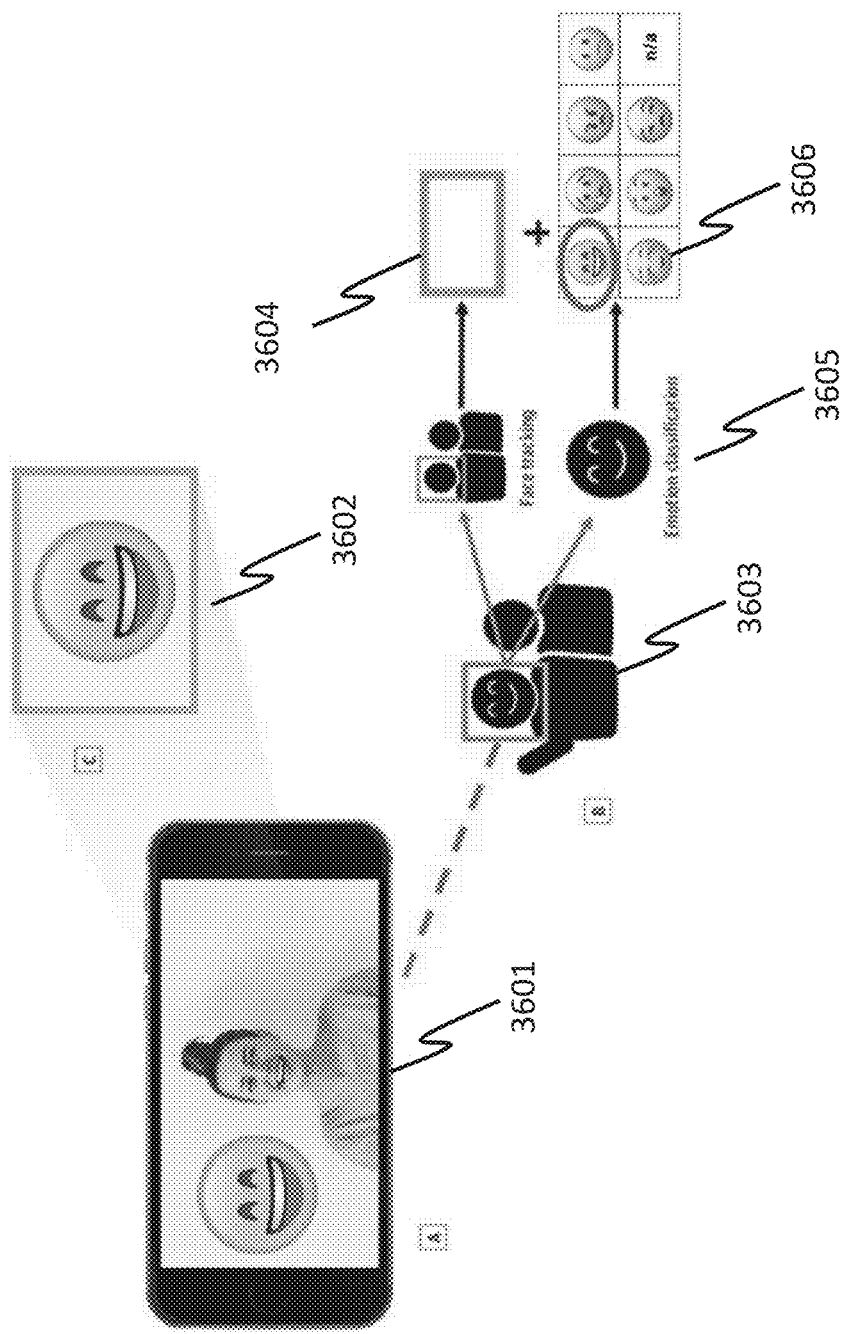
FIG. 36 shows a diagram of a device configured to provide digital therapy in accordance with the platforms, systems, devices, methods, and media described herein.

FIG. 36 shows a diagram of a device configured to provide digital therapy in accordance with the platforms, systems, devices, methods, and media described herein. In this illustrative example, the device is a smartphone 3601 having an outward facing camera that allows a user to capture one or more images (e.g., photographs or video) of another individual 3603. Face tracking is performed to identify one or more faces 3604 within the one or more images. The identified face is analyzed in real-time for emotion classification 3605. The classification is performed using a classifier configured to categorize the face as exhibiting an emotion selected from a plurality of emotions 3606. In this example, the smartphone 3601 is in an unstructured play or otherwise free roaming mode in which the classified emotion is portrayed with a corresponding emoticon 3602 on the display screen to provide dynamic or real-time feedback to the user.

Figure 37:
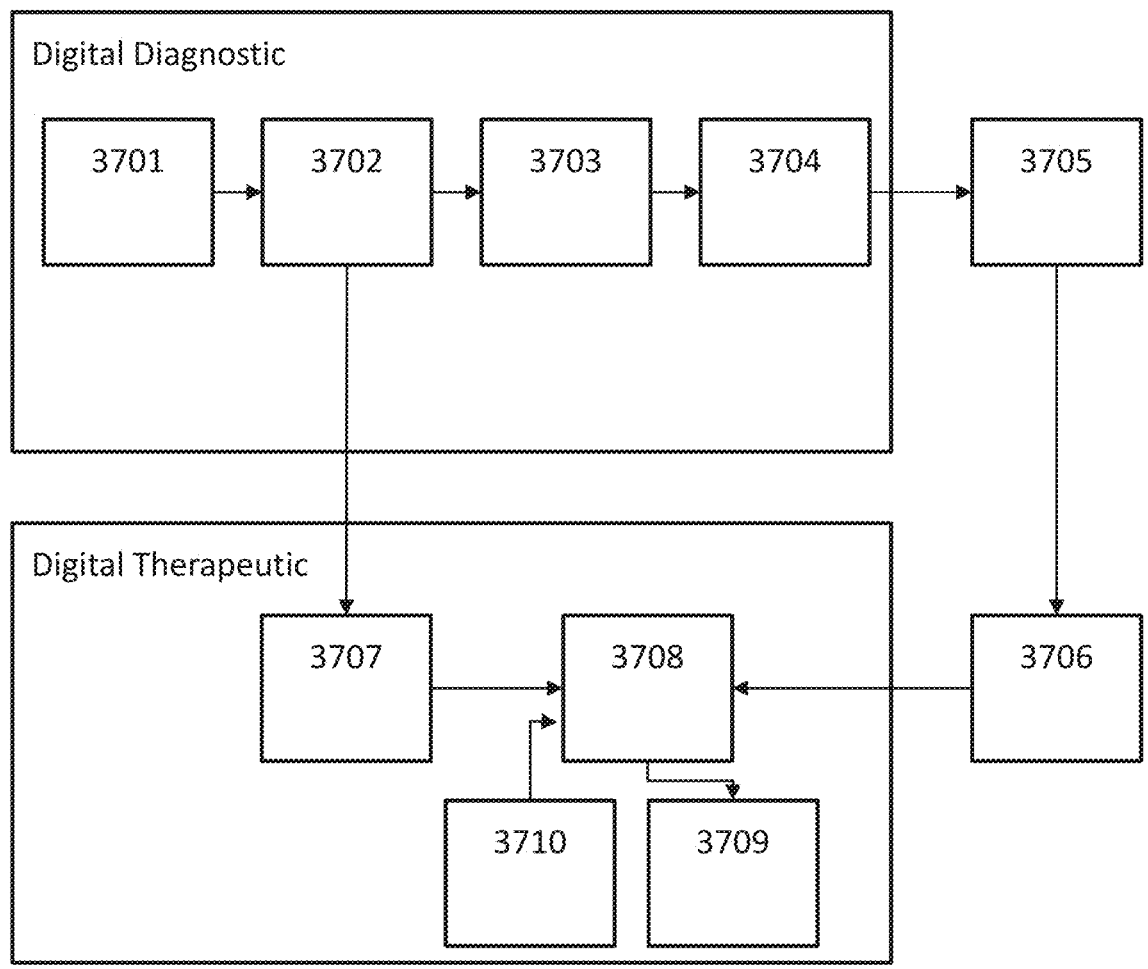
FIG. 37 shows an operational flow of a combined digital diagnostic and digital therapeutic in accordance with the platforms, systems, devices, methods, and media described herein.

FIG. 37 shows an operational flow of a combined digital diagnostic and digital therapeutic. In this non-limiting embodiment, the digital diagnostic operations include the application of diagnostic input modalities 3701 (e.g., inputs corresponding to parent/caretaker questionnaire, clinician questionnaire, video-based inputs, sensor data, etc.). The input data is then used in the computation of internal diagnostic dimensions 3702, for example, a subject can be projected onto a multi-dimensional diagnostic space based on the input data. The diagnostic dimensions are projected into scalar output 3703. This scalar output is evaluated against a threshold 3704. For example, a threshold can be a scalar value that determines the cut-off between a positive, negative, and optionally an inconclusive determination for the presence of a disorder, condition, or impairment, or a category or group thereof. Accordingly, the resulting outcome or prediction is generated 3705. The outcome or prediction can be a predicted medical diagnosis and/or can be taken into account by a clinician in making a medical diagnosis. Next, a therapy can be prescribed 3706 based on the diagnosis or outcome of the diagnostic process. The digital therapeutic operations include obtaining or receiving the internal diagnostic dimensions 3707 from the digital diagnostic operations. The customized and/or optimized therapeutic regimen is then generated 3708 based on the internal diagnostic dimensions 3707 and the prescription 3706. The digital therapeutic regimen is then administered 3709, for example, through the same computing device used to make the diagnosis or evaluation of the subject. The digital therapeutic regimen can include one or more activities or games determined to increase or maximize improvements in the subject with respect to one or more functions associated with the diagnosed disorder, condition, or impairment. For example, the activities or games can include emotional cue recognition activities using facial recognition and automatic real-time emotion detection implemented via a smartphone or tablet. User progress can be tracked and stored in association with the specific user or subject 3710. Progress tracking allows for the monitoring of performance and adjustments or changes to the games or activities based on the progress over time. For example, the customized therapeutic regimen for the subject is shifted away from activities or games that the subject is excelling at, or alternatively, the difficulty level is increased.

EXAMPLES

Example 1—Assessment Modules

A smartphone device is configured with a series of assessment modules configured to obtain data and evaluate the data to generate an assessment of an individual.

Module 1—Caregiver Assessment

The caregiver assessment is designed to probe behavioral patterns similar to those probed by a standardized diagnostic instrument, the Autism Diagnostic Interview—Revised (ADIR)—but is presented in a simplified manner in order to be concise and easy for caregivers to understand.

The device presents a minimal set of the most predictive questions to the caregiver to identify key behavioral patterns. A caregiver will be provided a series of multiple-choice questions based on the age of the child, which is typically completed within 10-15 minutes.

For children 18 through 47 months, the caregiver will be asked to answer 18 multiple-choice questions which fall into the following categories:
Non-verbal communication
Social interaction
Unusual sensory interests/reactions.

For children 48 through 71 months, the caregiver will be asked to answer 21 multiple-choice questions which fall into the following categories:
Non-verbal communication
Reciprocal verbal communication
Social interaction
Unusual sensory interests/reactions
Repetitive/Restricted behaviors or interests.

Module 2—Video Analysis

Module 2 requires caregivers to upload 2 videos each of at least 1 minute in duration of the child's natural play at home with toys and other people. Detailed instructions are provided in-app to the caregiver. The videos are uploaded securely to a HIPAA secure server. Each submission is scored by analysts independently of each other who evaluate behaviors observed by answering a series of multiple-choice questions evaluating phenotypic features of ASD on the combinative videos. The video analysts do not have access to the caregiver responses from Module 1 or the HCP responses from Module 3.

For children 18-47 months old, the video analyst evaluates the child's behavior with 33 questions while children 48-71 months old are evaluated with 28 questions which fall into the following categories:
Non-verbal and verbal communication
Social interaction
Unusual sensory interests/reactions
Stereotyped or repetitive motor movements, use of objects, or speech.

For every question, the analysts have the option of selecting: "The footage doesn't provide enough opportunity to assess reliably." In addition, analysts may deem a submission un-scorable if one or more videos are unhelpful for any reason such as: poor lighting, poor video or audio quality, bad vantage point, child not present or identifiable within a group, insufficient interaction with the child. If un-scorable, caregivers will be notified and requested to upload additional videos.

The algorithm underlying the medical device will use the questionnaire answers coming from each of the video analysts separately, as follows: for each of the analysts, the fully answered questionnaire will be input to the Module 2 algorithm as a set of input features, to which the algorithm will output a numerical response internally. This will be repeated for each of the analysts individually, resulting in a set of numerical responses. The numerical responses will then be averaged, and the average of the responses will be considered the overall output of Module 2. The output of Module 2 is then combined with the output of the other modules in order to arrive at a singular categorical outcome.

Module 3—Healthcare Provider Assessment

The HCP will be provided a series of questions based on the age of the child. For children 18 through 47 months, the HCP will be asked to answer 13 multiple-choice questions. For children 48 through 71 months, the HCP will be asked to answer 15 multiple-choice questions. Prior to completing Module 3, the HCP will not have access to the caregiver responses from Module 1. The HCP will not have access to the video analysts responses from Module 2. The questions fall into the following categories:
Development
Language and communication
Sensory, repetitive, and stereotypic behavior
Social Algorithmic Outputs After the (3) modules are completed, the inputs are evaluated to determine whether there is sufficient information to make a determination.

The dynamic algorithms used to generate the determination:
Utilize non-observable co-dependencies and non-linearity of information
Identify a minimal set of maximally predictive features
Can dynamically substitute "next most relevant" information to generate diagnostic output Underlying each of the Modules 1, 2, and 3 comprising the medical device is an independently trained machine learning predictive model. Each of the three models is trained offline using a dedicated training set of thousands of samples of historical medical instrument scoresheets at the question-answer item level, as well as the corresponding diagnostic labels, such that the training process is a supervised machine learning run. The machine learning algorithmic framework is GBDT (Gradient Boosted Decision Trees), which, upon training on the data in the training set, produces a set of automatically-created decision trees, each using some of the input features in the training set, and each producing a scalar output when run on new feature data pertaining to a new patient submission. The scalar outputs from each of the trees is summed up in order to arrive at the total scalar output of the classification model. Therefore, when used in prediction, each of the three modules outputs a single scalar value that is considered an intermediate output of the overall algorithm.

The scalar outputs from each of the three classification algorithms are passed as inputs into a second stage combinatorial classification model, which is trained independently on 350 historical data submissions collected in clinical studies. This combinatorial model is probabilistic in nature and is trained to take into account the covariance matrix between all three individual module classifiers. It outputs a single scalar value that represents a combined output of all three modules, and its output is then compared to preset thresholds in order to produce a categorical outcome that can be considered a determination of whether the child is Positive for ASD or Negative for ASD.

The device is also designed to allow for no result output when the prediction is weak. If a categorical determination cannot be provided, the healthcare provider will be informed that the device is not able to provide a result for autism spectrum disorder (ASD) at that point of time ("No Result"). Specifically, a patient may exhibit sufficient number and/or severity of features for which the patient is unable to be confidently placed within the algorithmic classifier as being negative for ASD but exhibits insufficient number and/or severity of features for which the patient is unable to be confidently placed within the algorithmic classifier as being positive of ASD. In these cases, the Algorithm does not provide a result ("No Result" case). In most cases (patients), the Algorithm will provide one of two distinct diagnostic outputs—Positive ASD, Negative ASD.

Example 2—Patient Evaluation Overview

During a patient examination, the healthcare provider (HCP) has concerns about the child's development based on observations and/or caregivers' concerns. HCP then prescribes a device configured with a digital application and provides an overview of the device to the caregiver. Once the device has been dispensed by the pharmacy, the caregiver accesses the app. The caregiver leaves the HCP's office, downloads the app and creates an account. The caregiver is then prompted to answer questions about the child's behavior/development in the app (Module 1). Once done, caregiver is required to record and upload two videos of the child in the child's natural home environment. Detailed instructions are provided in the app. If videos are too short, too long or do not conform with technical instructions, the caregiver will not able to upload them and is provided with additional instructions as to what needs to be corrected in order to proceed. Once videos are uploaded, the caregiver is notified that they will be contacted for next steps.

Once videos are uploaded, trained video analysts are prompted to review uploaded videos through a video analyst portal. The video analysts are blinded to the caregiver responses in Module 1, as well as the HCP responses from Module 3. The video analysts answer questions about the child's behavior exhibited in the videos, subject to defined requirements and quality controls (Module 2). Caregivers may be notified that additional videos need to be uploaded if video analysts deem that a video is not "assessable".

Once the device is prescribed, the HCP is prompted by Cognoa to answer a set of questions about the child's behavior/development (Module 3). HCPs will follow their standard practice guidelines for documentation for completion of Module 3. Prior to answering Module 3 questions, the HCP is blinded to caregiver responses in Module 1 and Video Analysts responses from Module 2.

Once all 3 Modules are completed, dynamic machine-learning algorithms evaluate and combine the modules' inputs through complex multi-level decision trees to provide an output. The HCP is notified to log in to the HCP dashboard and review the overall device's assessment result, alongside the instructions for use of the device indicating that the result should be used in conjunction with the clinical presentation of the patient.

The HCP reviews the device's result, in conjunction with medical evaluation of the child's clinical presentation to make a definitive diagnosis within his/her scope of practice. The device's result will help HCP to diagnose ASD, or to determine that the child does not have ASD.

In some cases, the HCP will be notified that the device is not able to provide a result. In these cases, the HCP must make the best decision for the patient at his/her discretion; however, in this situation, the Device makes no recommendations, nor does it provide further clinical instructions or guidance on next steps for the HCP.

Lastly, after the Device has rendered an output, the HCP will have access to caregiver responses to Module 1, raw patient videos and the clinical performance testing data regarding the device.

Example 3—ASD Positive Evaluation Scenarios

ASD Positive Scenario A

During a patient examination in a primary care setting, a licensed healthcare provider has concerns about a 2 year-old child's development based on observations and caregiver's concern. The patient has speech delay and his mother states he does not respond to his name when called, but his hearing evaluation was normal and he can become easily irritated by soft sounds. The primary healthcare provider assesses whether the use of the Cognoa Device is appropriate according to the device's labeling and directs the caregiver to use the device via a prescription.

The caregiver leaves the clinic, downloads the software, completes Module 1 and uploads videos of the patient. Video Analysts complete Module 2 by scoring the submitted videos via the Analyst Portal. The healthcare provider accesses Module 3 via the Provider Portal and completes the healthcare provider questionnaire. The device analyzes the information provided considering key developmental behaviors that are most indicative of autism and the healthcare provider is notified of the device result once available. The healthcare provider is presented with a report indicating the patient is "Positive for ASD" and the supporting data that were used to determine the result are available for the healthcare provider to review.

The healthcare provider reviews the result and determines that the result matches the clinical presentation and provides the diagnosis of ASD in a face-to-face visit with the caregiver where the diagnosis is explained and therapies are prescribed as per the American Academy of Pediatrics recommendations.

ASD Positive Scenario B

During a patient examination in a primary care setting, a licensed healthcare provider evaluates a 3½ year old child's development. The patient has odd use of language but speech is not delayed. Parents report she also makes odd repetitive noises. She seems to lack awareness of danger and often invades the personal space of strangers. The healthcare provider assesses whether the use of the Device is appropriate according to the device's labeling and directs the caregiver to use the device via a prescription.

The caregiver leaves the clinic, downloads the software, completes Module 1 and uploads videos of the patient. Video Analysts complete Module 2 by scoring the submitted videos via the Analyst Portal. The healthcare provider accesses Module 3 via the Provider Portal and completes the healthcare provider questionnaire. The device analyzes the information provided considering key developmental behaviors that are most indicative of autism and the healthcare provider is notified of the device result once available. The healthcare provider is presented with a report indicating the patient is "Positive for ASD" and the supporting data that were used to determine the result are available for the healthcare provider to review.

The healthcare provider reviews the Device result and determines that the result is most consistent with ASD. The healthcare provider provides the diagnosis of ASD in a face to face visit with the caregiver where the diagnosis is explained and therapies are prescribed as per the American Academy of Pediatrics recommendations.

Example 4—ASD Negative Evaluation Scenario

ASD Negative Scenario A

During a patient examination in a primary care setting, a licensed healthcare provider evaluates a 5 year old child's development. The patient has hyperactive behavior and is easily distractible. His mother states he does not respond to his name when called and she needs to call him several times before he acknowledges her. The patient also struggles with peer relationships and has difficulty making friends. The healthcare provider is concerned about possible autism but is most suspicious of ADHD. The healthcare provider assesses whether the use of the Device is appropriate according to the device's labeling and directs the caregiver to use the device via a prescription. The healthcare provider also requests for the parent and Kindergarten teacher to complete the Vanderbilt ADHD assessment.

The caregiver leaves the clinic, downloads the software, completes Module 1 and uploads videos of the patient. Video Analysts complete Module 2 by scoring the submitted videos via the Analyst Portal. The healthcare provider accesses Module 3 via the Provider Portal and completes the healthcare provider questionnaire. The device analyzes the information provided considering key developmental behaviors that are most indicative of autism and the healthcare provider is notified of the device result once available. The healthcare provider is presented with a report indicating the patient is "Negative for ASD" and the supporting data that were used to determine the result are available for the healthcare provider to review.

The healthcare provider reviews the Device result and the Vanderbilt assessment to determine that the diagnosis is most consistent with ADHD. The healthcare provider provides the diagnosis of ADHD predominantly hyperactive type in a face to face visit with the caregiver where the diagnosis is explained and therapies are prescribed as per the American Academy of Pediatrics recommendations.

The healthcare provider monitors the patient's response to behavioral therapy and prescribes a non-stimulant ADHD medication keeping the possibility of ASD in the differential diagnosis. The patient responds well to therapy and medication with no longer exhibiting signs concerning for ASD reinforcing the diagnosis of ADHD.

ASD Negative Scenario B

During a patient examination in a primary care setting, a parent reports that the 18 month patient's older sibling has an autism diagnosis and his father has noted some episodes of aggressiveness and possible stereotypic behaviors. The patient has met all his developmental milestones and his examination and interactions in the clinic are age appropriate. The father shows the healthcare provider videos of the patient exhibiting stereotypic behaviors similar to the older sibling. The healthcare provider assesses whether the use of the Cognoa Device is appropriate according to the device's labeling and directs the caregiver to use the device via a prescription. The caregiver leaves the clinic, downloads the software, completes Module 1 and uploads videos of the patient. Cognoa Video Analysts complete Module 2 by scoring the submitted videos via the Cognoa Analyst Portal. The healthcare provider accesses Module 3 via the Cognoa Provider Portal and completes the healthcare provider questionnaire.

The device analyzes the information provided considering key developmental behaviors that are most indicative of autism and the healthcare provider is notified of the device result once available. The healthcare provider is presented with a report indicating the patient is "Negative for ASD" and the supporting data that were used to determine the result are available for the healthcare provider to review. The healthcare provider reviews the Cognoa Device result and determines that the patient is most likely imitating the older sibling. The healthcare provider monitors the patient's development and provides parenting guidance on redirection when the patient exhibits aggressive or stereotypic behaviors.

Example 5—ASD Inconclusive Evaluation Scenario

ASD Inconclusive Scenario A

During a patient examination in a primary care setting, a 5½ year old is reported by the parent to have learning difficulties and the school has recommended an individualized education plan assessment be performed for possible placement into the special education system. The patient makes poor eye contact with the healthcare provider in the clinic and is slow to answer questions with a flattened affect. There are no signs of neglect or abuse and no reported hallucinations. Laboratory evaluation reveal a normal CBC, CMP, and TSH. The healthcare provider assesses whether the use of the Cognoa Device is appropriate according to the device's labeling and directs the caregiver to use the device via a prescription. The caregiver leaves the clinic, downloads the software, completes Module 1 and uploads videos of the patient.

Video Analysts complete Module 2 by scoring the submitted videos via the Analyst Portal. The healthcare provider accesses Module 3 via the Provider Portal and completes the healthcare provider questionnaire. The device analyzes the information provided considering key developmental behaviors that are most indicative of autism and the healthcare provider is notified that the device cannot provide a result regarding ASD at this point in time based on the information provided. Use of the Device stops at this point.

At this point, the HCP uses their professional decision-making to determine the next steps for the patient.

ASD Inconclusive Scenario B

Since starting Kindergarten, a 5 year old who has had speech delay but has been making progress in speech therapy, has been noted by his teacher as arguing frequently with adults, losing his temper easily, refusing to follow rules, blaming others for his own mistakes, deliberately annoying others, and otherwise behaving in angry, resentful, and vindictive ways. The parent brings these concerns to the child's primary care healthcare provider. The healthcare provider assesses whether the use of the Device is appropriate according to the device's labeling and directs the caregiver to use the device via a prescription. The caregiver leaves the clinic, downloads the software, completes Module 1 and uploads videos of the patient.

Video Analysts complete Module 2 by scoring the submitted videos via the Analyst Portal. The healthcare provider accesses Module 3 via the Provider Portal and completes the healthcare provider questionnaire. The device analyzes the information provided considering key developmental behaviors that are most indicative of autism and the healthcare provider is notified that the device cannot provide a result regarding ASD at this point in time based on the information provided. Use of the Device stops at this point.

At this point, the HCP use their professional decision-making to determine the next steps for the patient.

Example 6—Emotion Recognition Digital Therapy

A patient is assessed using the device as described in any of the preceding examples and determined to be positive for ASD. The device used for assessment and/or a different device is configured with a digital therapy application for treating the patient through training for emotion recognition ("therapeutic device"). In this case, the device is a smartphone configured with a mobile application for providing the digital therapy. The HCP prescribes the device and/or mobile application for treating the patient. The patient or a parent or caregiver is given access to the therapeutic device and registers/logs into a personal account for the mobile application. The mobile application provides selectable modes for the patient including an activity mode comprising emotion elicitation activities, emotion recognition activities, and unstructured play.

The patient or a parent or caregiver selects unstructured play, causing the device to activate the camera and display a graphic user interface that dynamically performs facial recognition and emotion detection/classification in real time as the patient points the outward facing camera towards other persons. When the patient points the camera at a particular individual, an image of the individual is analyzed to identify at least one emotion, and the graphic user interface displays the emotion or a representation thereof (e.g., an emoji or words describing or corresponding to the emotion). This allows the patient to observe and learn the emotion(s) that are being displayed by the person being observed with the camera. In some cases, there is a delay in the display of the emotion on the interface to allow the patient time to attempt to identify the emotion before being given the "answer". Each positively identified emotion and its corresponding image(s) is then stored in an image library.

The caregiver moderates the digital therapy session, wherein the child uses the smartphone to walk around their home, office, or other familiar environment, and "find" or try to elicit an emotion that is prompted by audio in-app. Often, in the home setting, the emotion will be generated by the caregiver; the instructions to the caregiver will be to replicate the requested emotion or to intentionally provide the wrong face. During use of the device in areas with multiple people, the caregiver instructions will instruct the caregiver to help the child find individuals with the prompted facial expression; if none exist, the caregiver may choose to replicate the emotion or prompt another individual in close proximity to replicate the emotion without alerting the child. The child points the phone camera towards the individual who they believe is expressing the prompted emotion; the mobile app has an Augmented Reality (AR) component wherein there is an alert to the child when a face is detected. The screen then provides the child real-time audio and visual feedback correctly labeling the emotional expression displayed on the face (e.g., an emoticon is displayed in real-time, on-screen, with the corresponding emotion). The emoticon remains on screen in the augmented reality environment as the child continues using the product After the patient has collected a number of images in the image library, the patient then switches out of the unstructured play activity and selects the emotion recognition activities. The patient then selects an emotion recognition game or emotion guessing game for reinforcement learning.

An emotion guessing game stores previous images that the child has evaluated mixed with stock face images (from pre-reviewed sources). The goal of this activity is to (a) review images that were not evaluated correctly by the children and have the caregiver correct it and (b) reinforce and remind the child of their correct choices to improve retention. The child can then try to correctly match or label the emotional expressions displayed in the images. The goal from this EGG is to reinforce the learnings from the augmented reality unstructured play session in a different, 2D environment. It also provides additional social interaction opportunities between caregiver and child to review and discuss the emotions together.

Various reinforcement learning games are provided for selection by the patient. Examples of these games are shown below:

(A) A game shows three images that the patient has collected (may be mixed with stock images) that have been classified as showing three different emotions: happy, sad, and angry. The game provides a visual and audio prompt asking the patient to select the image that shows the "happy" emotion. The patient selects a image, and is then given feedback based on whether the selection is correct. The patient proceeds to complete several of these activities using various images that have been collected.

(B) A game shows a single image of a person that the patient has collected (or stock image) and is presented with a prompt to determine the emotion shown in the image. The patient can be shown a multiple choice selection of emotions. The emotions may be selectable or the patient may be able to drag the emotion to the image or vice versa.

(C) A mix and match emotion recognition activity. In this case, a column of 3 collected (or stock) images are displayed on the left of the graphic user interface screen, and a column of 3 emotions are displayed on the right of the graphic user interface. The interface allows the user to select an image and then a corresponding emotion to "match" them together. Once the images and emotions have all been matched, the patient is provided with feedback based on performance. Alternatively, two columns of images and emotions are shown, and the patient is able to drag and drop to align an image with a corresponding emotion in the same row in order to "match" them together.

(D) A dynamic emotion sorting game. Two or more buckets are provided at the bottom of the screen, each bucket having an emotion label, while various collected images float through the screen. The patient is instructed to drag each image into the appropriate bucket. Once all images have been sorted into a bucket, the patient is provided with feedback based on performance.

The emotion recognition games and activities described herein can be provided for various emotion recognition and learning purposes and not just for reinforcement learning using collected images that the user has already been exposed to. The patient's performance during an activity can be tracked or monitored when available. As the patient completes an activity in a sequence of activities, the next activity provided can be biased or weighted towards selection of images that test for emotions where the patient has relatively poor performance.

The patient then switches to emotion elicitation activities. These activities are designed to provide stimulus calculated to evoke an emotion. The emotional stimulus is selected from an image, a sequence of images, a video, a sound, or any combination thereof. Examples of emotional stimuli include audiovisual content designed to elicit fear (spider, monster) and happiness or joy (children's song or show). The emotional response elicited in the patient can be determined by an inward facing camera of the device. For example, the camera can capture one or more images of the patient's face while the emotional stimulus is being provided, which are then evaluated to detect any emotional response. The response can be monitored over time to track any changes in the patient's responsiveness to emotional stimuli.

Example 7—Digital Diagnostic and Digital Therapy

A patient is assessed using a smartphone device in accordance with any of the preceding examples and determined to be positive for ASD. This positive assessment is then taken into account by a HCP who diagnoses the patient as having ASD and prescribes the patient a digital therapy application for treating the patient through the same smartphone device. The patient or a parent or caregiver is given access to the therapeutic device and registers/logs into a personal account for the mobile application. The personal account contains the diagnostic information used in assessing the patient. This diagnostic information is computed to determine the patient's position within a multi-dimensional space relating to various aspects of the ASD such as, for example, specific impairments like decreased social reciprocity. These internal diagnostic dimensions are then used to identify an activity that is predicted to improve the patient's impaired ability to engage in social reciprocity.

The identified activity is an activity mode comprising activities for monitoring and improving social reciprocity. One example of such an activity mode for monitoring and improving social reciprocity is a modification of the unstructured play in which the user is prompted to respond to the facial expression or emotional cue detected in the parent or caregiver.

The patient or a parent or caregiver selects the modified unstructured play, causing the device to activate both the inward-facing camera and the outward-facing camera, and display a graphic user interface that dynamically performs facial recognition and emotion detection/classification in real time of a target individual (e.g., a parent) as the patient points the outward facing camera towards other persons and the patient using the inward facing camera (e.g., selfie camera). When the patient points the camera at a particular individual, one or more images or video of the individual is analyzed to identify at least one emotion, and the graphic user interface displays the emotion or a representation thereof (e.g., an emoji or words describing or corresponding to the emotion). This allows the patient to observe and learn the emotion(s) that are being displayed by the person being observed with the camera. In some cases, there is a delay in the display of the emotion on the interface to allow the patient time to attempt to identify the emotion before being given the "answer". Each positively identified emotion and its corresponding image(s) is then stored in an image library.

In addition to detection of the target individual's emotion, the device captures images or video of the patient's facial expression and/or emotion simultaneously or close in temporal proximity to the analysis of the target individual. The social interaction between the patient and the target individual can be captured this way as the combined facial expression and/or emotion of both persons. The time stamps of the detected expressions or emotions of the individuals are used to determine a sequence of social interactions, which are then evaluated for the patient's ability to engage in social reciprocity. The patient's performance is monitored and linked to the personal account to maintain an ongoing record. This allows for continuing evaluations of the patient to generate updated diagnostic dimensions that can be used to update the customized therapeutic regimen.

In one instance, the patient points the phone at his parent who smiles at him. The display screen of the phone displays an emoticon of a smiley face in real time to help the patient recognize the emotion corresponding to his parent's facial expression. In addition, the display screen optionally provides instructions for the patient to respond to the parent. The patient does not smile back at his parent, and the inward facing camera captures this response in one or more images or video. The images and/or videos and a timeline or time-stamped sequence of social interactions are then saved on the device (and optionally uploaded or saved on a remote network or cloud). In this case, the parent's smile is labeled as a "smile", and the patient's lack of response is labeled as "non-responsive" or "no smile". Thus, this particular social interaction is determined to be a failure to engage in smile-reciprocity. The social interaction can also be further segmented based on whether the target individual (parent) and the patient expressed a "genuine" smile as opposed to a "polite smile". For example, the algorithms and classifiers described herein for detecting a "smile" or "emotion" can be trained to distinguish between genuine and polite smiles, which can be differentiated based on visual cues corresponding to the engagement of eye muscles in genuine smiles and the lack of eye muscle engagement in police smiles.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for assessing and providing treatment to an individual with respect to a behavioral disorder, a developmental delay, or a neurologic impairment, said device comprising:
 a processor;
 a non-transitory computer-readable medium that stores a computer program configured to cause said processor to:
 (a) receive an input for said individual related to said behavioral disorder, said developmental delay, or said neurologic impairment;
 (b) determine that said individual has an indication of a presence of said behavioral disorder, said developmental delay, or said neurologic impairment using a trained classifier module of said computer program that is trained using data from a plurality of individuals having said behavioral disorder, said developmental delay, or said neurologic impairment;
 (c) determine, using a machine learning model that is generated by said computer program, that said behavioral disorder, said developmental delay, or said neurologic impairment that said individual has said indication of said presence will be improved by a digital therapy that promotes social reciprocity;

(d) provide, using a mobile computing device comprising a smartphone, a tablet computer, a laptop, a smartwatch, or a wearable computing device, a digital therapy that promotes social reciprocity to said individual when it is determined that said behavioral disorder, said developmental delay, or said neurologic impairment will be improved by said digital therapy, said digital therapy comprising an augmented reality experience; and (e) obtain, using a camera of said mobile computing device, a video or an image of a person interacted with by said individual in said augmented reality experience.

2. The device of claim 1, wherein said machine learning model determines a degree of improvement that will be achieved by said digital therapy.

3. The device of claim 1, wherein said processor is configured with further instructions to determine an emotion associated with said person using an image analysis module to analyze said video or said image.

4. The device of claim 3, wherein said image analysis module comprises a facial recognition module for detecting the face of said person within said video or image.

5. The device of claim 4, wherein said image analysis module comprises a classifier trained using machine learning to categorize said face as exhibiting said emotion.

6. A device for assessing and providing treatment to an individual with respect to a behavioral disorder, a developmental delay, or a neurologic impairment, said device comprising:

a processor;

a non-transitory computer-readable medium that stores a computer program configured to cause said processor to:

(a) receive an input for said individual related to said behavioral disorder, said developmental delay, or said neurologic impairment;

(b) determine that said individual has an indication of a presence of said behavioral disorder, said developmental delay, or said neurologic impairment using a trained classifier module of said computer program that is trained using data from a plurality of individuals having said behavioral disorder, said developmental delay, or said neurologic impairment;

(c) determine, using a machine learning model that is generated by said computer program, that said behavioral disorder, said developmental delay, or said neurologic impairment that said individual has said indication of said presence will be improved by a digital therapy that promotes social reciprocity;

(d) provide a digital therapy that promotes social reciprocity to said individual when it is determined that said behavioral disorder, said developmental delay, or said neurologic impairment will be improved by said digital therapy, said digital therapy comprising a virtual reality experience comprising a displayed virtual person or character; and (e) determine an emotion expressed by said virtual person or character within said virtual reality experience.

7. The device of claim 6, wherein a description of said emotion is displayed to said individual in real time within said virtual reality experience by either printing said description on a screen of a mobile computing device or by sounding said description through an audio output coupled with said mobile computing device.

8. The device of claim 6, wherein said computer program is further configured to cause said processor to use an image analysis module comprising a facial recognition module for detecting a face of said virtual person or character within said video or image.

9. The device of claim 8, wherein said image analysis module comprises a classifier trained using machine learning to categorize said face as exhibiting said emotion.

10. The device of claim 6, wherein said machine learning model determines a degree of improvement that will be achieved by said digital therapy.

11. The device of claim 6, wherein said computer program is further configured to cause said processor to provide instructions with said digital therapy for said individual to engage in an activity mode.

12. The device of claim 11, wherein said activity mode comprises an emotion elicitation activity, an emotion recognition activity, or unstructured play.

13. The device of claim 12, wherein a therapeutic agent is provided to said individual together with said digital therapy.

14. The device of claim 1, wherein said device comprises said mobile computing device.

15. The device of claim 6, wherein said device comprises a mobile computing device.

16. The device of claim 15, wherein said mobile computing device is a smartphone, a tablet computer, a laptop, a smartwatch, or a wearable computing device.

* * * * *